US011629175B2

(12) United States Patent
Lashuel et al.

(10) Patent No.: US 11,629,175 B2
(45) Date of Patent: Apr. 18, 2023

(54) METHOD FOR PREPARING PHFS-LIKE TAU AGGREGATES

(71) Applicant: ECOLE POLYTECHNIQUE FEDERALE DE LAUSANNE (EPFL), Lausanne (CH)

(72) Inventors: Hilal A. Lashuel, Ecublens (CH); Nadine Ait-Bouziad, Ecublens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 17/050,579

(22) PCT Filed: Apr. 29, 2019

(86) PCT No.: PCT/EP2019/060969
§ 371 (c)(1),
(2) Date: Oct. 26, 2020

(87) PCT Pub. No.: WO2019/207164
PCT Pub. Date: Oct. 31, 2019

(65) Prior Publication Data
US 2021/0238242 A1 Aug. 5, 2021

(30) Foreign Application Priority Data
Apr. 27, 2018 (EP) .................................... 18169898

(51) Int. Cl.
*C07K 14/47* (2006.01)
*G01N 33/50* (2006.01)
*G01N 33/68* (2006.01)

(52) U.S. Cl.
CPC ...... *C07K 14/4711* (2013.01); *G01N 33/5014* (2013.01); *G01N 33/6896* (2013.01); *G01N 2500/04* (2013.01)

(58) Field of Classification Search
CPC ........... C07K 14/4711; G01N 33/5014; G01N 2500/04; G01N 2500/20; G01N 2800/7047
See application file for complete search history.

(56) References Cited

FOREIGN PATENT DOCUMENTS

| WO | 2001018546 A2 | 3/2001 |
|---|---|---|
| WO | 2014008404 A1 | 1/2014 |

OTHER PUBLICATIONS

Dinkel PD. Seeded Propagation of Tau Fibrils, A Dissertation. Nov. 2013, University of Denver. (Year: 2013).*
Iba M et al. Synthetic tau fibrils mediate transmission of neurofibrillary tangles in a transgenic mouse model of Alzheimer's-like tauopathy. J. Neurosci. 2013, 33(3): 1024-1037. (Year: 2013).*
Seidler PM et al. Structure-based inhibitors of tau aggregation. Nat. Chem. Feb. 2018, 10: 170-176; Epub Nov. 20, 2017. (Year: 2017).*
Strathopulos PB et al. Sonication of proteins causes formation of aggregates that resemble amyloid. Protein Sci. 2004, 13: 3017-3027. (Year: 2004).*
Barghorn, S., & Mandelkow, E., "Toward a Unified Scheme for the Aggregation of Tau into Alzheimer Paired Helical Filaments," Biochemistry, 41: 14885-14896 (2002).
Tomoo, K., et al., "Possible Role of Each Repeat Structure of the Microtubule-Binding Domain of the Tau Protein in In Vitro Aggregation," J. Biochem., 138(4): 413-423 (2005).
Morozova, O.A., et al., "Conformational Features of tau fibrils from Alzheimer's disease brain are faithfully propagated by unmodified recombinant protein," Biochemistry, 52(40): 6960-6967 (2013).
Tokimasa, M., et al., "Importance of local structures of second and third repeat fragments of microtubule-binding domain for tau filament formation," FEBS Letters, 579(17): 3481-3486 (2005).
Jeganathan, S., et al., "The Natively Unfolded Character of Tau and Its Aggregation to Alzheimer-like Paired Helical Filaments," Biochemistry, 47(40): 10526-10539 (2008).
Yao, T.M., et al., "Aggregation Analysis of the Microtubule Binding Domian in Tau Protein by Spectroscopic Methods," J. Biochem., 134(1): 91-99 (2003).
Yu, X., et al., "Cross-seeding and Conformational Selection between Three- and Four-repeat Human Tau Proteins," The Journal of Biological Chemistry, 287(18): 14950-14959 (2012).
Al-Hilaly, Y.K., et al., "Alzheimer's Disease-like Paired Helical Filament Assembly from Truncated Tau Protein is Independent of Disulfide Crosslinking," J. Mol. Biol., 429(23): 3650-3665 (2017).
International Search Report from PCT Application No. PCT/EP2019/060969 dated Jul. 19, 2019.
Written Opinion from PCT Application No. PCT/EP2019/060969 dated Jul. 19, 2019.

* cited by examiner

*Primary Examiner* — Kimberly Ballard
(74) *Attorney, Agent, or Firm* — Harness Dickey & Pierce P.L.C.

(57) ABSTRACT

The invention relates to a method for preparing PHFs-like Tau aggregates and to a method for identifying compounds that are inhibitors of Tau protein aggregation, blockers of Tau seeding and propagation, and imaging agents that specifically bind PHF.

6 Claims, 39 Drawing Sheets

Specification includes a Sequence Listing.

Figure 1

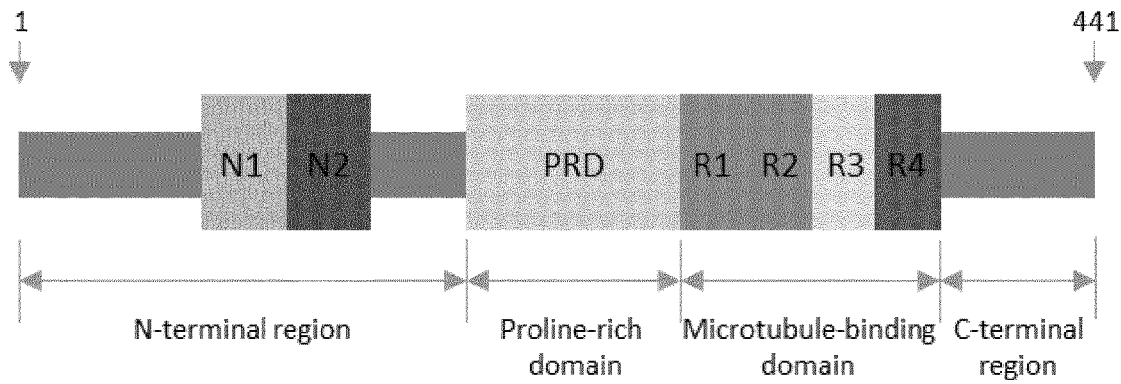

| | | |
|---|---|---|
| R2 | SEQ ID N°: 1 | VQIINKKLDLSNVQSKCGSKDNIKHV |
| | SEQ ID N°: 2 | *QTAPVPMPDLKNVKSKIGSTENLKHQPGGGK*VQIINKKLDLSNVQSKCGSKDNIKHV |
| | SEQ ID N°: 3 | VQIINKKLDLSNVQSKCGSKDNIKHV*PGGG* |
| | SEQ ID N°: 4 | VQIINKKLDLSNVQSKCGSKDNIKHV*SGGG* |
| Tau 4R2N | SEQ ID N° : 5 | MAEPRQEFEVMEDHAGTYGLGDRKDQGGYTMHQDQEGDTDAGLKESPLQTPTEDGSEEPGSETSDAKSTPTAEDVTAPLVDEGAPGKQAAAQPHTEIPEGTTAEEAGIGDTPSLEDEAAGHVTQARMVSKSKDGTGSDDKKAKGADGKTKIATPRGAAPPGQKGQANATRIPAKTPPAPKTPPSSGEPPKSGDRSGYSSPGSPGTPGSRSRTPSLPTPPTREPKKVAVVRTPPKSPSSAKSRL*QTAPVPMPDLKNVKSKIGSTENLKHQPGGGK*VQIINKKLDLSNVQSKCGSKDNIKHV*PGGG*SVQIVYKPVDLSKVTSKCGSLGNIHHKPGGGQVEVKSEKLDFKDRVQSKIGSLDNITHVPGGGNKKIETHKLTFRENAKAKTDHG |

Cont. Fig. 1

| | | AEIVYKSPVVSGDTSPRHLSNVSSTGSIDMVDSPQL ATLADEVSASLAKQGL |
|---|---|---|
| K18 | SEQ ID N° : 6 | *QTAPVPMPDLKNVKSKIGSTENLKHQPGGGK*VQIIN KKLDLSNVQSKCGSKDNIKHV*PGGG*SVQIVYKPV DLSKVTSKCGSLGNIHHKPGGGQVEVKSEKLDFKD RVQSKIGSLDNITHVPGGGNKKIE |
| Tau 4R1N | SEQ ID N° : 7 | MAEPRQEFEVMEDHAGTYGLGDRKDQGGYTMHQ DQEGDTDAGLKESPLQTPTEDGSEEPGSETSDAKST PTAEAEEAGIGDTPSLEDEAAGHVTQARMVSKSKD GTGSDDKKAKGADGKTKIATPRGAAPPGQKGQAN ATRIPAKTPPAPKTPPSSGEPPKSGDRSGYSSPGSPGT PGSRSRTPSLPTPPTREPKKVAVVRTPPKSPSSAKSR LQTAPVPMPDLKNVKSKIGSTENLKHQPGGGKVQI INKKLDLSNVQSKCGSKDNIKHVPGGGSVQIVYK PVDLSKVTSKCGSLGNIHHKPGGGQVEVKSEKLDF KDRVQSKIGSLDNITHVPGGGNKKIETHKLTFRENA KAKTDHGAEIVYKSPVVSGDTSPRHLSNVSSTGSID MVDSPQLATLADEVSASLAKQGL |
| Tau 4R0N | SEQ ID N° : 8 | MAEPRQEFEVMEDHAGTYGLGDRKDQGGYTMHQ DQEGDTDAGLKAEEAGIGDTPSLEDEAAGHVTQA RMVSKSKDGTGSDDKKAKGADGKTKIATPRGAAP PGQKGQANATRIPAKTPPAPKTPPSSGEPPKSGDRS GYSSPGSPGTPGSRSRTPSLPTPPTREPKKVAVVRTP PKSPSSAKSRLQTAPVPMPDLKNVKSKIGSTENLKH QPGGGKVQIINKKLDLSNVQSKCGSKDNIKHVPG GGSVQIVYKPVDLSKVTSKCGSLGNIHHKPGGGQV EVKSEKLDFKDRVQSKIGSLDNITHVPGGGNKKIET HKLTFRENAKAKTDHGAEIVYKSPVVSGDTSPRHL SNVSSTGSIDMVDSPQLATLADEVSASLAKQGL |
| mTau 4R2N | SEQ ID N° : 9 | MADPRQEFDTMEDHAGDYTLLQDQEGDMDHGLK ESPPQPPADDGAEEPGSETSDAKSTPTAEDVTAPLV |

Cont. Fig. 1

| | | |
|---|---|---|
| | | DERAPDKQAAAQPHTEIPEGITAEEAGIGDTPNQED QAAGHVTQARVASKDRTGNDEKKAKGADGKTGA KIATPRGAASPAQKGTSNATRIPAKTTPSPKTPPGSG EPPKSGERSGYSSPGSPGTPGSRSRTPSLPTPPTREPK KVAVVRTPPKSPSASKSRLQTAPVPMPDLKNVRSKI GSTENLKHQPGGGKVQIINKKLDLSNVQSKCGSK DNIKHVPGGGSVQIVYKPVDLSKVTSKCGSLGNIH HKPGGGQVEVKSEKLDFKDRVQSKIGSLDNITHVP GGGNKKIETHKLTFRENAKAKTDHGAEIVYKSPVV SGDTSPRHLSNVSSTGSIDMVDSPQLATLADEVSAS LAKQGL |
| mTau 4R0N | SEQ ID N° : 10 | MADPRQEFDTMEDHAGDYTLLQDQEGDMDHGLK AEEAGIGDTPNQEDQAAGHVTQARVASKDRTGND EKKAKGADGKTGAKIATPRGAASPAQKGTSNATRI PAKTTPSPKTPPGSGEPPKSGERSGYSSPGSPGTPGS RSRTPSLPTPPTREPKKVAVVRTPPKSPSASKSRLQT APVPMPDLKNVRSKIGSTENLKHQPGGGKVQIINK KLDLSNVQSKCGSKDNIKHVPGGGSVQIVYKPVD LSKVTSKCGSLGNIHHKPGGGQVEVKSEKLDFKDR VQSKIGSLDNITHVPGGGNKKIETHKLTFRENAKAK TDHGAEIVYKSPVVSGDTSPRHLSNVSSTGSIDMVD SPQLATLADEVSASLAKQGL |
| PHF6* | SEQ ID N° : 11 | VKIINK |

Figure 2
a. SEQ ID N° : 1
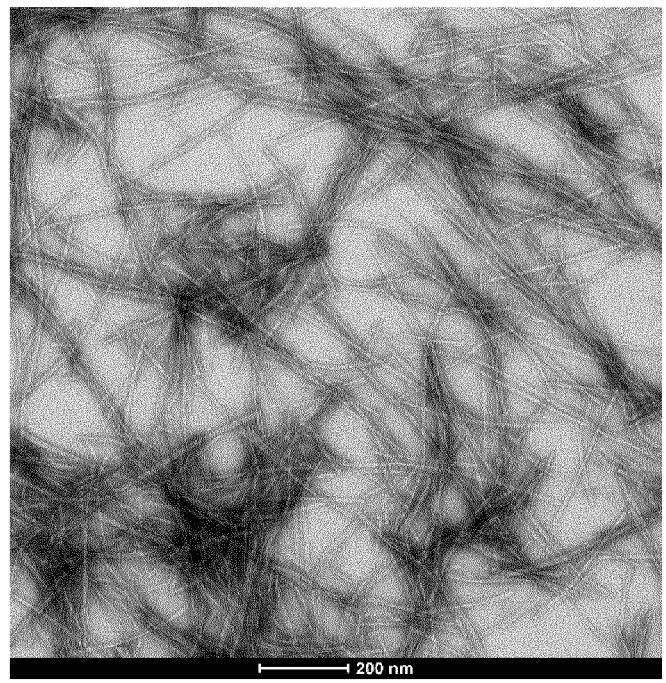
b.
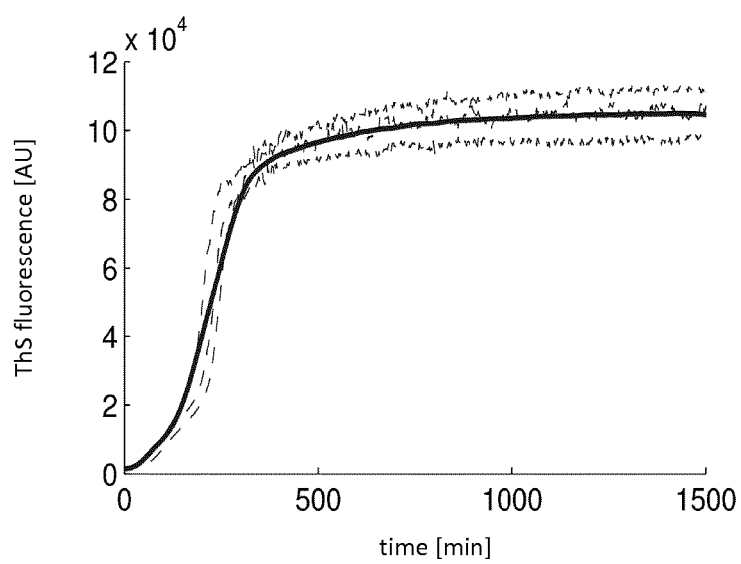

Figure 2
c.
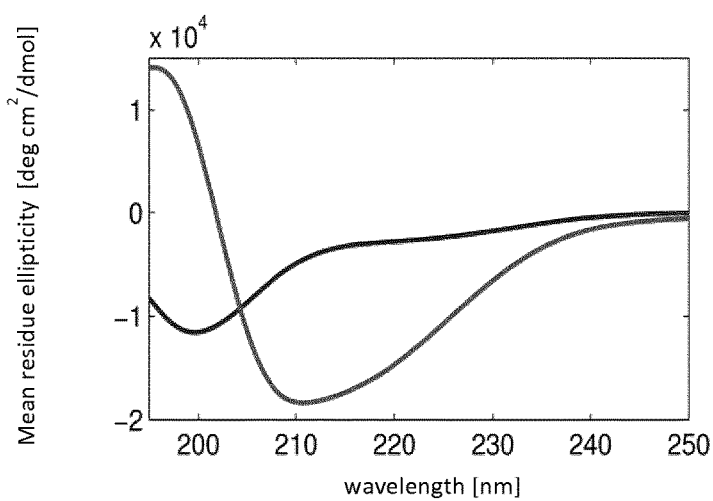
d.
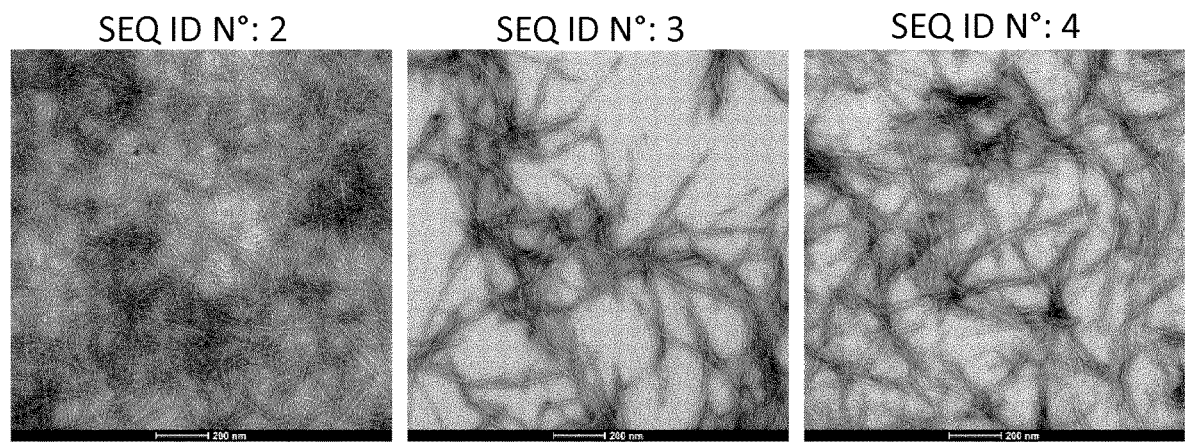
SEQ ID N°: 2     SEQ ID N°: 3     SEQ ID N°: 4

Figure 3
a.
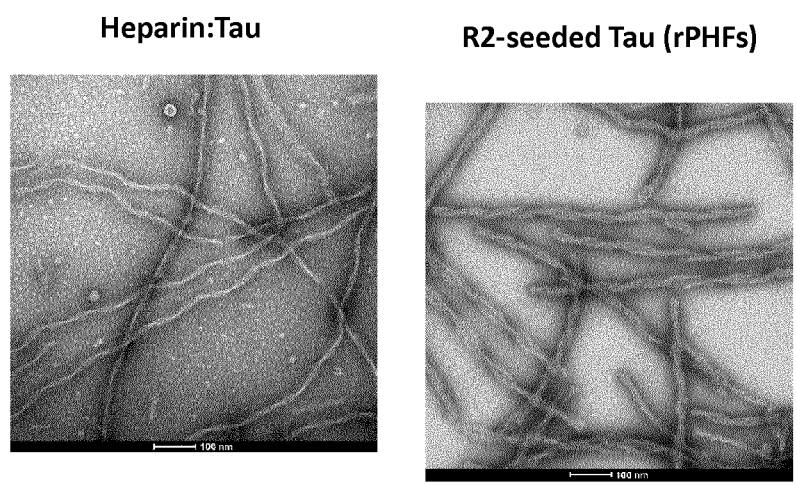
b.
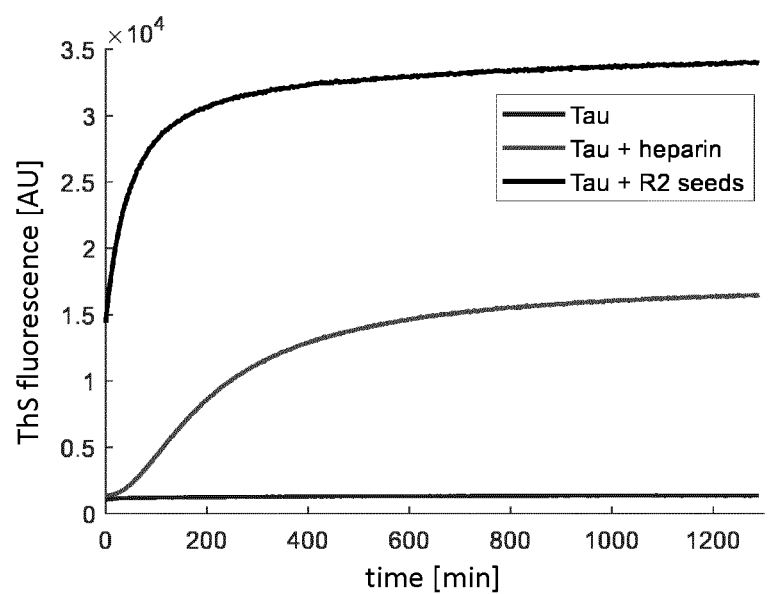

c.

d.

Figure 5
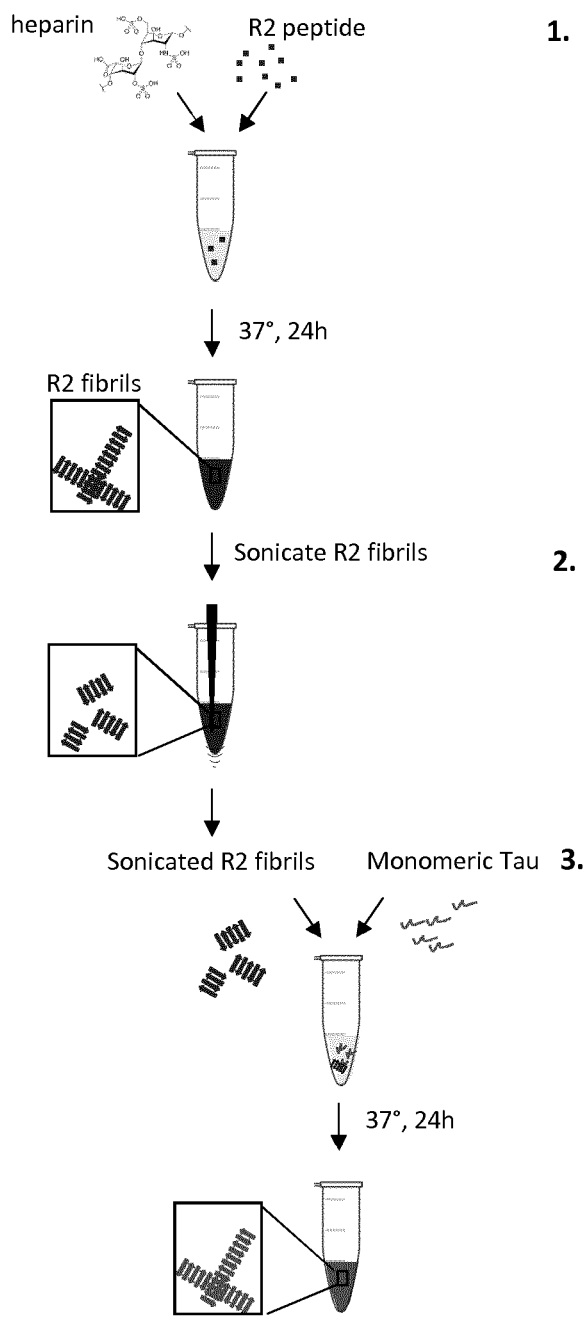
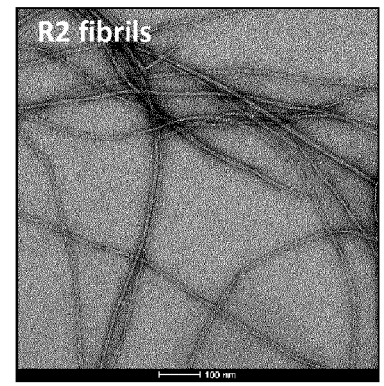
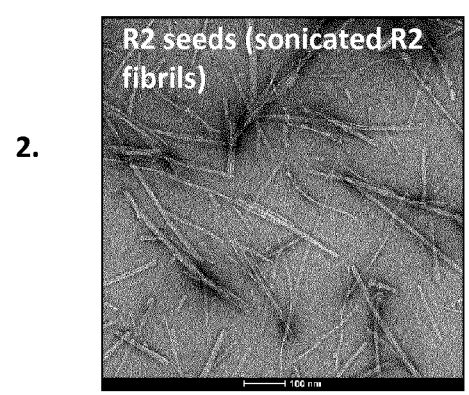
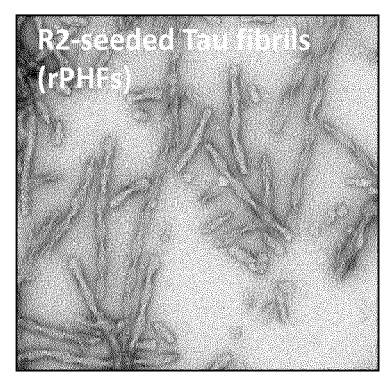

Figure 6
b.
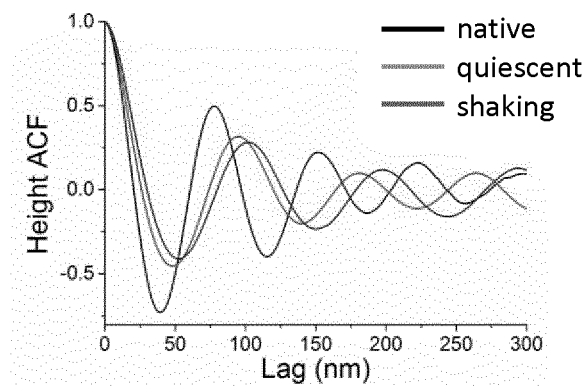
c.
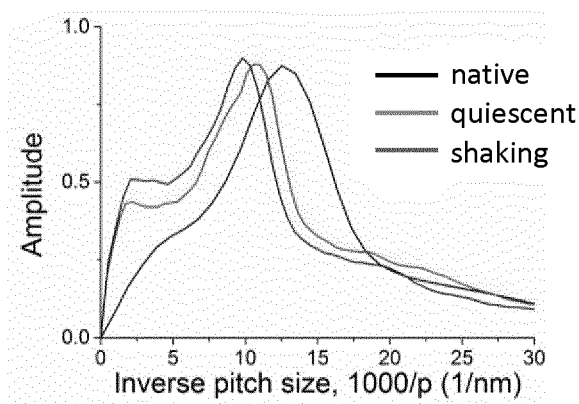
d.
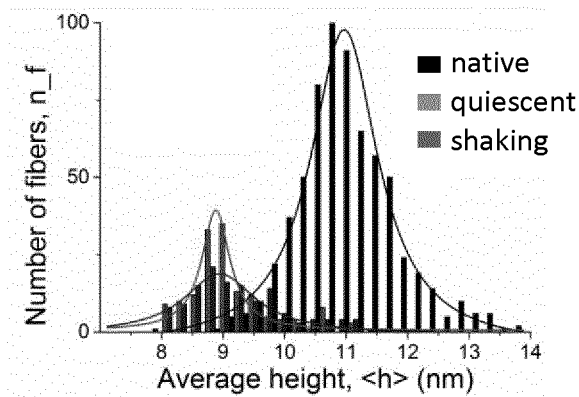

Figure 6
e.
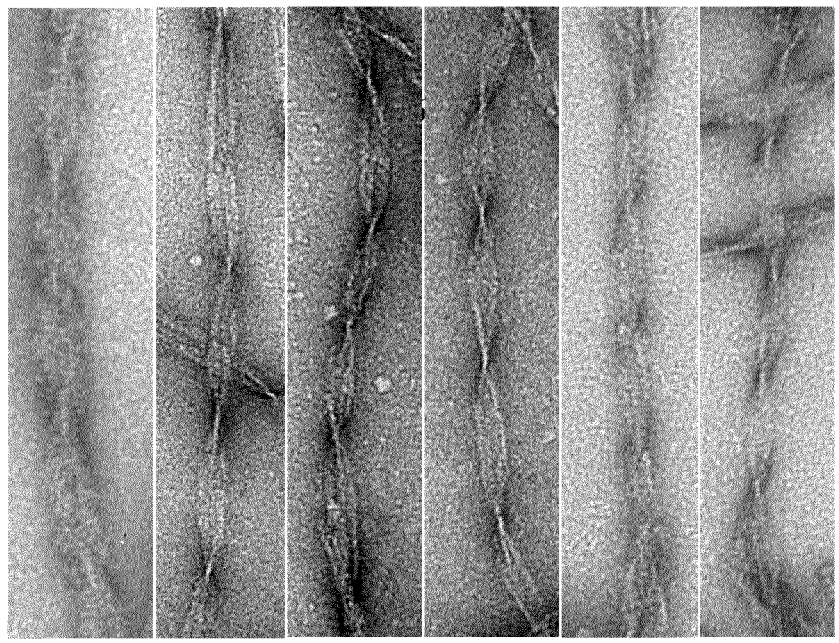
f.
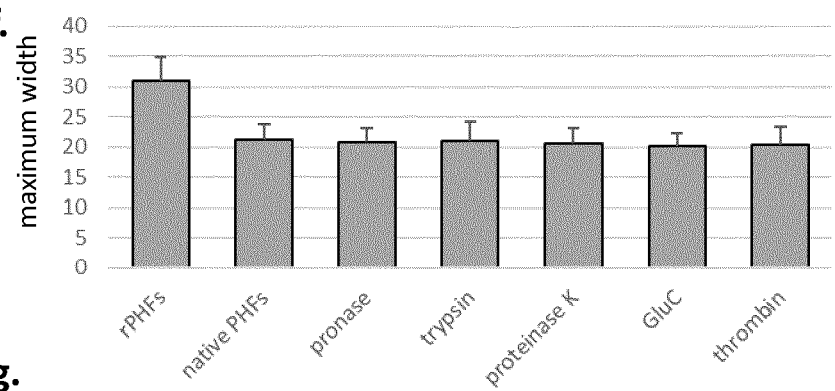
g.
|  | Native PHFs | rPHFs | Digested rPHFs |
|---|---|---|---|
| periodicity | ~ 80 [nm] | ~ 90-100 [nm] | N.A. |
| height | ~ 11 [nm] | ~ 9 [nm] | N.A. |
| max. width | ~ 20 [nm] | ~ 30 [nm] | ~ 20 [nm] |

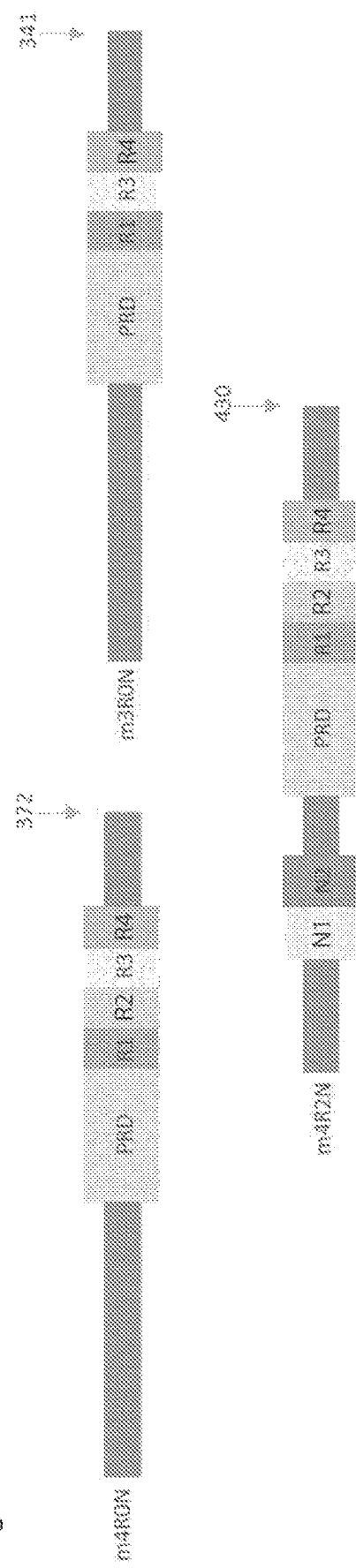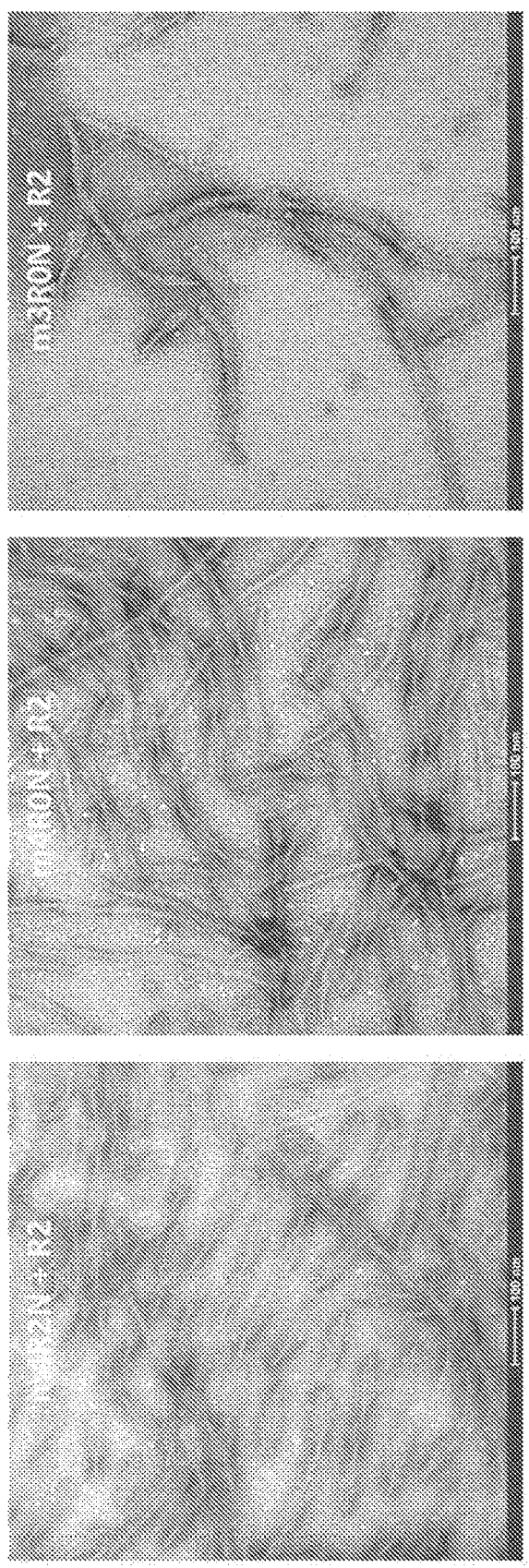
Fig. 9A
Fig. 9B

Fig. 9C

Fig. 16C
R2-seeded Tau
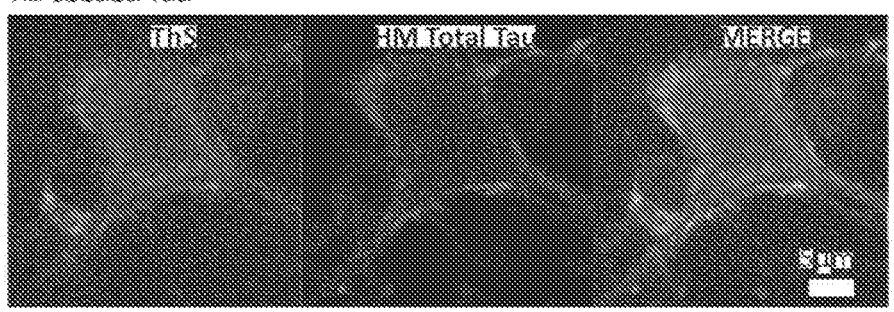
R2-seeded K18
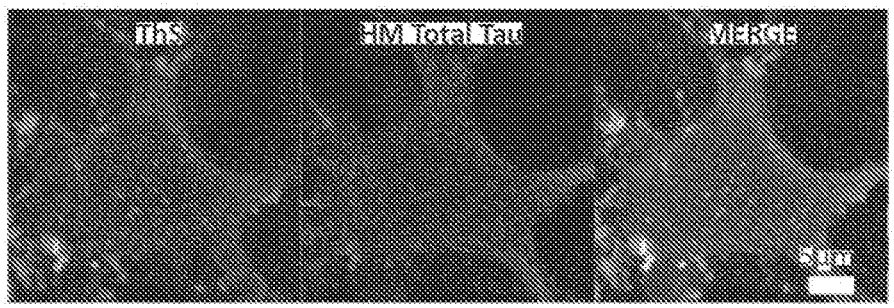

Fig. 17C
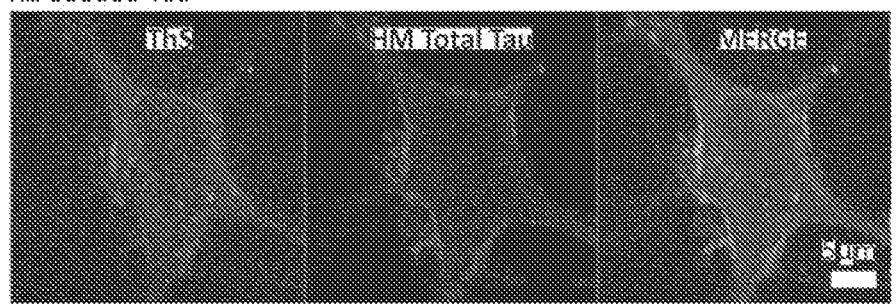
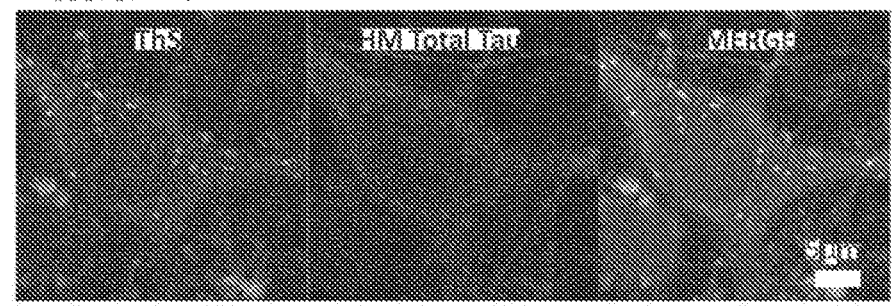

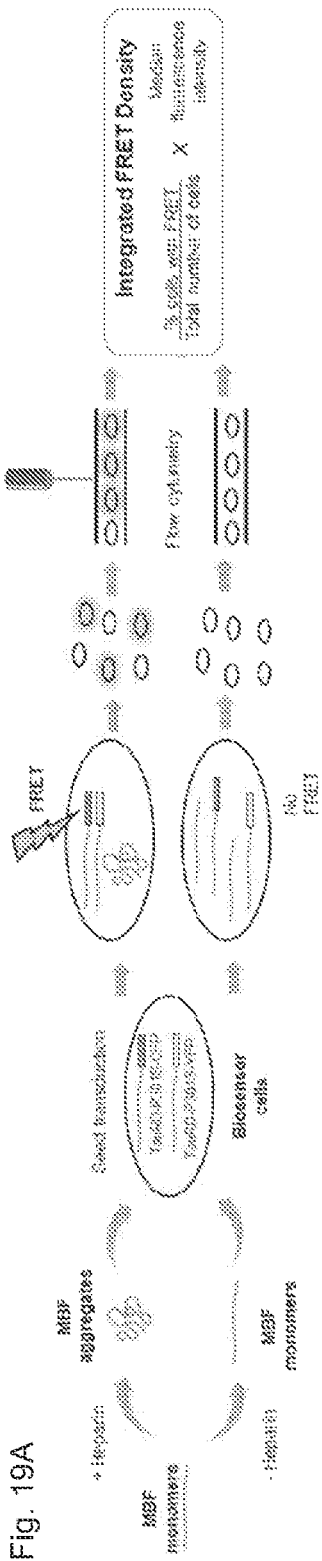
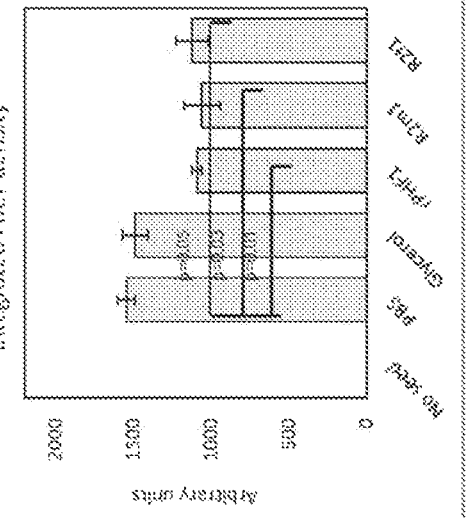
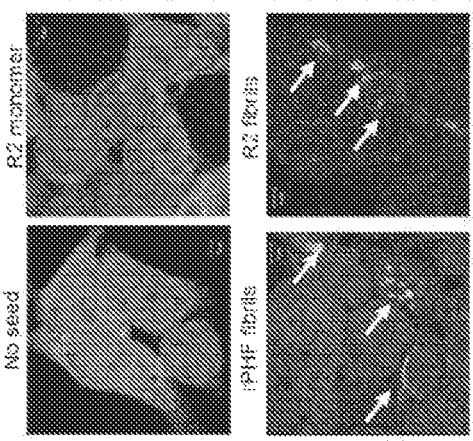
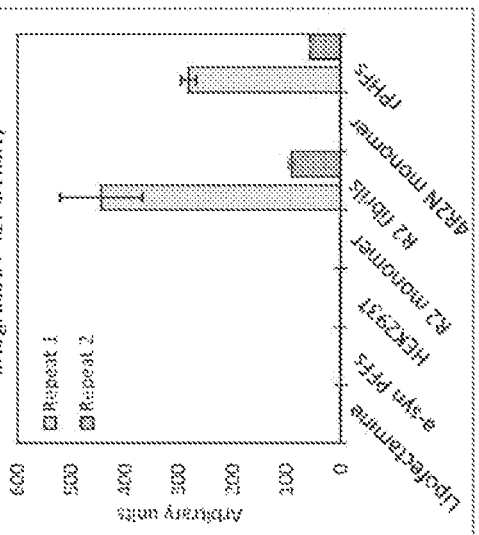

Fig. 22A Tau monomer
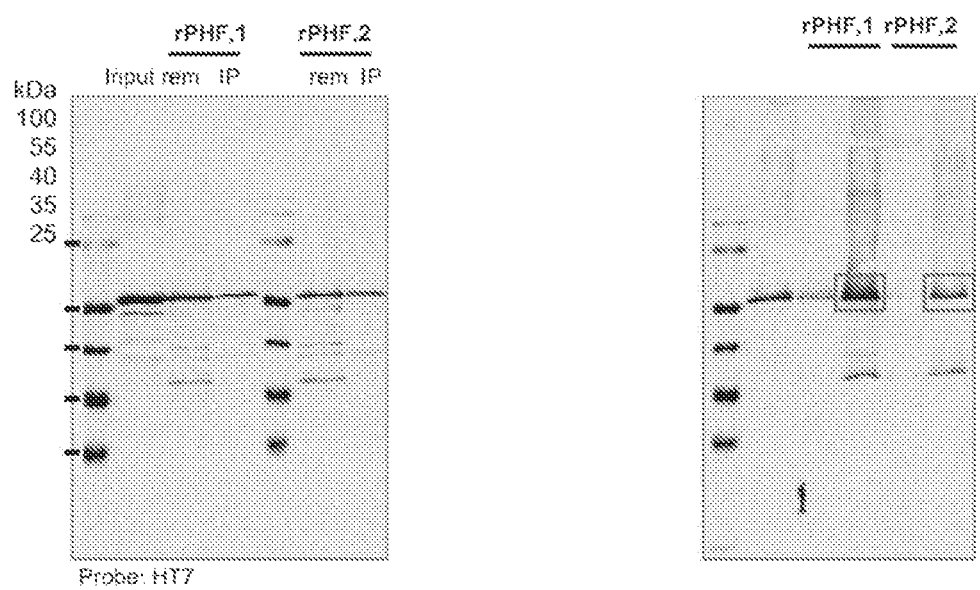
Fig. 22B
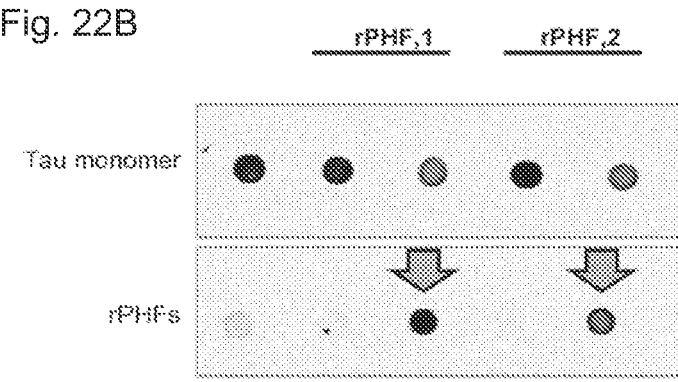

SEQUENCE LISTING

```
<160> NUMBER OF SEQ ID NOS: 20

<210> SEQ ID NO 1
<211> LENGTH: 26
<212> TYPE: PRT
<213> ORGANISM: Homo sapiens

<400> SEQUENCE: 1

Val Gln Ile Ile Asn Lys Lys Leu Asp Leu Ser Asn Val Gln Ser Lys
1               5                   10                  15

Cys Gly Ser Lys Asp Asn Ile Lys His Val
            20                  25

<210> SEQ ID NO 2
<211> LENGTH: 57
<212> TYPE: PRT
<213> ORGANISM: Homo sapiens
```

```
<400> SEQUENCE: 2

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys Val
            20                  25                  30

Gln Ile Ile Asn Lys Lys Leu Asp Leu Ser Asn Val Gln Ser Lys Cys
        35                  40                  45

Gly Ser Lys Asp Asn Ile Lys His Val
    50                  55

<210> SEQ ID NO 3
<211> LENGTH: 30
<212> TYPE: PRT
<213> ORGANISM: Homo sapiens

<400> SEQUENCE: 3

Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly
            20                  25                  30

<210> SEQ ID NO 4
<211> LENGTH: 30
<212> TYPE: PRT
<213> ORGANISM: Homo sapiens

<400> SEQUENCE: 4

Val Gln Ile Ile Asn Lys Lys Leu Asp Leu Ser Asn Val Gln Ser Lys
1               5                   10                  15

Cys Gly Ser Lys Asp Asn Ile Lys His Val Ser Gly Gly Gly
            20                  25                  30

<210> SEQ ID NO 5
<211> LENGTH: 441
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160
```

```
Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 6
<211> LENGTH: 129
<212> TYPE: PRT
<213> ORGANISM: Artificial Sequence
<220> FEATURE:
<223> OTHER INFORMATION: synthetic peptide

<400> SEQUENCE: 6

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys Val
            20                  25                  30

Gln Ile Ile Asn Lys Lys Leu Asp Leu Ser Asn Val Gln Ser Lys Cys
        35                  40                  45

Gly Ser Lys Asp Asn Ile Lys His Val Pro Gly Gly Gly Ser Val Gln
    50                  55                  60

Ile Val Tyr Lys Pro Val Asp Leu Ser Lys Val Thr Ser Lys Cys Gly
65                  70                  75                  80
```

Ser Leu Gly Asn Ile His His Lys Pro Gly Gly Gln Val Glu Val
            85                  90                  95

Lys Ser Glu Lys Leu Asp Phe Lys Asp Arg Val Gln Ser Lys Ile Gly
            100                 105                 110

Ser Leu Asp Asn Ile Thr His Val Pro Gly Gly Asn Lys Lys Ile
            115                 120                 125

Glu

<210> SEQ ID NO 7
<211> LENGTH: 412
<212> TYPE: PRT
<213> ORGANISM: Homo sapiens

<400> SEQUENCE: 7

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

```
Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 8
<211> LENGTH: 383
<212> TYPE: PRT
<213> ORGANISM: Homo sapiens

<400> SEQUENCE: 8

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270
```

```
Lys Pro Gly Gly Gln Val Glu Val Lys Ser Glu Lys Leu Asp Phe
            275                 280                 285

Lys Asp Arg Val Gln Ser Lys Ile Gly Ser Leu Asp Asn Ile Thr His
    290                 295                 300

Val Pro Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
            355                 360                 365

Thr Leu Ala Asp Glu Val Ser Ala Ser Leu Ala Lys Gln Gly Leu
    370                 375                 380
```

<210> SEQ ID NO 9
<211> LENGTH: 430
<212> TYPE: PRT
<213> ORGANISM: Artificial Sequence
<220> FEATURE:
<223> OTHER INFORMATION: synthetic peptide

<400> SEQUENCE: 9

```
Met Ala Asp Pro Arg Gln Glu Phe Asp Thr Met Glu Asp His Ala Gly
1               5                   10                  15

Asp Tyr Thr Leu Leu Gln Asp Gln Glu Gly Asp Met Asp His Gly Leu
            20                  25                  30

Lys Glu Ser Pro Pro Gln Pro Pro Ala Asp Asp Gly Ala Glu Glu Pro
        35                  40                  45

Gly Ser Glu Thr Ser Asp Ala Lys Ser Thr Pro Thr Ala Glu Asp Val
    50                  55                  60

Thr Ala Pro Leu Val Asp Glu Arg Ala Pro Asp Lys Gln Ala Ala Ala
65                  70                  75                  80

Gln Pro His Thr Glu Ile Pro Glu Gly Ile Thr Ala Glu Glu Ala Gly
                85                  90                  95

Ile Gly Asp Thr Pro Asn Gln Glu Asp Gln Ala Ala Gly His Val Thr
            100                 105                 110

Gln Ala Arg Val Ala Ser Lys Asp Arg Thr Gly Asn Asp Glu Lys Lys
        115                 120                 125

Ala Lys Gly Ala Asp Gly Lys Thr Gly Ala Lys Ile Ala Thr Pro Arg
    130                 135                 140

Gly Ala Ala Ser Pro Ala Gln Lys Gly Thr Ser Asn Ala Thr Arg Ile
145                 150                 155                 160

Pro Ala Lys Thr Thr Pro Ser Pro Lys Thr Pro Pro Gly Ser Gly Glu
                165                 170                 175

Pro Pro Lys Ser Gly Glu Arg Ser Gly Tyr Ser Ser Pro Gly Ser Pro
            180                 185                 190

Gly Thr Pro Gly Ser Arg Ser Arg Thr Pro Ser Leu Pro Thr Pro Pro
        195                 200                 205

Thr Arg Glu Pro Lys Lys Val Ala Val Val Arg Thr Pro Pro Lys Ser
    210                 215                 220

Pro Ser Ala Ser Lys Ser Arg Leu Gln Thr Ala Pro Val Pro Met Pro
225                 230                 235                 240

Asp Leu Lys Asn Val Arg Ser Lys Ile Gly Ser Thr Glu Asn Leu Lys
                245                 250                 255
```

His Gln Pro Gly Gly Gly Lys Val Gln Ile Ile Asn Lys Lys Leu Asp
                260                 265                 270

Leu Ser Asn Val Gln Ser Lys Cys Gly Ser Lys Asp Asn Ile Lys His
            275                 280                 285

Val Pro Gly Gly Gly Ser Val Gln Ile Val Tyr Lys Pro Val Asp Leu
        290                 295                 300

Ser Lys Val Thr Ser Lys Cys Gly Ser Leu Gly Asn Ile His His Lys
305                 310                 315                 320

Pro Gly Gly Gly Gln Val Glu Val Lys Ser Glu Lys Leu Asp Phe Lys
                325                 330                 335

Asp Arg Val Gln Ser Lys Ile Gly Ser Leu Asp Asn Ile Thr His Val
            340                 345                 350

Pro Gly Gly Gly Asn Lys Lys Ile Glu Thr His Lys Leu Thr Phe Arg
        355                 360                 365

Glu Asn Ala Lys Ala Lys Thr Asp His Gly Ala Glu Ile Val Tyr Lys
    370                 375                 380

Ser Pro Val Val Ser Gly Asp Thr Ser Pro Arg His Leu Ser Asn Val
385                 390                 395                 400

Ser Ser Thr Gly Ser Ile Asp Met Val Asp Ser Pro Gln Leu Ala Thr
                405                 410                 415

Leu Ala Asp Glu Val Ser Ala Ser Leu Ala Lys Gln Gly Leu
            420                 425                 430

<210> SEQ ID NO 10
<211> LENGTH: 372
<212> TYPE: PRT
<213> ORGANISM: Artificial Sequence
<220> FEATURE:
<223> OTHER INFORMATION: synthetic peptide

<400> SEQUENCE: 10

Met Ala Asp Pro Arg Gln Glu Phe Asp Thr Met Glu Asp His Ala Gly
1               5                   10                  15

Asp Tyr Thr Leu Leu Gln Asp Gln Glu Gly Asp Met Asp His Gly Leu
            20                  25                  30

Lys Ala Glu Glu Ala Gly Ile Gly Asp Thr Pro Asn Gln Glu Asp Gln
        35                  40                  45

Ala Ala Gly His Val Thr Gln Ala Arg Val Ala Ser Lys Asp Arg Thr
    50                  55                  60

Gly Asn Asp Glu Lys Lys Ala Lys Gly Ala Asp Gly Lys Thr Gly Ala
65                  70                  75                  80

Lys Ile Ala Thr Pro Arg Gly Ala Ala Ser Pro Ala Gln Lys Gly Thr
                85                  90                  95

Ser Asn Ala Thr Arg Ile Pro Ala Lys Thr Thr Pro Ser Pro Lys Thr
            100                 105                 110

Pro Pro Gly Ser Gly Glu Pro Lys Ser Gly Glu Arg Ser Gly Tyr
        115                 120                 125

Ser Ser Pro Gly Ser Pro Gly Thr Pro Gly Ser Arg Ser Arg Thr Pro
    130                 135                 140

Ser Leu Pro Thr Pro Pro Thr Arg Glu Pro Lys Lys Val Ala Val Val
145                 150                 155                 160

Arg Thr Pro Pro Lys Ser Pro Ser Ala Ser Lys Ser Arg Leu Gln Thr
                165                 170                 175

Ala Pro Val Pro Met Pro Asp Leu Lys Asn Val Arg Ser Lys Ile Gly
            180                 185                 190

-continued

Ser Thr Glu Asn Leu Lys His Gln Pro Gly Gly Gly Lys Val Gln Ile
        195                 200                 205

Ile Asn Lys Lys Leu Asp Leu Ser Asn Val Gln Ser Lys Cys Gly Ser
    210                 215                 220

Lys Asp Asn Ile Lys His Val Pro Gly Gly Ser Val Gln Ile Val
225                 230                 235                 240

Tyr Lys Pro Val Asp Leu Ser Lys Val Thr Ser Lys Cys Gly Ser Leu
            245                 250                 255

Gly Asn Ile His His Lys Pro Gly Gly Gln Val Glu Val Lys Ser
            260                 265                 270

Glu Lys Leu Asp Phe Lys Asp Arg Val Gln Ser Lys Ile Gly Ser Leu
        275                 280                 285

Asp Asn Ile Thr His Val Pro Gly Gly Asn Lys Lys Ile Glu Thr
    290                 295                 300

His Lys Leu Thr Phe Arg Glu Asn Ala Lys Ala Lys Thr Asp His Gly
305                 310                 315                 320

Ala Glu Ile Val Tyr Lys Ser Pro Val Val Ser Gly Asp Thr Ser Pro
                325                 330                 335

Arg His Leu Ser Asn Val Ser Ser Thr Gly Ser Ile Asp Met Val Asp
            340                 345                 350

Ser Pro Gln Leu Ala Thr Leu Ala Asp Glu Val Ser Ala Ser Leu Ala
        355                 360                 365

Lys Gln Gly Leu
    370

<210> SEQ ID NO 11
<211> LENGTH: 6
<212> TYPE: PRT
<213> ORGANISM: Artificial Sequence
<220> FEATURE:
<223> OTHER INFORMATION: synthetic peptide

<400> SEQUENCE: 11

Val Lys Ile Ile Asn Lys
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic peptide

<400> SEQUENCE: 12

Pro Pro Gly Gln Lys
1               5

<210> SEQ ID NO 13
<211> LENGTH: 20
<212> TYPE: PRT
<213> ORGANISM: Artificial Sequence
<220> FEATURE:
<223> OTHER INFORMATION: synthetic peptide

<400> SEQUENCE: 13

Lys Leu Asp Leu Ser Asn Val Gln Ser Lys Cys Gly Ser Lys Asp Asn
1               5                   10                  15

Ile Lys His Val
            20

<210> SEQ ID NO 14
<211> LENGTH: 17
<212> TYPE: PRT
<213> ORGANISM: Artificial Sequence
<220> FEATURE:
<223> OTHER INFORMATION: synthetic peptide

<400> SEQUENCE: 14

Val Gln Ile Ile Asn Lys Lys Leu Asp Leu Ser Asn Val Gln Ser Lys
1               5                   10                  15

Cys

<210> SEQ ID NO 15
<211> LENGTH: 11
<212> TYPE: PRT
<213> ORGANISM: Artificial Sequence
<220> FEATURE:
<223> OTHER INFORMATION: synthetic peptide

<400> SEQUENCE: 15

Val Gln Ile Ile Asn Lys Lys Leu Asp Leu Ser
1               5                   10

<210> SEQ ID NO 16
<211> LENGTH: 16
<212> TYPE: PRT
<213> ORGANISM: Artificial Sequence
<220> FEATURE:
<223> OTHER INFORMATION: synthetic peptide

<400> SEQUENCE: 16

Val Gln Ile Ile Asn Lys Lys Leu Asp Leu Ser Asn Val Gln Ser Lys
1               5                   10                  15

<210> SEQ ID NO 17
<211> LENGTH: 11
<212> TYPE: PRT
<213> ORGANISM: Artificial Sequence
<220> FEATURE:
<223> OTHER INFORMATION: synthetic peptide

<400> SEQUENCE: 17

Val Gln Ile Ile Asn Asn Lys Leu Asp Leu Ser
1               5                   10

<210> SEQ ID NO 18
<211> LENGTH: 11
<212> TYPE: PRT
<213> ORGANISM: Artificial Sequence
<220> FEATURE:
<223> OTHER INFORMATION: synthetic peptide

<400> SEQUENCE: 18

Val Gln Ile Ile Asn Lys Asn Leu Asp Leu Ser
1               5                   10

<210> SEQ ID NO 19
<211> LENGTH: 57
<212> TYPE: PRT
<213> ORGANISM: Artificial Sequence
<220> FEATURE:
<223> OTHER INFORMATION: synthetic peptide

<400> SEQUENCE: 19

Val Gln Ile Ile Asn Lys Leu Asp Leu Ser Asn Val Gln Ser Lys
1               5                   10                  15

```
Cys Gly Ser Lys Asp Asn Ile Lys His Val Pro Gly Gly Gly Ser Val
            20              25              30

Gln Ile Val Tyr Lys Pro Val Asp Leu Ser Lys Val Thr Ser Lys Cys
            35              40              45

Gly Ser Leu Gly Asn Ile His His Lys
    50              55

<210> SEQ ID NO 20
<211> LENGTH: 25
<212> TYPE: PRT
<213> ORGANISM: Artificial Sequence
<220> FEATURE:
<223> OTHER INFORMATION: synthetic peptide

<400> SEQUENCE: 20

Val Gln Ile Ile Asn Lys Leu Asp Leu Ser Asn Val Gln Ser Lys Cys
1               5                   10                  15

Gly Ser Lys Asp Asn Ile Lys His Val
            20              25
```

METHOD FOR PREPARING PHFS-LIKE TAU AGGREGATES

PRIORITY STATEMENT

This application is a national stage application under 35 U.S.C. § 371 of PCT International Application No. PCT/EP2019/060969, which has an international filing date of 29 Apr. 2019 and claims priority under 35 U.S.C. § 119 to European Patent Application No. 18169898.6 filed on 27 Apr. 2018. The contents of each application recited above are incorporated herein by reference in their entirety.

FIELD OF THE INVENTION

The invention relates to a method for preparing PHFs-like Tau aggregates and to a method for identifying compounds that are inhibitors of Tau protein aggregation, blockers of Tau seeding and propagation, and imaging agents that specifically bind PHF.

BACKGROUND OF THE INVENTION

Alzheimer's disease (AD) is defined by two pathological hallmarks that primarily contain two different proteins: extracellular plaques composed of amyloid β peptide (Aβ) and intracellular neurofibrillary tangles (NFTs) composed of the microtubule-associated protein Tau filaments, the paired-helical filaments (PHFs). Despite the fact that no Tau mutations have been linked with AD, several mutations in Aβ precursor gene APP and in the enzymes involved in its processing and generation of Aβ, namely presenilin 1 and 2, have been linked to inherited early onset forms of AD. This firm genetic evidence, combined with the identification of Aβ as the primary component of amyloid plaques gave rise to the amyloid hypothesis, which suggests that Aβ production and plaque formation are the primary cause of AD. In this model, Aβ aggregation represents the earliest sequel in the pathogenesis of AD; the subsequent deleterious interactions of Aβ plaques with signaling pathways were thought to lead to aberrant phosphorylation of Tau, which in turn triggers its disassociation from microtubules and aggregation. The amyloid hypothesis suggests that clinical intervention aiming to reduce the Aβ load should ameliorate cognitive decline and reduce neuropathological deposits. However, none of the dozens of clinical trials using immunotherapies against Aβ plaques have succeeded to slow down, reverse or even slightly alter the clinical course of the disease. Even the most promising clinical trial, which has achieved complete amyloid plaques removal from AD patients' brains, has failed to alleviate the progressive neurodegeneration and cognitive decline. Even though this might be due to the fact that, despite pathological species building up over decades without any clinical symptoms, most trials were designed to treat symptomatic AD, at a time when the pathology might have been too advanced to be reversed, these failures have tempered the Aβ-centric view of AD. Alternatively, this could be explained by the fact that multiple parallel pathways underpin the pathogenesis of AD. In fact, total Tau levels are increased in AD compared to controls and phosphorylated Tau levels (at S231 and S181) correlate with cognitive decline and with NFT-pathology in AD.

Additionally, both total and phosphorylated CSF Tau can predict the AD cognitive decline. Similarly, NFT load correlates well with neurodegeneration and disease progression in AD and several central nervous system disorders such as Pick's disease, progressive supranuclearplasy and fronto-temporal dementias that are also characterized by Tau inclusions, with no implication of Aβ. These observations suggest that Tau aggregates may play a critical role in symptomatology and pathology progression of AD. Moreover, point mutations have been identified in Tau, resulting in hereditary Tauopathies and indicating that Tau can, by itself, cause neurodegeneration, thereby strengthening the hypothesis that Tau is a key player in AD pathology. These conclusions, combined with the continuous failures of clinical trials based on targeting amyloid plaques, have led to the recent renewed interest in Tau as a viable target for the treatment of AD.

AD is becoming a major public health problem due to our aging population and thereby a great health-care challenge of the 21st century. It is a terrible burden for patients, their families, and caregivers. Despite more than one century of scientific exploration aimed at unraveling the mechanisms underlying AD onset and progression and more than two decades of clinical trials, AD remains a fatal global epidemic, whose causes and pathological mechanisms are still largely unknown, and for which no treatment has been found to efficiently prevent, cure or even slower the progression.

In the central nervous system, Tau occurs in six isoforms depending on the alternative splicing of exons E2, E3 and E10, giving rise to the variants containing either 0, 1 or 2 amino-terminal inserts (0N, 1N and 2N), and 3 or 4 microtubules binding repeats, MTBRs, (3R- and 4R-Tau), named R1, R2, R3 and R4 (FIG. 1 a). At the structural level, Tau is characterized by a low content of transient α-helix, β-sheet or polyproline helix II, as demonstrated by nuclear magnetic resonance (NMR). Given its highly soluble and disordered state, Tau fibrilization seems counterintuitive. In vitro, the addition of polyanions, such as heparin, RNA, fatty acid micelles or negatively charged surfaces is necessary to induce full length Tau aggregation. This is most likely driven by charge compensation of the basic part of Tau, whereby the polyanionic compound binds to extended form of the protein, favoring its conversion into β-sheets, thus overcoming the nucleation barrier. Moreover, Tau contains several short stretches of amino acid that present a high propensity to fold into β-sheets, notably the first 8-10 amino acid of the repeat peptides R2 to R4. In fact, two hexapeptides at the beginning of R2 and R3, named PHF6* and PHF6, are able to fibrilize as such and have been shown to be critical nucleating sequences of Tau. Several longer fragments of Tau also show a higher propensity to aggregate compare to the full length protein, and various peptide that include the PHF6 sequence have been shown to rapidly aggregate even in the absence of any inducer.

The normal function of Tau depends on the precise ratio between the different isoforms. For instance, the presence of both N-terminal inserts and exon 10 (i.e. R2) enhances Tau binding to tubulin. In healthy adult individuals, the ratios of N-terminal inserts 1N:0N:2N are 54:37:9, and the ratio of 4R:3R isoforms is 1:1. In diseased brains, the 4R:3R ratio is altered: it increases or decreases depending on the disease or disease-linked mutations. Several mutations around the exon 10 region result in an imbalance of 3R- and 4R-Tau isoforms and are associated with inherited forms of FTDP-17, suggesting that failure in exon 10 splicing regulation could contribute to the pathogenesis of some Tauopathies. In fact, intronic mutations of some cases of FTDP-17 resulting in altered splicing of Tau mRNA and favoring the 4R isoforms have been causally associated with the disease. Conversely, both in Pick disease and in Down syndrome, the 3R:4R Tau isoforms ratio is amplified. In these cases, the pathology could arise from the fact that 3R-Tau MT binding capacity is lower than that of the 4R-Tau, hence leading to an increase in free Tau, which may be more prone to abnormal hyperphosphorylation. Remarkably, the ratio 4R:3R Tau is diminished during development, suggesting that the different isoforms could have specific roles in neurogenesis, and that these processes could be aberrantly reactivated in the course of AD. Indeed, in human fetal brain, only the shortest Tau isoform (0N3R) is expressed and is highly phosphorylated. The shift in isoform expression and phosphorylation observed in adults coincides with synaptogenesis and the appearance of stable MTs, suggesting that Tau isoform-specific phosphorylation plays a role in synapse formation and synaptic plasticity. In fact, 3R-Tau binds less to MTs compared to the 4R isoforms. Therefore, the exclusive occurrence of 3R isoforms in the fetal brains suggests that it could be involved in the higher plasticity observed during neuronal development.

Elucidating the molecular basis of Tau aggregation has been hampered by the protein size, number of splicing isoforms and its large and heterogeneous post-translational modification (PTM) pattern. Although it remains a mystery why this protein aggregates into PHFs, many reports over the last three decades have described key structural and biochemical features of Tau filaments, such as the core of PHFs and their "fuzzy coat". Indeed, Tau fibrils can be viewed as a soft polymer brush composed of a rigid pronase-resistant core and a flexible fuzzy coat. The pronase-resistant core of the PHFs was first identified from the digestion of PHFs isolated from AD brain, and consisted in the microtubule binding domain. Gold immunolabelling experiments demonstrated that the microtubule biding region in the PHFs is largely inaccessible, deeply buried in the core of the PHFs, and becomes exposed upon extensive digestion. Atomic Force Microscopy (AFM) revealed that Tau fibrils present a ≈16-nm-thick fuzzy coat that resembles a two-layered polyelectrolyte brush, which is formed by the unstructured short C-terminal and long N-terminal Tau domains. Most recently, the atomic structure of native PHFs and straight filament (SF) has been revealed by cryo electron microscopy (cryo-EM). The 3.4-3.5 Å resolution map and derived atomic model demonstrate that the PHFs core is made of two identical protofilaments comprising residues V306-F378 which contain the entire R3 and R4 repeat domains, plus an additional 10 amino acids C-terminal to the repeats, while the repeat peptide R1 and R2 were absent from the core structure. More precisely, the core of the PHFs is composed of eight β-sheets (spanning the sequence V306-F378) that run along the length of the protofilament, adopting a C-shaped architecture. Two C-shaped structures, each formed by a molecule of Tau, bind together to form individual rungs along the filament. In PHFs, the two Cs are arranged symmetrically, while in SFs, these Cs are arranged in a slightly off-kilter configuration. These results are in line with previous studies using N-terminal sequencing which reported the presence of a mixture of peptides (~90-100 residues) in the core of the PHFs, encompassing either R1-R3-R4 from 3R Tau (N-terminus: H268 or L266) and R2-R3-R4 (N-terminus: H299 or 1297) or R1-R2-R3 in 4R Tau (N-terminus: H268 or L266). These peptides appear to be terminated at Glu391, a cleavage site that was confirmed in isolated PHFs and in AD tissues using an antibody specific to this cleavage site, suggesting that the core of the PHFs might extend even beyond the F378 reported by Fitzpatrick et al.

The PHFs are the main component of the NFTs found inside the neurons of AD patients. PHFs have also been observed in several other neurodegenerative diseases, such as corticobasal degeneration (CBD), progressive supranuclear palsy (PSP), Pick's disease (PiD), argyrophilic grain disease (AGD), chronic traumatic encephalopathy (CET) and frontotemporal dementia with parkinsonism linked to chromosome 17 (FTDP-17). These diverse pathologies are characterized by distinct Tau filament structures, isoform compositions, and regional and cellular distributions. In AD, Tau fibrils form mainly left-handed PHFs with alternating loops around 20 nm wide, with a crossover of around 8 nm wide, and a half-periodicity around of 80 nm, presenting a skew distribution toward longer periodicity values, which suggests the ability of the fibrils to untwist. In CBD, the PHFs are slightly wider, present a half-periodicity of around 200 nm, and are com-posed mainly of 3R Tau isoforms. In PiD, Tau fibrils have a morphology similar to that found in CBD, and form typical inclusions called Pick bodies, with a laminar distribution. In PSP, Tau forms mainly straight filaments which are predominantly composed of 4R Tau. This suggest that the fibrils observed in the various diseases are structurally and morphologically distinct strains. The possibility that these differences could impact Tau seeding, toxicity and cell-to-cell propagation has huge implications for under-standing the heterogeneity of these diseases and the selective neuronal vulnerability and distinct clinical symptoms manifested in each disease.

In vitro Tau aggregation can be triggered in the presence of small molecule polyanions, such as heparin or arachidonic acid. However, it is becoming clear that the mechanisms underlying the assembly polyanions-induced Tau fibrils differs from that occurring in AD and in other Tauopathies, as it neither result in the formation of PHFs, nor in the lateral association of filaments into tangles. In fact, in vitro Tau assembly leads to the formation of fibrils which are usually polymorphic and do not always recapitulate the specific paired helical structure observed in native fibrils, both morphologically and in terms of mass per length. Furthermore, in vitro polyanions-induced assembly of Tau into filaments is generally inhibited by phosphorylation. Conversely, in AD, the MTBD flanking regions become abnormally phosphorylated, reducing their inhibitory effect and resulting in Tau aggregation. This does not rule out the possibility that hyperphosphorylation could occur after Tau fibril formation. Interestingly, dephosphorylation of PHFs isolated from AD brain has been reported to promote their disaggregation and release of physiologically "normal" Tau. Moreover, dephosphorylation of soluble abnormally hyperphosphorylated AD Tau inhibits its ability to self-aggregate into PHFs, again suggestive of a direct positive effect of Tau phosphorylation on aggregation in AD. Taken together, these data demonstrate that in vitro polyanions-induced Tau filaments are biophysically, biologically and morphologically distinct from native PHFs, most likely resulting in differences in terms of seeding and spreading capacity, as well as cellular and toxic behaviors. Although the implications of Tau fibril formation in the pathogenesis of AD remain controversial, recent findings suggests that the Tau fibrils could have an important role in the propagation mechanism of the misfolded protein. Therefore, unraveling the process of early Tau aggregation and elucidating the sequence, structural and molecular determinants that govern the formation of PHFs is crucial to elucidate the molecular mechanisms underpinning Tau aggregation and its role in the pathogenesis of AD and related Tauopathies.

Although advancements are required to better grasp the pathological mechanisms underlying AD, the involvement of Tau in AD pathogenesis is strongly suggested. However, the specific involvement of Tau, Tau modifications and/or Tau assembly state in AD onset and progression, as well as their relative contributions, remains largely unknown, as none of the experimental models used thus far could determine the sequence and causality of events occurring in the course of AD. A better understanding of Tau biological functions and a new insight into how Tau affects neuronal physiology is urgently required to address the current knowledge gap on the normal function of Tau and its role in neuropathologies and to allow the design of rational therapeutics.

In order to study the involvement of Tau in AD pathogenesis and to identify new therapeutic agents and diagnostic tools, it is necessary to produce Tau fibrils that have the same or similar structural and functional characteristics as those PHFs found in the AD brain. There is therefore still a need for preparing in vitro such Tau fibrils. All the Tau fibrils generated in vitro from recombinant Tau and used in diagnostics and drug discovery research require the addition of polyanions to induce aggregation and bear no resemblance to the PHFs found in the AD brain. To address these limitations, many companies rely on the use of PHFs isolated from AD brain. However, these materials are usually available only in small amounts and are very heterogeneous. Thus currently there is still a need for an in vitro method able to prepare Tau fibrils that resemble the PHFs found in the AD brain. The present invention was able to solve this problem by providing an in vitro method for preparing PHFs-like Tau aggregates.

SUMMARY OF THE INVENTION

An aspect of the invention provides a method for preparing PHFs-like Tau aggregates comprising:
(a) contacting R2 fragments consisting of SEQ ID NO: 1 or comprising SEQ ID NO: 1 with polyanions,
(b) allowing formation of R2 fibrils,
(c) breaking down the R2 fibrils into seeds,
(d) contacting Tau proteins comprising SEQ ID NO: 1 with the R2 fibrils seeds under conditions which allow Tau aggregation.

A further aspect of the present invention provides a use of R2 fragments consisting of SEQ ID NO: 1 or comprising SEQ ID NO: 1 for preparing PHFs-like Tau aggregates.

A further aspect of the present invention provide R2 fibrils obtained by the method of the present invention.

Another aspect of the present invention provides PHFs-like Tau aggregates obtained by the method of the present invention.

A further aspect of the present invention provides a composition comprising R2-seeded fibrils obtained by the method of the present invention.

Another aspect of the present invention provides a composition comprising PHFs-like Tau aggregates obtained by the method of the present invention.

A further aspect of the present invention provides a kit for preparing PHFs-like Tau aggregates comprising R2 fibrils obtained by the method of the invention, Tau proteins comprising SEQ ID NO: 1 and instructions for use.

Another aspect of the present invention provides a method for identifying compounds that are inhibitors of Tau aggregation, propagation and/or toxicity comprising:
(a) contacting Tau proteins comprising SEQ ID NO: 1 and R2 fibrils of the invention in the presence and absence of a test compound under conditions which allow Tau protein aggregation, propagation and/or toxicity effects,
(b) determining the amount of PHFs-like Tau aggregates formed in the presence and absence of the test compound, and
(c) comparing the amount of PHFs-like Tau aggregates formed in the presence of the test compound with the amount of PHFs-like Tau aggregates formed in the absence of the test compound wherein a test compound which decreases the amount of PHFs-like Tau aggregates formed, decreases Tau propagation and/or decreases Tau toxic effect is an inhibitor.

A further aspect of the present invention provides use of Tau aggregates obtained by the method of the present invention for preparing in vivo imaging agents that bind native Tau aggregates.

A further aspect of the present invention provides an inhibitor identified or obtained by the method of the present invention.

Another aspect of the present invention provides a composition comprising the inhibitor as identified or obtained by the method of the present invention.

A further aspect of the present invention provides a use of R2 fragment consisting of SEQ ID NO: 1 or comprising SEQ ID NO: 1 for screening and/or for the identification of an inhibitor, capable of modifying PHFs formation.

Another aspect of the present invention provides a kit for testing inhibitors of Tau aggregation comprising R2 fibrils obtained by the method of the invention, Tau proteins comprising SEQ ID NO: 1 and instructions for use.

Another aspect of the present invention provides a method for reducing the spread of Tau aggregation in the brain of a subject, the method comprising administering a pharmacologically effective amount of the inhibitor of the invention to the subject.

BRIEF DESCRIPTION OF FIGURES

FIG. 1 shows schematic depiction. SEQ ID No 1 (R2) is shown in bold. Extensions and modifications of SEQ ID No 1 included in SEQ ID No 2, SEQ ID No 3 and SEQ ID No 4 are shown in italic. The microtubule-binding domain (MTBD, K18, SEQ ID No 6) is underscored. Sequence of the longest adult human Tau isoform sequence (Tau 4R2N, 441 amino acid, SEQ ID No:5). The two other 4R-Tau isoforms SEQ ID No 7 (4R1N) and SEQ ID No 8 (4R0N) and two 4R-Tau mouse isoforms SEQ ID No 9 (4R2N) and SEQ ID No 10 (4R0N) can also be seeded by R2 (SEQ ID No 1) and alternative peptides (SEQ ID No 2 to 4) seeds. A detailed analysis of the seeding of the different Tau isoforms is described in FIG. 7 and FIG. 8.

FIG. 2 shows R2 (SEQ ID No 1) fibrils are prepared by incubating 100 μM of the peptides in presence of 1:4 (mol:mol) of heparin, at 37° C. under quiescent conditions for at least 12 h. Shaking may accelerate the process and lead to shorter fibrils, which are also able to seed Tau into rPHFs. The fibrils can be kept at 37° C. or RT for at least two weeks, but should not be frozen. The peptide concentration may be modified, but the molar ratio to heparin must remain at 1:4 (heparin:peptide). Standard buffer is 10 mM phosphate pH 7.4, 50 mM NaF and 0.5 mM fresh DTT. The buffer may be modified but the pH should remain in the range 7-8, the ionic strength between 50 and 150 mM and the presence of at least 0.5 mM fresh DTT is required. Buffer conditions outside these ranges have not been systematically studied. The formation of R2 fibrils can be assessed by EM, Thioflavin-S (ThS) binding and circular dichroism (CD) spectra. a. EM micrographs demonstrate the presence of R2 fibrils after 24 h of incubation at 37° C. under quiescent conditions. b. ThS kinetic curves demonstrate the fast aggregation rate of the R2 peptide, that plateau within a couple of hours. c. The CD spectra show a full conversion from random coil to β-sheet at 24 h. d. Alternative R2-derived sequences (SEQ ID No 2 to No 4, see FIG. 1) form fibrils under the same conditions as the R2 peptide (SEQ ID No 1), as demonstrated by micrographs.

FIG. 5 shows a schematic representation of rPHFs formation. 1. Preparation of R2 (or alternative peptides) fibrils: The R2 (SEQ ID No 1) or R2-derived peptides (SEQ ID No 2 to 4) peptide are mixed with heparin at a molar ratio of 1:4 (heparin: peptide) molar ratio, and incubated at 37° C. for at least 12 h to form R2 fibrils. 2. Production of the R2 seeds: To become potent seeds, the R2 (SEQ ID No 1) or R2-derived fibrils (SEQ ID No 2 to 4) are sonicated (using a tip sonicator). 3. Preparation of R2-seeded Tau (rPHF): Monomeric Tau is mixed at 1:1 (protein:peptide) molar ratio and incubated at 37° C. for at least 12 h to form R2-seeded Tau fibrils (the rPHFs).

FIG. 9 shows the seeding capacity of three mouse Tau isoforms (a.), namely m4R2N, m4R0N (4R-Tau) and m3R0N (3R-Tau) was investigated b. Only the mouse isoforms containing the R2 sequence (i.e. Tau m4R2N and m4R0N) are able to form rPHFs in the presence of R2 seeds. The R2 sequence (i.e. SEQ ID No 1) between mouse and human Tau is fully conserved, again suggesting that the seeding mechanism occurs through the recognition of the R2 seeds with the R2 sequence in the full length protein. c. Pairewise aligment of human Tau 4R2N (h4R2N) (SEQ ID NO:5) with the corresponding mouse isoform (m4R2N) (SEQ ID NO:9). The MTBR is highly similar (blue) and the R2 peptide is fully conserved between the two species.

FIG. 19 shows (A) Tau biosensor assay workflow, (B) R2 fibrils and rPHF fibrils seed aggregation in biosensor cell assay, (C) Confocal microscopy of aggregates in tau biosensor cells induced by R2 and rPHF transduction, (D) Pre-incubation of R2 fibrils with antibodies significantly reduces tau aggregation in biosensor cells.

FIG. 22 shows immunoprecipitation experiments show antibody rPHFs,1 and rPHFs,2 affinity for Tau monomers and rPHFs.

DETAILED DESCRIPTION OF THE INVENTION

Figure 3:
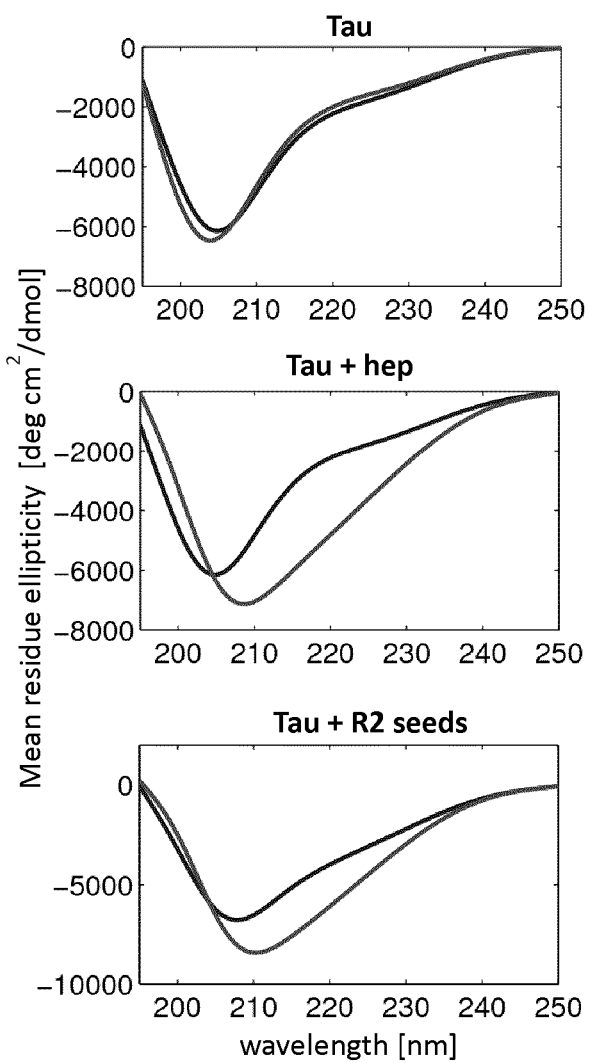
FIG. 3 shows a. Comparison between Tau fibrils formed in presence of heparin and seeded with R2 (SEQ ID No 1) seeds (rPHFs). Only the Tau fibrils formed in presence of R2 seeds present the typical paired-helical filament morphology of native Tau aggregates. b. The ThS kinetic curves demonstrate that Tau seeded with the R2 peptide lacks the nucleation phase and show a fast growth phase (black curve), compared to Tau aggregated in presence of heparin (red curve). This strongly suggested that the formation of rPHFs is based on a seeding mechanism, whereby the nucleation phase is bypassed. Tau incubated alone does not fibrilize (blue curve). c. The CD spectra show an increase of secondary structure in the case of Tau incubated with heparin and R2 seeds. The protein does not fully convert to a β-sheet conformation, in agreement with the fact that only a part of the protein is involved in the core of the fibrils, while the rest of the protein remains largely unfolded. d. Under the same conditions, Tau seeded with R2-derived peptides (SEQ ID No 2 to 4) also forms rPHFs.
Figure 3:
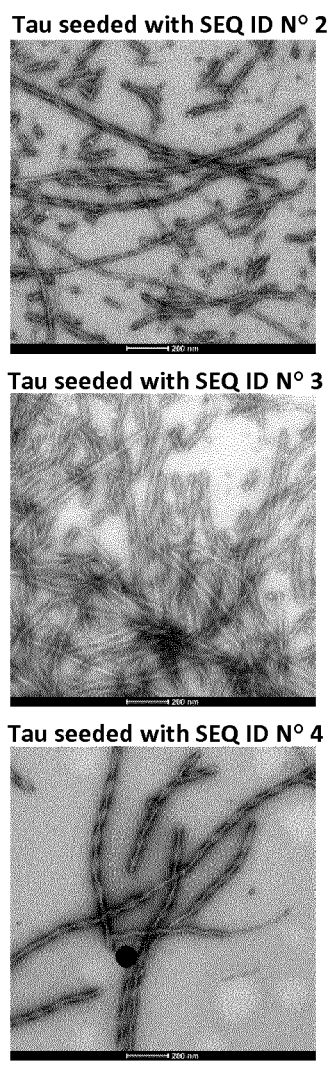

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components. In addition, as used in the specification and claims, the language "comprising" can include analogous embodiments described in terms of "consisting of" and/or "consisting essentially of".

As used in the specification and claims, the term "and/or" used in a phrase such as "A and/or B" herein is intended to include "A and B", "A or B", "A", and "B".

As used in the specification and claims, the singular form "a", "an" and "the" include plural references unless the context clearly dictates otherwise. Thus, for example, reference to "Tau protein" includes one, two, three or more Tau proteins.

By "subject" (or "individual" or "animal" or "patient" or "mammal") is meant any subject, particularly a mammalian subject, for whom diagnosis, prognosis, or therapy is desired.

Mammalian subjects include humans, domestic animals, farm animals, sports animals, and zoo animals including, for example humans, non-human primates, dogs, cats, guinea pigs, rabbits, rats, mice, horses, cattle, bears, and so on.

Although the R2 peptide (SEQ ID No 1) has been recognized as an important structural determinant of full length Tau aggregation, and contains the aggregation-prone peptide 'VKIINK' (PHF6*), there is—to the best of inventors knowledge—no report of the Tau seeding capacity of this peptide. It is herein reported that the R2 peptide can successfully seed Tau and K18 fibril formation. Most surprisingly, seeding with R2 resulted in the formation of paired helical filaments that exhibit striking similarities to bona fide PHFs (named recombinant PHFs; rPHFs). Inventors therefore investigated in more details the mechanism leading to such conformational switch, using different Tau isoforms, Tau originating from another mammalian specie, modified Tau, seeding by longer and shorter fragments of the R2 peptide, as well as diseased-linked mutated versions thereof. It was observed that, although shorter fragments of R2 are able to seed Tau, the formation of PHFs was unique to the full R2 sequence, and extended sequence thereof. R2 seeds successfully seeded all forms of Tau containing exon 10 (i.e. 4R Tau isoforms containing the R2 sequence), strongly suggesting a templating seeding mechanism. Moreover, given that the R2-seeded fibrils recapitulated the morphology of native PHFs, it was investigated whether they also recapitulated their seeding properties in a cellular model. Uptake and seeding of R2 seeds and rPHFs are reported in rat primary hippocampal neurons. To validate the application of the rPHFs in drug screening assays, a proof of concept experiment with a set of commercially available inhibitors has been performed. The method successfully allowed for identification of compounds that inhibit Tau protein aggregation.

In order to study the seeding capacity of R2, fibrillar aggregates from this peptide were generated. Peptide aggregation was induced by incubating the peptide in the presence of heparin at ratio 1:4 heparin:R2 and without agitation for at least 12 h. FIG. 2 presents detailed characterization of the kinetics and aggregation properties of the R2 peptide. The ThS aggregation curves show the typical sigmoidal aggregation curve with high ThS plateau value (FIG. 2 b). The circual dichroism (CD) spectra show that R2 adopts a β-sheet structure, (FIG. 2 c). To be used as seeds, R2 fibrils are sonicated using tip sonication (1 sec pulse trains) to form seeds of mean length of approximately 500 nm or shorter (the sonication parameters may depend on the sonicator).

The seeding of Tau 4R2N (SEQ ID No: 5) by R2 was performed in presence of 10 μM of sonicated peptide fibrils, added to 10 μM of the monomeric soluble Tau, at 37° C. under stagnant conditions. It was observed that R2 is capable of seeding the aggregation of full length Tau (FIG. 3).

Figure 4:
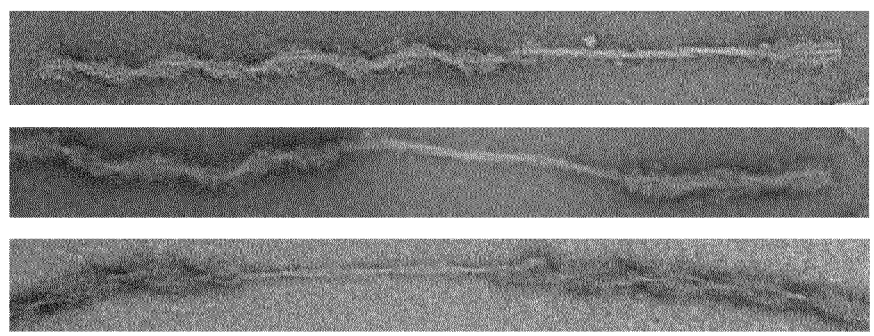
FIG. 4 shows EM micrographs showing the occurrence of the R2 peptide (SEQ ID No 1) linked to forming rPHFs at both ends, strongly suggestive of a seeding mechanism.

The morphological characteristics of the seeded fibrils using EM were determined (FIG. 3 a). Strikingly, seeding of Tau with R2 seeds revealed the formation of fibrils that are morphologically similar to that of native PHFs, with highly regular twisting and apparent protofilament ultrastructure. The fibrils morphology do not resemble that of the R2 fibril seeds, suggesting that the R2 fibrils interact with the full-length Tau in ways that reduce the conformational heterogeneity of Tau and favor specific conformations which then propagate during Tau fibril formation. The fact that the final Tau fibrils do not resemble the fibrils of the R2 peptide is expected due to the large sequence differences between R2 and Tau. R2-seeding occurs relatively fast, with PHFs-like fibrils observed after less than 4 h of incubation by EM. Further aguing for a seeding-based mechanism, EM micrographs show the formation of PHF-like fibrils at both ends of R2-derived fibrils (FIG. 4).

The ThS kinetic curves (FIG. 3 b) demonstrate that Tau seeded with the R2 peptide lacks the nucleation phase and show a fast growth phase, compared to Tau aggregated in presence of heparin. This strongly suggested that the formation of rPHFs is based on a seeding mechanism, whereby the nucleation phase is bypassed. Tau incubated alone does not fibrilize. Using CD (FIG. 3 c), it was shown that Tau incubated alone remains mostly random coil at all time points, while Tau incubated with heparin shows mixed secondary structure content, which is typical of Tau aggregated in presence of polyanionic compounds under quiescent conditions. Tau incubated with R2 exhibit similar CD spectra as that observed Tau fibrils formed in the presence of heparin.

A detailed schematic of the procedure to form rPHFs is presented in FIG. 5.

Figure 6A:
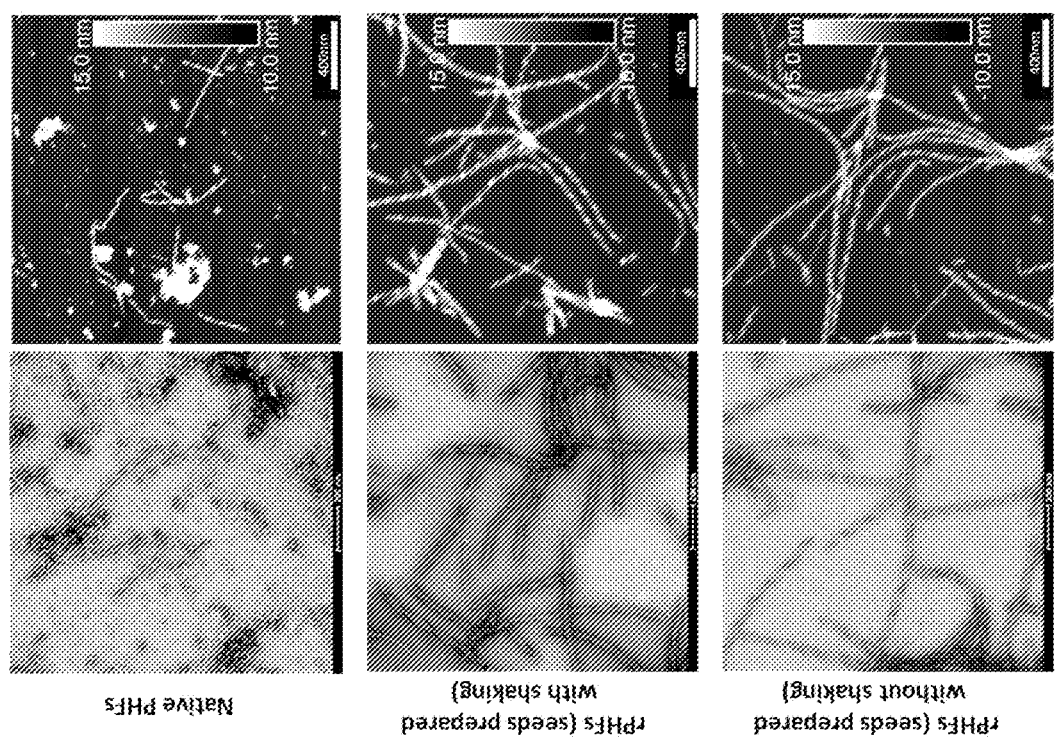
FIG. 6 shows a. EM and Atomic Force Microscopy (AFM) comparison between AD-derived native PHFs, and rPHFs formed with R2 seeds (themselves prepared under quiescent or shaking conditions). Native PHFs appear shorter, straighter and smaller than native PHFs. b. Determination of the fibrils half-periodicity by averaged autocorrelation functions of the transversal AFM height profiles and c. FFT analysis of the transversal AFM height profiles along the fibril axis. The half-periodicity is around 80 nm for the native PHFs and 100 nm for the rPHFs. d. Quantification of the average height of the fibrils. Native PHFs have an average height of around 11 nm and rPHFs around 9 nm. e. Electron micrographs of rPHFs (left) and rPHFs digested with (from left to right) pronase, trypsin, proteinase K, GluC and thrombin. Digested fibrils appear significantly thinner. f. Corresponding fibril width quantification. Although the native PHFs (~20 nm) are significantly thinner than rPHFs (~30 nm), digestion with diverse proteases decreases the width or the rPHFs to ~20 nm. Quantification was performed on at least five micrographs at a magnification of 49,000×, using Fiji. g. Summarizing table comparing the native PHFs with digested and undigested rPHFs in terms of periodicity and height (as assessed by AFM), and maximum width (as assessed by EM). Digested rPHFs show dimensions close to that of native PHFs.

In order to determine whether these R2-seeded Tau fibrils are morphologically similar to native PHFs, their morphological characteristic were determined through the analysis of EM and AFM images (FIG. 6). Determination of the fibrils half-periodicity by averaged autocorrelation functions of the transversal AFM height profiles and FFT analysis of the transversal AFM height profiles along the fibril axis shows that the half-periodicity is around 80 nm for the native PHFs and 100 nm for the rPHFs (FIG. 6 *b, c*). AFM also revealed that native PHFs have an average height of around 11 nm and rPHFs around 9 nm (FIG. 6 *d*). Maximum widths were quantified from EM micrographs of fibrils obtained from five independent experiments and revealed that, while native PHFs show an average maximum width of around 20 nm, rPHFs present a maximum width of around 30 nm (FIG. 6 *e-g*). It has been rationalized that this important difference in terms of width could originate from proteolytic cleavage of native PHFs occurring in the brain. The rPHFs were digested with different proteases. Fibrils digested with pronase, trypsin, proteinase K, GluC and thrombin appear significantly thinner than non-digested rPHFs (FIG. 6 *e-g*). Digestion with the diverse protases decreases the maximum width of the rPHFs to ~20 nm, a value that is similar to that of native PHFs. Taken together, these data are strongly suggestive of morphological similarities between the R2-seeded Tau and native PHFs, while the small differences in sizes could be attributed to the maturation process, the presence of PTMs and truncations in native fibrils and/or the fact that native fibrils are derived from a mixture of iso forms.

Figure 7A:
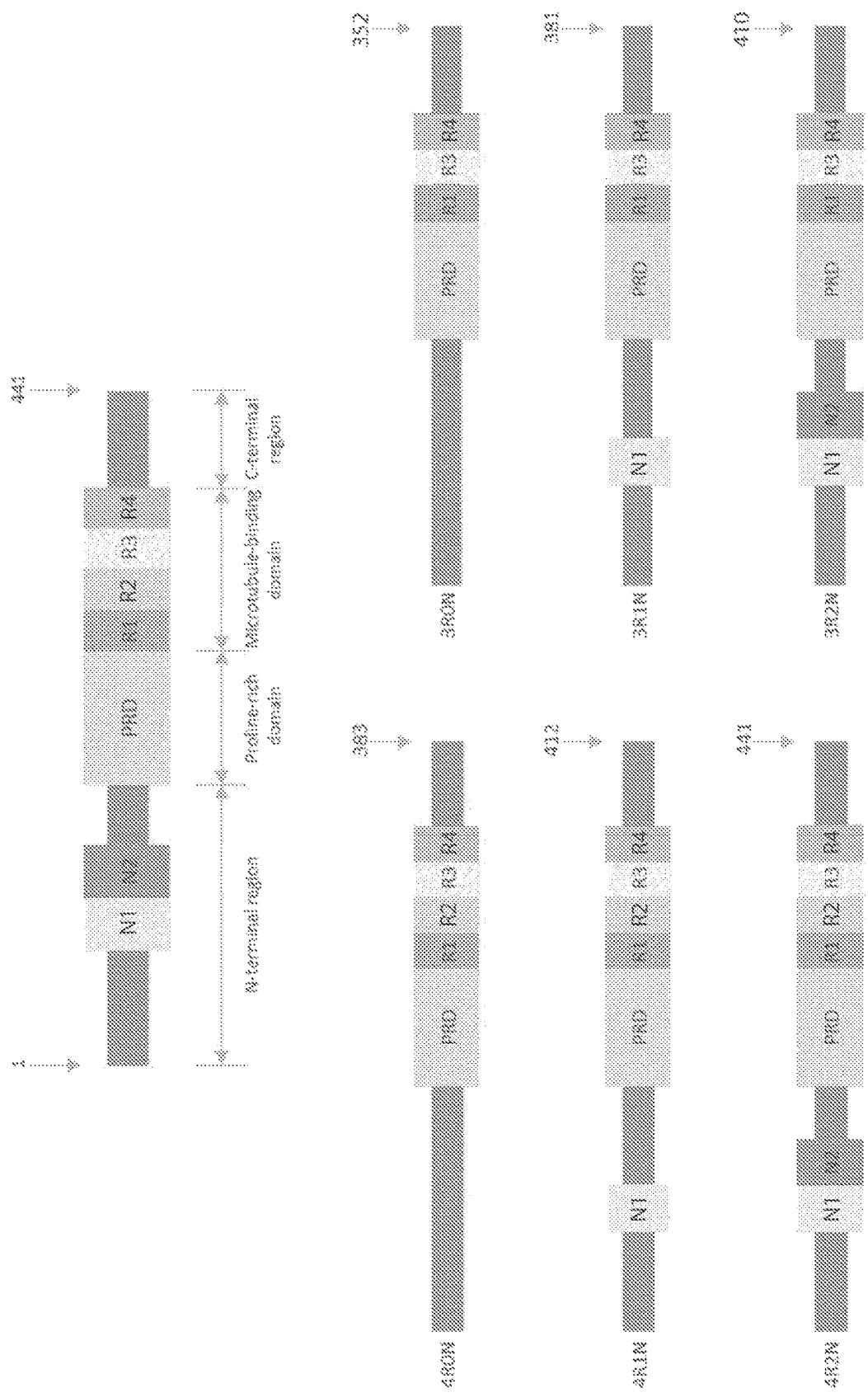
FIG. 7 shows a. Human Tau naturally occurs in six isoforms, depending on the alternative splicing of exons E2, E3 and E10, giving by so rise to the variations containing either 0, 1 or 2 amino-terminal inserts (0N, 1N and 2N, orange and red), and 3 or 4 microtubules binding repeats (3R and 4R, R2 exon is shown in blue). b. Under the conditions described in FIG. 3, of the six Tau isoforms, only those containing the R2 sequence (i.e. SEQ ID No 1 present in Tau 4R2N, 4R1N and 4R0N) are able to form rPHFs in the presence of R2 seeds, suggesting that the seeding mechanism occurs through the recognition of the R2 seeds with the R2 sequence in the full length protein.
Figure 7B:
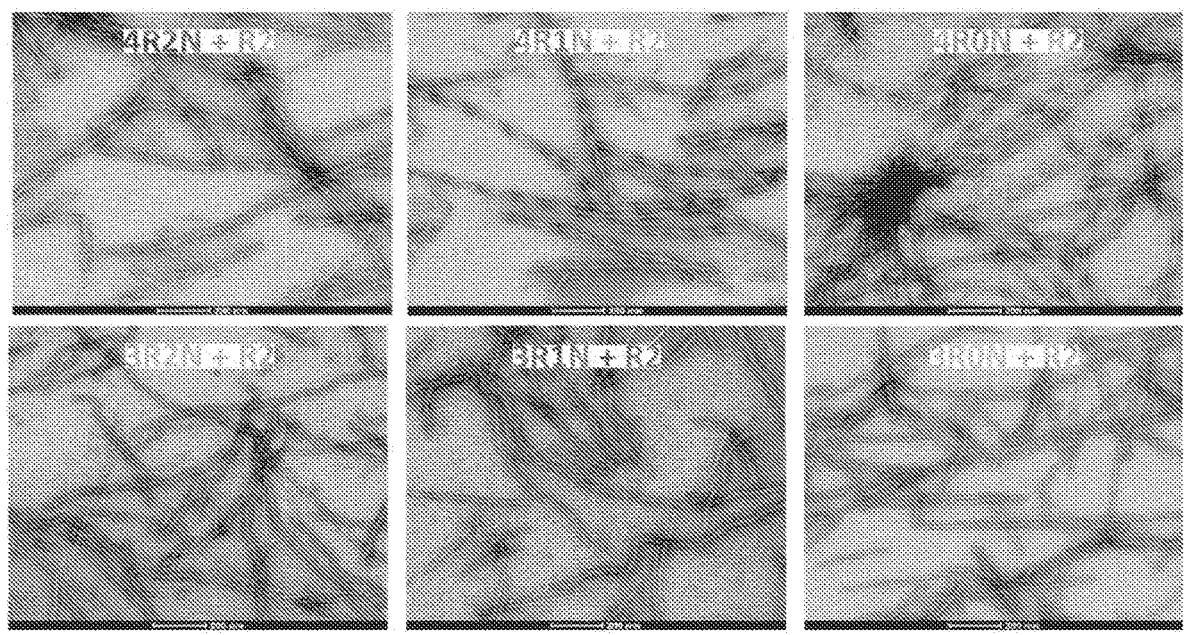
Figure 8:
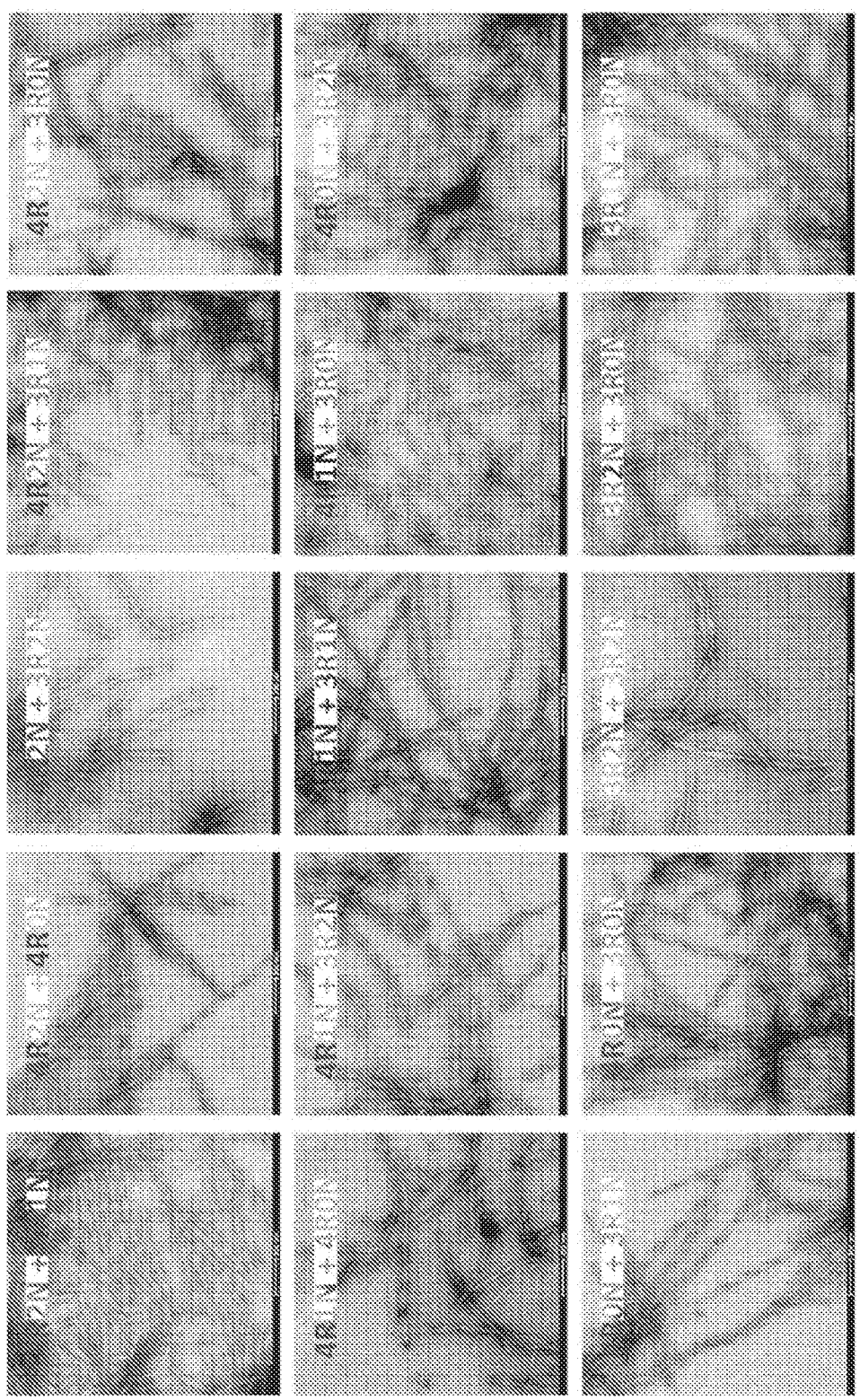
FIG. 8 shows Tau isoform mixtures (two isoforms per mixture, equimolar, 5 μM each) are able to form rPHFs in the presence of R2 seeds only when at least one of the two isoforms contains the R2 sequence (i.e. SEQ ID No 1 present in Tau 4R2N, 4R1N and 4R0N, highlighted in red), again suggesting that the seeding mechanism occurs through the recognition of the R2 seeds with the R2 sequence in the full length protein. However, it is not possible to determine whether the isoform lacking R2 (3R-Tau isoforms) co-aggregates with the isoforms containing R2 (4R-Tau isoforms) in the case of 4R/3R mixtures.

To assess the specificity of rPHFs formation, it was investigated whether they could form in the presence of other Tau isoforms. Of all six Tau isoforms, only those containing the R2 sequence (i.e. the 4R-Tau isoforms, namely Tau 4R2N, Tau 4R1N and Tau 4R0N, SEQ ID No 5, 7 and 8, respectively) are able to form rPHFs in the presence of R2 seeds (FIG. 7). This finding suggests that the seeding mechanism occurs through the recognition of the R2 seeds with the R2 sequence in the full length protein. Similarly, Tau isoform mixtures (two isoforms per mixture, equimolar) are also able to form rPHFs in the presence of R2 seeds when at least one of the two isoforms contains the R2 sequence (FIG. 8), again suggesting that the seeding mechanism occurs through the recognition of the R2 seeds with the R2 sequence in the full length protein.

It has been also investigated whether the seeding could occur with Tau originating from another mammalian species. To do so, three mouse Tau isoforms (m4R2N, m4R0N and m3R0N) were expressed and purified. These isoforms have regions of high similarity with the human Tau isoforms, mostly within the MTBD. Notably, the R2 sequence is fully conserved (FIG. 9 *c*). Similar to the human Tau isoforms, only the mouse isoforms containing the R2 sequence (i.e. Tau m4R2N and m4R0N, SEQ ID No 9 and 10, respectively) were able to form rPHFs in the presence of R2 seeds (FIG. 9), once again suggesting that the seeding mechanism occurs through the recognition of the R2 seeds with the R2 sequence in the full length protein.

Figure 10:
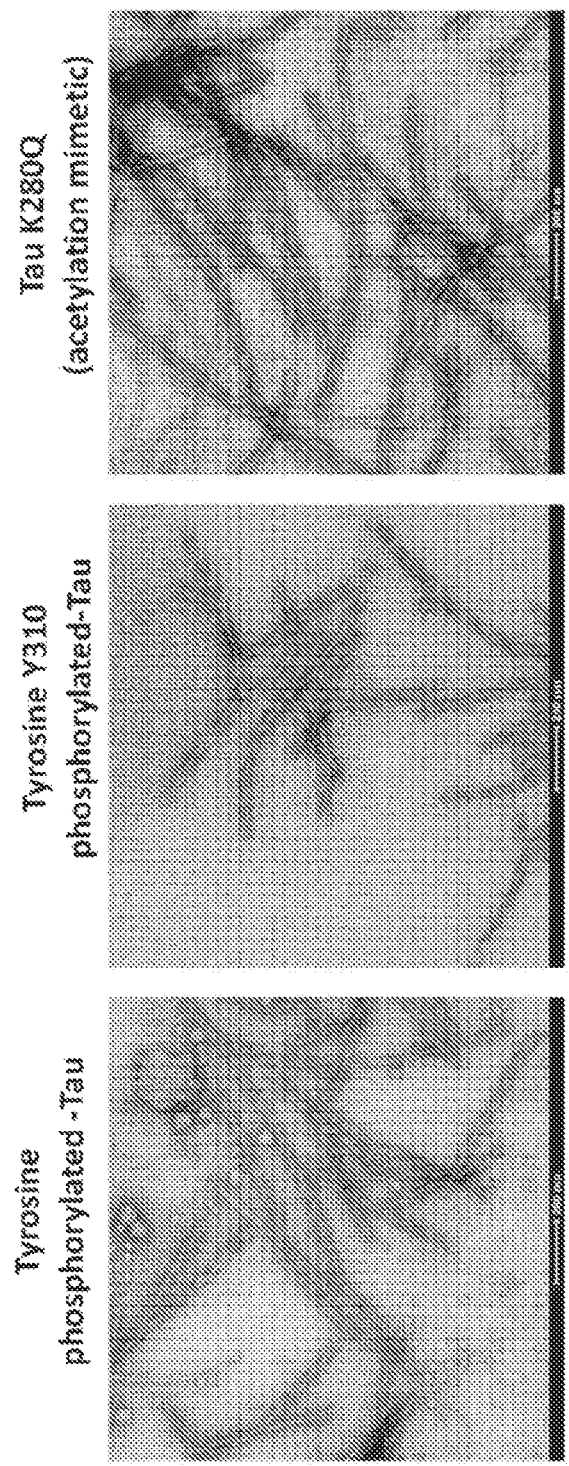
FIG. 10 shows Tau bearing post-translational modifications, such as tyrosine phosphorylation (on a mixture of all tyrosine residues, left panel, or specifically on tyrosine Y310, middle panel) or acetylation mimetic (K280Q, right panel) are able to form rPHFs, showing the robustness of the system and suggesting that modified Tau, such as Tau in diseased conditions, can be potentially seeded by R2 seeds, even when the modification is localized within the R2 sequence (SEQ ID no 1). Tyrosine phosphorylated Tau was prepared by incubating Tau (WT for tyrosine phosphorylation on a mixture of residues and Tau Y→F mutated Tau of all tyrosine residues except Y310 for specific phosphorylation on residue Y310) with the C-abl kinase at a ratio of 1:20 (kinase:Tau) for 4 h in 50 mM Tris, 5 mM MgCl2, 1 mM DTT, 20 mM Na3VO4 (phosphatase inhibitor) in the presence of 3 mM MgATP, pH, 7.5 at 30° C. The reaction mixture was followed by ESI-MS to verify the completion of the phosphorylation. Additional kinase and MgATP were added when needed. Phosphorylated Tau were purified by reverse-phase HPLC preparative C4 column (PROTO 300 C4 10 μm Higgins Analytical; buffer A: 0.1% TFA in water, buffer B: 0.1% TFA in acetonitrile) using a linear gradient of 30 to 40% of B in 40 min. Pure fractions were pooled and lyophilized.
Figure 11A:
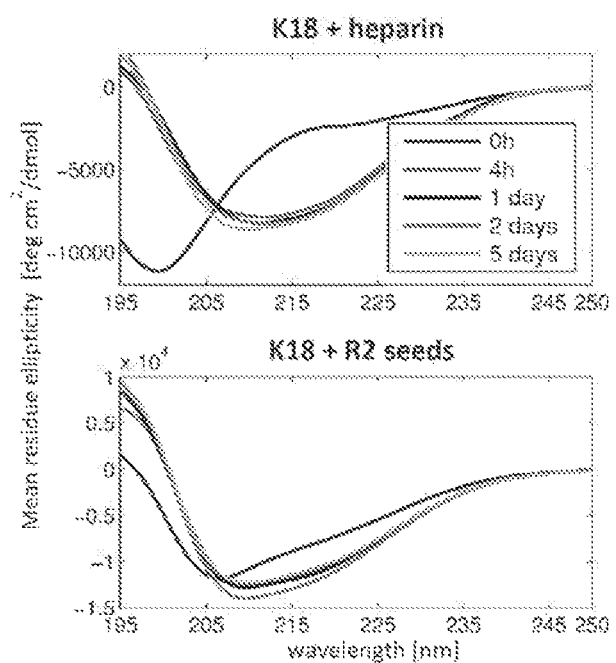
FIG. 11 shows R2 seeds added at a final concentration of 10 μM to seed 10 μM of monomeric K18. The aggregation is performed under static conditions at 37° C. for 5 days. As controls, K18 incubated alone and in the presence of 2.5 μM heparin are also evaluated. a. The CD spectra show a rapid increase in secondary structure in the case of K18 incubated with heparin and R2 (SEQ ID no 1). The final spectra differs between the two conditions, whereby the negative peak of the spectra of K18 incubated with R2 seeds is broader than that of K18 incubated with heparin. b. The ThS kinetic curves demonstrate that R2-seeded K18 has a faster growth rate compared to K18 aggregated in presence of heparin. The plateau value is lower than that of K18 incubated with heparin, also suggesting a difference in the fibrils structures. Although the ThS of R2-seeded K18 is low, it is still significantly higher than that of the R2 seeds by themselves (dashed black line), which confirms aggregation of K18 in presence of R2 seeds. c. EM micrographs show the presence of helical fibrils in the case of R2-seeded K18, while K18 fibrils formed in presence of heparin or mostly flat and curvy. d. In blue, the distribution of the width of R2-seeded K18 (maximum width=19.6+/−2.8 nm, minimum width=6.2+/−2 nm) and in red the distribution of the width of heparin-induced K18 fibrils (=9.5+/−1.9 nm) (mean indicated in green).
Figure 11B:
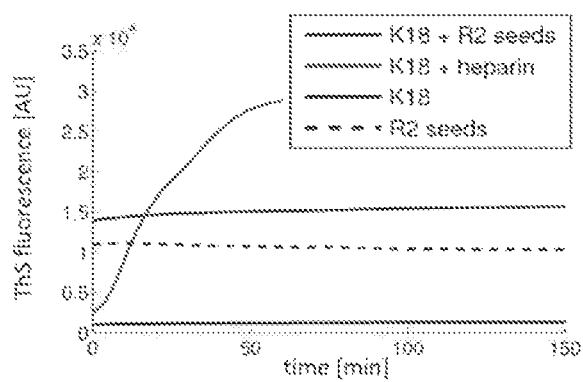
Figure 11C:
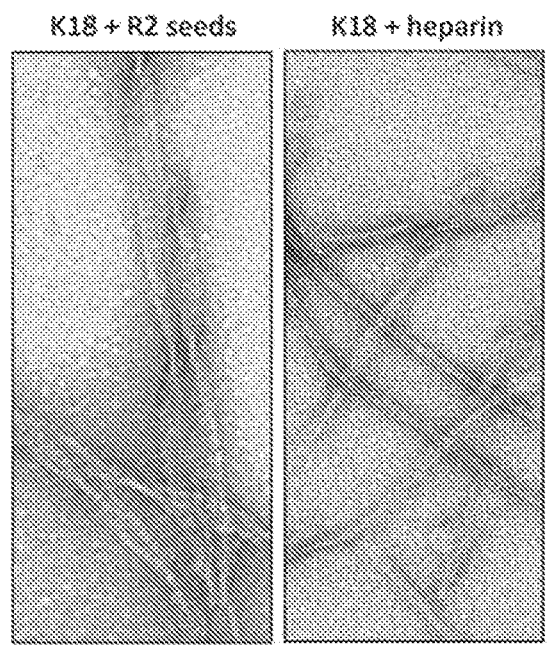
Figure 11D:
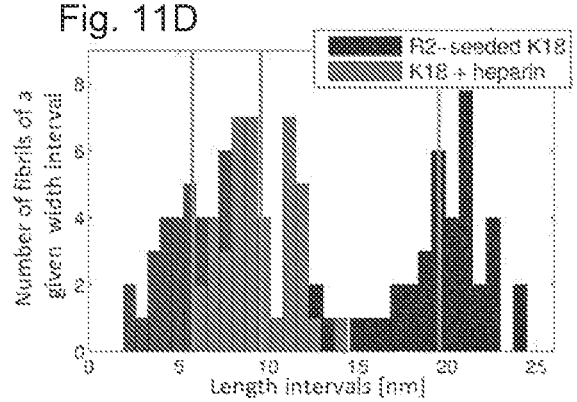

Next, it has been assessed whether Tau bearing PTMs could be seeded with R2 seeds into rPHFs. To do so, Tau phosphorylated on a mixture of tyrosine residues or specifically on residue Y310, or Tau acetylation mimetic (Tau K280Q) were incubated with R2 seeds. All modified forms of Tau were able to form rPHFs (FIG. 10), showing the robustness of the system and suggesting that modified Tau, such as Tau found in diseased conditions, could potentially be seeded by R2 seeds.

The capacity of R2 to seed the formation of K18 (SEQ ID No:6) fibrils was also determined, because many of the existing cellular models rely on the overexpression of WT and mutated versions of this Tau fragment. When R2 seeds were mixed with monomeric K18 at seeds-to-monomer ratios and conditions identical to that used in the case of the full length protein, efficient seeding of K18 was observed. Indeed, the CD spectra shows a clear increase in secondary structure, although the β-sheet content appear to be significantly less than that of K18 incubated with heparin (FIG. 11 *a*). Similar to the full length protein, the ThS kinetics shows the absence of a lag phase, and a growth phase that is significantly faster than that of K18 incubated in presence of heparin. However, the final ThS plateau value is half of that of heparin-K18 fibrils (FIG. 11 *b*). By EM, important morphological differences were observed between heparin-induced and R2-seeded K18 fibrils. The fibrils formed in the presence of heparin are relatively thin (9.5+/−1.9 nm), flat and curvy, whereas the R2-seeded fibrils are larger (maximum width=19.6+/−2.8 nm, minimum width=6.2+/−2 nm), with some degree of twisting (FIG. 11 *c, d*). These structural differences between heparin- and R2-seeded K18 fibrils may explain the differences in CD spectra and ThS plateau values. Moreover, and as observed in the case of R2-seeded Tau fibrils, the protofilament ultrastructure is largely apparent, while it is absent in heparin fibrils. Although R2-seeded K18 fibrils share with R2-seeded Tau fibrils the periodical twist and the protofilaments ultrastructure, these fibrils do not completely recapitulate the morphological appearance of native PHFs, as they do not show the "candy-like" appearance of the PHFs, and are missing the blurry aspect of the fibrils. This is most probably due to the absence of the N-terminal part of the protein, which account for the fuzzy coat, but which is likely to also participate in the morphological architecture of Tau PHFs.

Figure 12A:
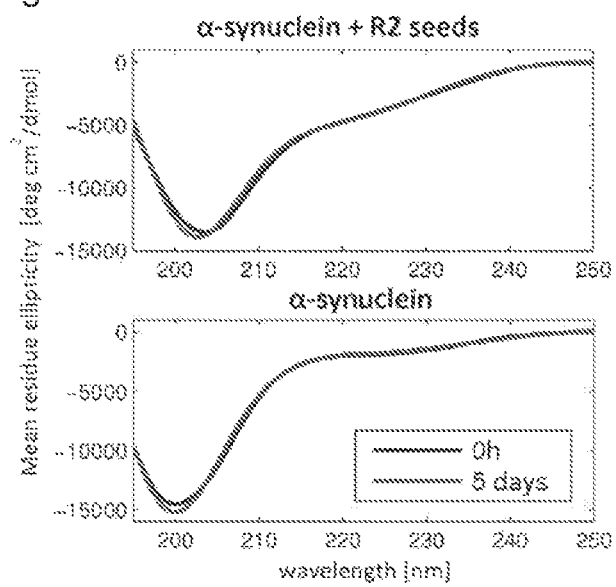
FIG. 12 shows R2 seeds added at a final concentration of 10 µM to seed 10 µM of monomeric α-Syn. The aggregation is performed under static conditions at 37° C. for 5 days. As controls, α-Syn incubated alone is also evaluated. Under these aggregation conditions α-Syn does not spontaneously aggregate. a. The CD spectra show a mixed structure that is not evolving with time for α-Syn incubated with R2 seeds, suggesting that the observed spectra is the result from the additive contributions of the seeds (highly structured) with that of α-Syn (predominantly unfolded), and not a new structure resulting from α-Syn seeding by R2 seeds. b. EM micrographs show the presence of fibrils in the case of α-Syn seeded with R2, but the observed fibrils have the morphology of the seeds themselves, suggesting that the observed fibrils are simply the seeds, and not seeded α-Syn.
Figure 12B:
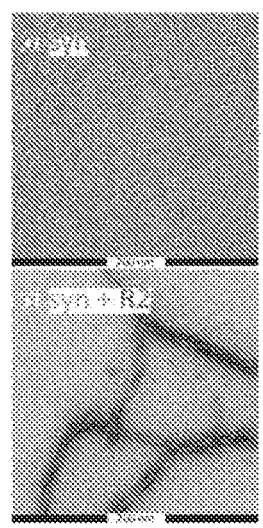

In order to assess the specificity of the seeding observed, i.e. the capacity of R2 seeds to specifically seed monomeric Tau or fragment thereof, the ability of R2 fibrils to seed the fibrillization of another amyloid protein, α-Synuclein (α-Syn), which composes the core of the Lewy bodies observed in dopaminergic neurons of patients suffering from Parkinson's disease (FIG. 12) was assessed. When monomeric α-Syn was mixed with R2 seeds, following the protocol and seed-to-monomer ratios described above, seeding of the α-Syn fibril formation was not observed, as demonstrated by the absence of β-sheet structure by CD (FIG. 12 *a*), compared to that of the R2 fibril seeds themselves. By EM, some fibrils were observed, (FIG. 12 *b*) but these are present in low amount, and are probably arising from the presence of the seeds themselves and/or the capacity of α-Syn to aggregate spontaneously (although very inefficient under quiescent conditions). These results combined with the results obtained with the Tau isoforms indicate that R2 seeding of Tau is the result of specific interactions between the full length protein and the peptides, and is likely to occurs between regions of the protein that interact upon fibrillization of Tau.

Figure 13:
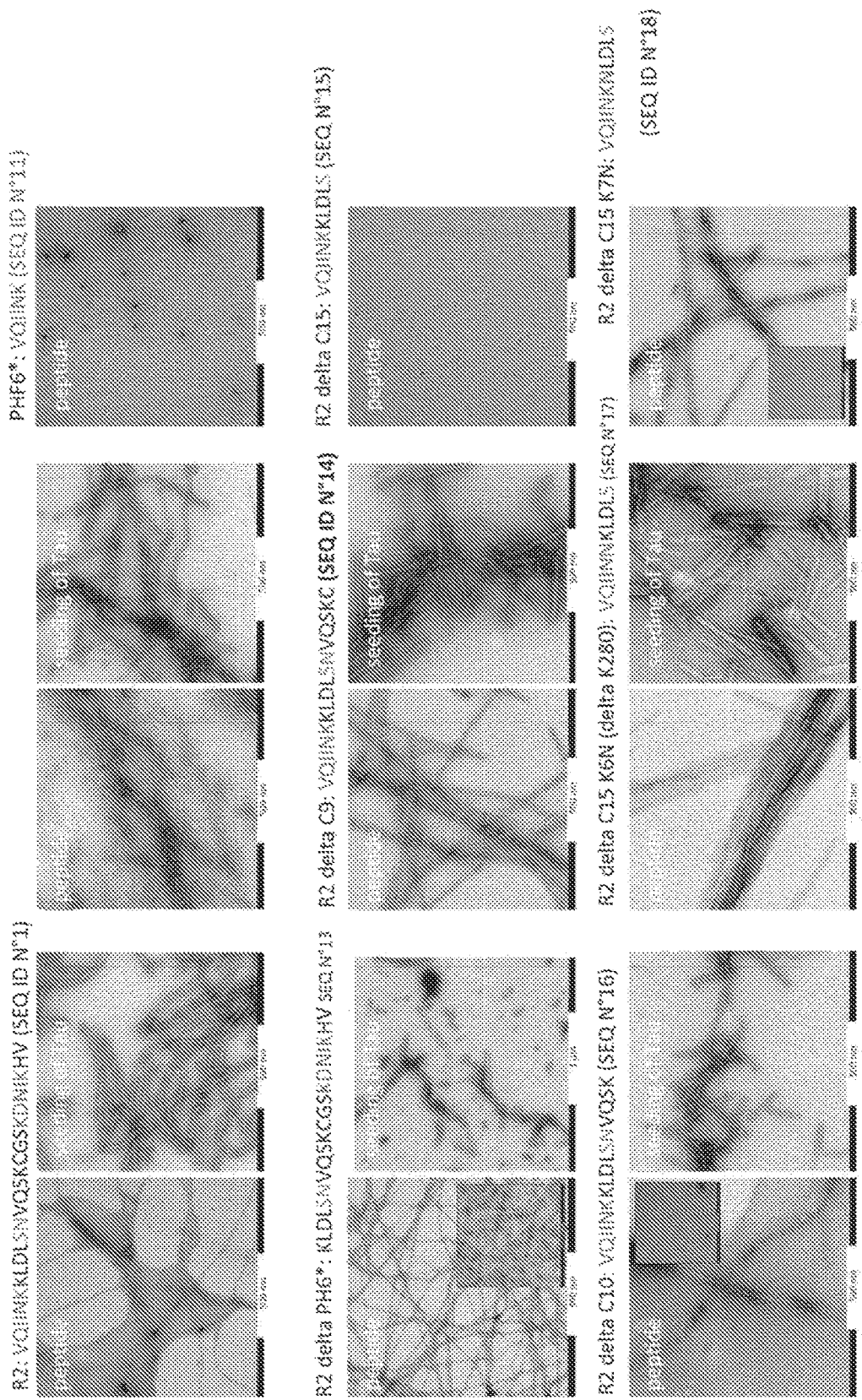
FIG. 13 shows R2-derived shorter peptides aggregated at a concentration of 100 µM in presence of 1:4 heparin: peptide molar ratio, at 37° C. under static conditions. EM micrographs of the aggregated peptides after 2 days (right panels). PHF6*, R2 delta C15 and R2 delta C15 K7N show an extremely low tendency to aggregate and are therefore were not able to seed Tau. Conversely, all the other peptides could successfully seed Tau (left panels), although only full length R2 (SEQ ID no 1) allowed the formation of rPHFs.

To elucidate the sequence determinants in R2 that allow for the seeding and the distinct morphological PHFs-like features, a library of R2-derived peptides of different lengths and characteristics were designed, which are summarized in FIG. 13. The R2 peptide can be viewed as made of several sub-domains: 1.) The well-known PHF6*, that is important in the context of β-sheet formation and stacking, hence often considered a key determinant motif for Tau aggregation; 2.) The 'SN' dyad motif that has a high propensity for β-turns; 3.) The secondary β-sheet forming peptide (KD)NIK; and 4.) The cysteine residue, which is of particular importance in aggregation as it might be implicated in dimerization, potentially occurring during the early steps of the aggregation process.

Using the library of peptides, it was first set out to assess which are the subdomains critical for R2 aggregation. Most interestingly, removal of the PHF6* (peptide R2 dPHF6*) does not abrogate R2 propensity to aggregate into fibrils. These fibrils are morphologically undistinguishable from that of the full length R2 peptide. Conversely, it was not possible to induce the aggregation of the PHF6* peptide by itself, demonstrating that, as such, the PHF6* has relatively low β-sheet propensity and requires additional structural elements to be capable of aggregation, suggesting that the other elements of R2 are important for its self-assembly.

Removal of the NIK β-structure-forming segment did not prevent the aggregation of the peptide (peptide denoted R2 dC5). This was expected as the PHF6* segment, which is considered the major β-structure-forming element of R2 is still present in the sequence. Morphologically, the fibrils formed are similar to that of the full length R2 in terms of width, although they appear significantly less twisted and curvy. Interestingly, even the removal of the remaining KD β-structure-forming residues (when removing residue up to the cysteine, peptide R2 dC9), does not significantly diminishes the peptide propensity to aggregate. However, the fibrils formed are highly twisted, suggesting that the mechanism of aggregation in absence of the secondary β-sheet forming element is different. Interestingly, the peptide R2 dC10 shows substantially lower aggregation propensity compared to the R2 dC9, although the only difference is the presence of the C-terminal cysteine residue. The morphology of the fibrils is also different from that of the R2 dC9. R2 dC10 fibrils are also highly polymorphic in terms of width and periodicity, underscoring the critical role of the cysteine residue in fibril formation and resulting biophysical characteristics.

Further C-terminal shortening of the peptide (up to the serine residue, peptide R2 dC15) abrogates the propensity of the peptide to aggregate. Compared to the R2 dC10, this peptide is missing one structural element, the 'SN' β-turn, which therefore might be important in the aggregation of the R2 peptide. Alternatively, the absence of fibrils formation could be the result of the cumulative effects from removing the other missing elements (i.e. 'SN' β-turn, the cysteine, the (KD)NIK β-sheet).

The effect of mutations in the R2 peptide was also probed. Indeed, R2 compact conformations have been attributed to salt bridges between aspartic acid (D) and lysines residues (K). Therefore, mutating a lysine K280 or K281 into an uncharged asparagine is likely to affect the peptide capacity to reach stable conformations, hence influencing its propensity to aggregate. Moreover, deletion of K280 is linked to familial Tauopathies and has been associated with increased aggregation of Tau, and acetylation of this residue has been associated with the AD. Taken together, these data further suggest an important role of the R2 lysine residues in its biophysical properties. Mutant peptides were therefore designed, in which either the positively charged K280 or the K281 lysine residues were replaced by an uncharged asparagine residue (R2 dC15 K6N and R2 dC15 K7N). The inability of the asparagine residue to form salt bridges with aspartic acid are likely to stabilize hydrogen bounded conformations, hence favoring R2 dC15 aggregation. Indeed, it was observed that both R2 dC15 K6N and R2 dC15 K7N were able to aggregate, while the WT R2 dC15 was not able to do so. More strikingly, the K6N mutation (corresponding to lysine K280) provoked very fast aggregation, compared to the WT full length R2 peptide, while the K7N mutation only induced limited aggregation. This shows that the K280 residue must have some specific inter- or intra-molecular interacting residues, and its role cannot be simply substituted by the K281 residue. Moreover, the fibrils formed by R2 dC15 K6N are uniquely flat and show a tendency to lateral aggregation that is not observed for any of the other peptides.

Having determined which of the R2-derived peptides are capable of aggregation and characterized their aggregation kinetics and fibril morphology, it was next investigated whether some of the R2-derived peptides could induce the seeding of Tau and K18, and whether it would lead to the formation of rPHFs fibrils. In order to reach this goal, fibrils of the peptides that were able to aggregate (R2 dC5, dC9, dC10, dC15 K6N and dPHF6*) were sonicated and added to monomeric Tau or K18 at molar ratios of 10 μM: 10 μM (i.e. under the same experimental conditions as those leading to R2-seeding of Tau and K18).

By EM, it was observed that R2 dPHF6* seeds Tau, in spite of the fact that it lacks the PHF6* hexapeptide. The observed fibrils do not resemble native PHFs, although it was possible to see some degree of helical twisting in the case of R2 dPHF6*-seeded Tau.

When investigating the capacity of R2 dC5 (i.e. missing NIK, part of the KDNIK β-motif) to induce Tau seeding, efficient seeding was observed by EM. Although seeded Tau is mostly twisted, the PHFs-like structure is not apparent. This suggests that the removal of as little as five residues in the C-terminal of the R2 peptide is sufficient to abrogate the PHFs-like assembly. In fact, these residues are part of the second β-sheet forming segment of R2 (i.e. the KDNIK motif), and suggest that it is crucially implicated in the structural basis of R2-induced Tau PHFs formation.

Corroborating this hypothesis, complete removal of KDNIK (R2 dC9) results in the formation of highly twisted fibrils. Interestingly, the seeded fibrils resemble that of the R2 dC9 seeds, which also forms highly regularly twisted fibrils. This is suggestive of a template-assisted growth, whereby the Tau molecules folding is guided by the conformation of the R2 dC9 peptide, resulting in the formation of R2 dC9-seeded Tau fibrils presenting morphological similitudes with the R2 dC9 fibrils.

Interestingly, although R2 dC9 (i.e. lacking the KDNIK motif) and R2 dC10 (i.e. lacking the KDNIK motif and the cysteine residue) form very distinct fibrils, the fibrils formed following seeding by both peptides are strongly similar. This may be due to the sonication step, which might induce splitting of the assembled protofilaments observed in R2 dC10, resulting in a more homogenous population of thin twisted filaments that are similar to those of R2 dC9.

Finally, the seeding capacity of the mutant R2 dC15 K6N was probed. The formation of laminar structures was observed. This demonstrates that—as in the case of R2 dC9—the seeding propagates the morphology of the seeds, and argues for a template-assisted growth, whereby the Tau molecules could laterally stack along the R2 dC15 K6N fibrils.

Figure 14:
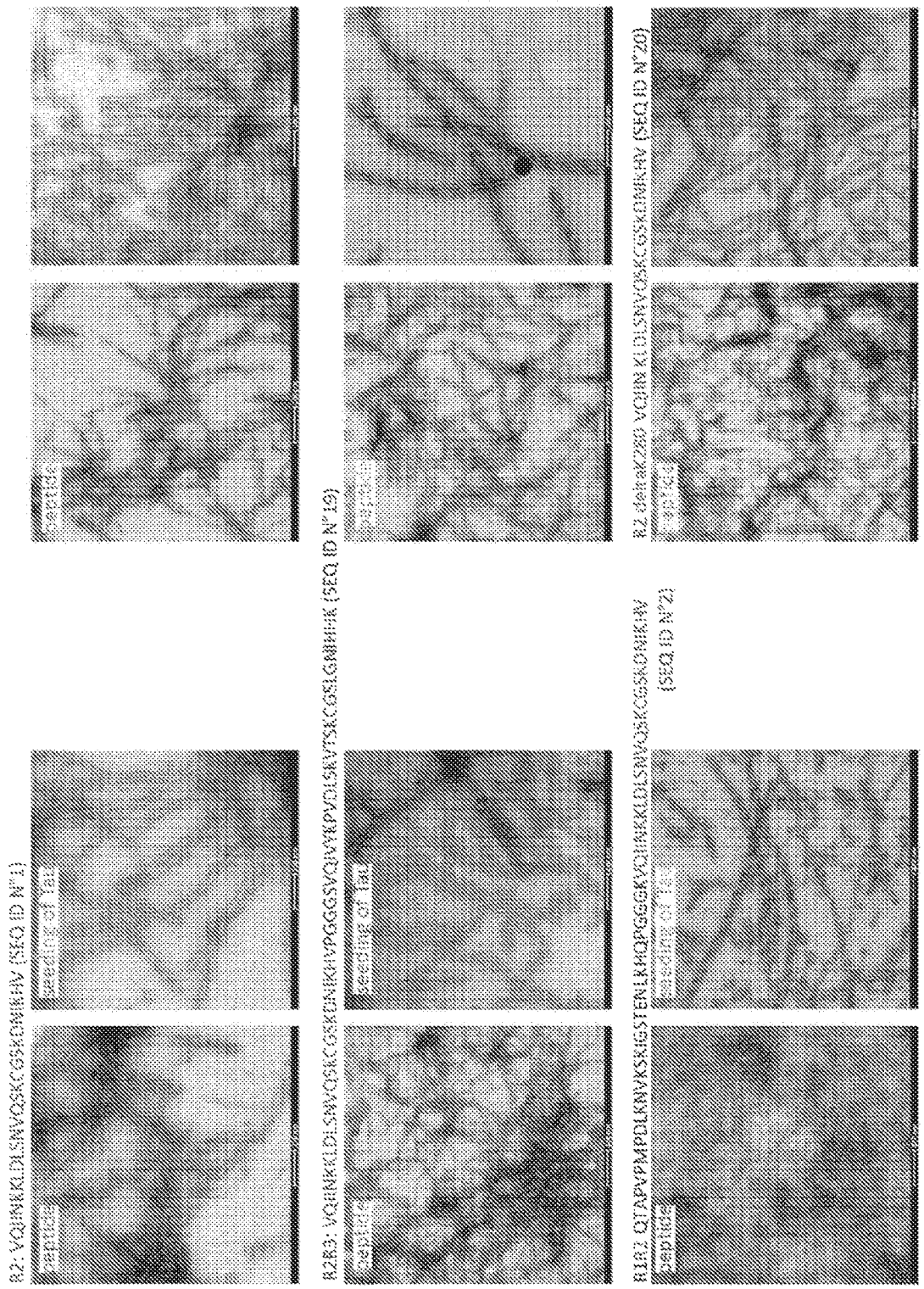
FIG. 14 shows R2-derived longer peptides aggregated at a concentration of 100 µM in presence of 1:4 heparin: peptide molar ratio, at 37° C. under static conditions. EM micrographs of the aggregated peptides after 2 days (right panels). All peptides are able to aggregate and seed Tau. However, only R2, R1R2 (SEQ ID no 2), R2 extended to the PGGG (SEQ ID no 3) motif and R2 extended and mutated to the SGGG motif (SEQ ID no 4) allowed the formation of rPHFs. Conversely, R2R3 and R2 delta K280 seeded the formation of Tau fibrils lacking the PHFs morphology, possibly due to the fact that they form seeds that are dominated by the modification (mutation delat K280) or extended motif (R3), and therefore forms seeds of morphologies that are not similar to that of R2 seeds.

Next, the capacity of longer versions of R2 peptide to seed Tau into rPHFs was determined. These data are summarized in FIG. 14. All longer versions of R2 were able to aggregate in presence of heparin. When R2 was extended to include the C-terminal 'PGGG' motif, believed to be implicated in turns, the formation of rPHFs was retained. When the diseased-linked mutation P301S is introduced in this peptide (the 'PGGG' motif thereby becoming 'SGGG'), the capacity of the peptide to seed monomeric Tau into rPHFs is also retained. Conversely, when another disease-linked mutation, namely ΔK280 is introduced in the R2 peptide, the peptide seeds are not able to seed Tau into rPHFs, as assessed by EM. These finding show that different mutations may differently affect the formation of R2 fibrils and hence their seeding capacity.

Figure 15A:
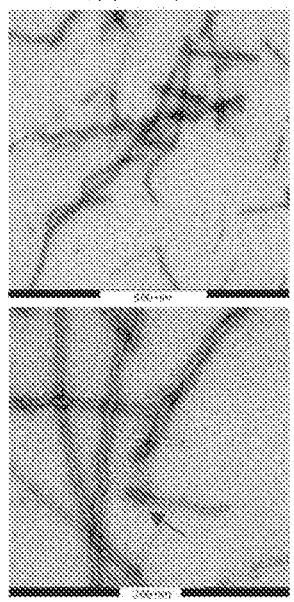
FIG. 15 shows R3 seeds prepared under the same conditions as the R2 seeds and used at a final concentration of 10 µM to seed 10 µM of monomeric Tau. The aggregation is performed under static conditions at 37° C. for 5 days. a. EM micrographs show that R3-seeded Tau forms filaments of different width, suggesting protofilament assembly. Red arrow show the possible seeding from a R3 filament. b. The distribution of the widths of R3-seeded Tau (top panel) and R3 fibrils (bottom panel).
Figure 15B:
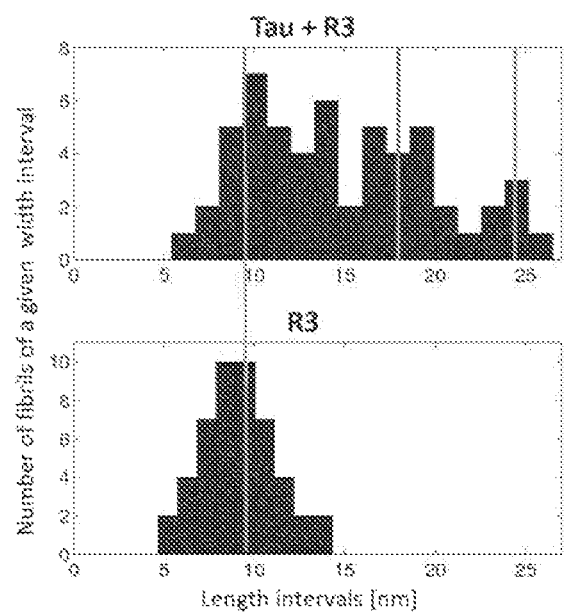

The effect of extending the R2 peptide to its adjacent repeat peptide, namely R1 or R3 was also investigated. Strikingly, the R1R2 peptide is able to seed Tau into rPHFs, while the R2R3 peptide is unable to do so. Possibly, the strong fibrillization potential of R3 dominates the formation of fibrils in the case of R2R3, leading to fibrils that are structurally different from the R2 fibrils. Corroborating this hypothesis, the R3 peptide seeds by themselves, although being able to seed Tau, do not induce the formation of rPHFs (FIG. 15). Conversely, the fact that R1 do not show significant aggregation potential allows the formation of R1R2 fibrils that may structurally resemble R2 fibrils, and therefore are able to seed monomeric Tau into rPHFs.

The alternative sequences capable of seeding Tau into rPHFs are referred to as SEQ ID No:2 (R1R2), SEQ ID No:3 (R2 'PGGG' extended), and SEQ ID No:4 (R2 'SGGG' extended) (see FIG. 1).

As such, these data demonstrate the versatility of R2-derived peptides to form various fibrils and to induce seeding of Tau, while the unique PHFs-like fibril morphology is achieved only in presence of the full length peptide, or extended versions thereof, suggesting that all sub-domains are required to induce the Tau conformation that is necessary to obtain fully fledged PHFs.

Next, the findings of the present invention were validated using a cellular model, the hippocampal rat primary neurons. Primary neurons were transfected with full length Tau and K18 ΔK280, and cells were treated with R2, R2-seeded Tau or R2-seeded K18 at a concentration of 1 μM, 12 h post-transfection. After 3 days, the coverslips were processed for ICC. The uptake is strong in the neurons overexpressing Tau (FIG. 16) or K18 ΔK280 (FIG. 17) and treated with R2-seeded Tau or K18 respectively, while it does not appear to occur when the neurons are treated with R2 fibril seeds only. Although the intracellular ThS signal is relatively high, it is difficult to distinguish between uptake of exogenous material and seeding of endogenous and/or overexpressed Tau/K18 ΔK280, especially since the concentration used here is relatively high (1 μM).

Figure 16A:
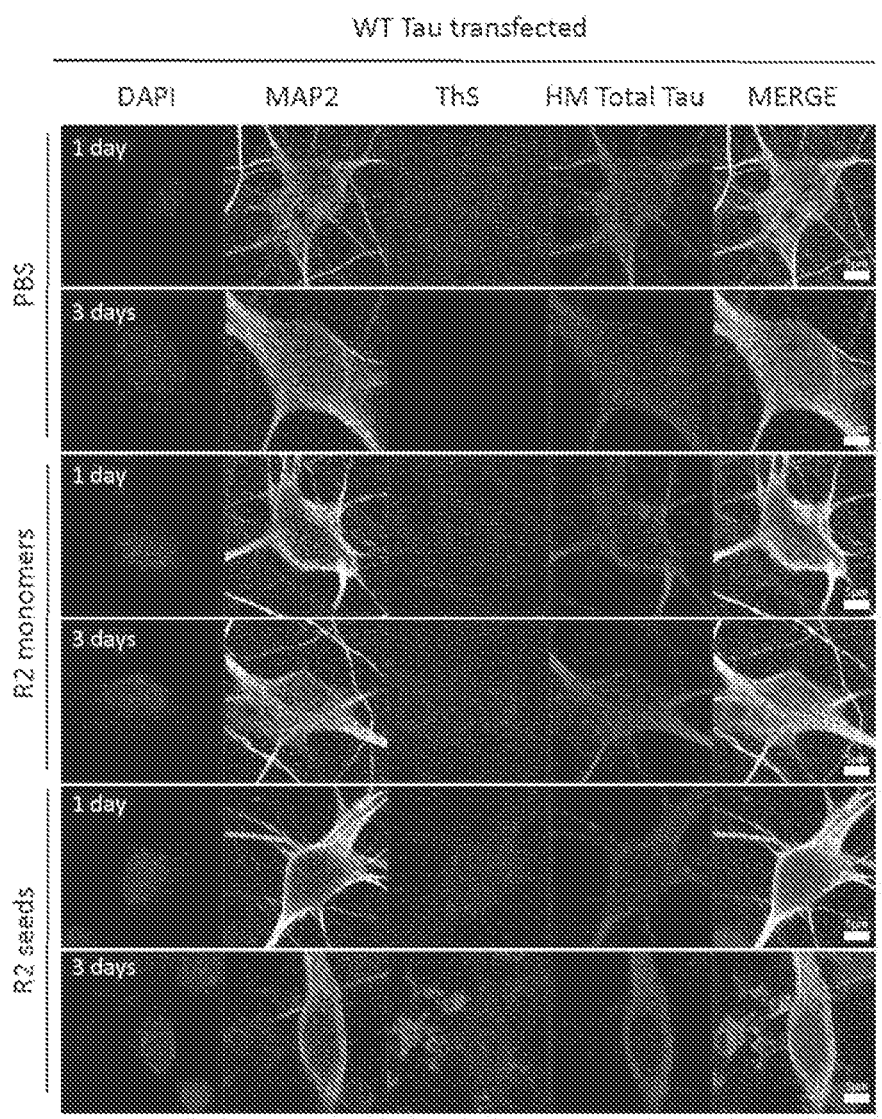
FIG. 16 shows hippocampal primary neurons transfected with 2 µg of WT Tau 4R2N and treated with a. PBS, 1 µM R2 monomers, R2 seeds, b. R2-seeded Tau (rPHFs) or R2-seeded K18 for 3 days and processed for ICC. From left to right: DAPI staining to show the nucleus (blue), staining with anti-MAP2 antibody identifying neurons (white), ThS staining (green), polyclonal HM anti-total Tau antibody (red) and merged. Immunocytochemical analysis shows strong ThS signal in transfected neurons (i.e. HM total Tau positive) treated with R2 seeds, R2-seeded Tau or R2-seeded K18, while neurons treated with R2 monomers and PBS are ThS-negative. The ThS is intracellular in the case of R2-seeded Tau and R2-seeded K18, while it remains mostly extracellular in the case of R2 seeds. The amount of ThS dots is very strong in non-neuronal cells (MAP2-negative, dashed red rectangles). c. Zoomed images of R2-seeded Tau (left panel) and K18 (right panel) are shown at the bottom of the figure.
Figure 16B:
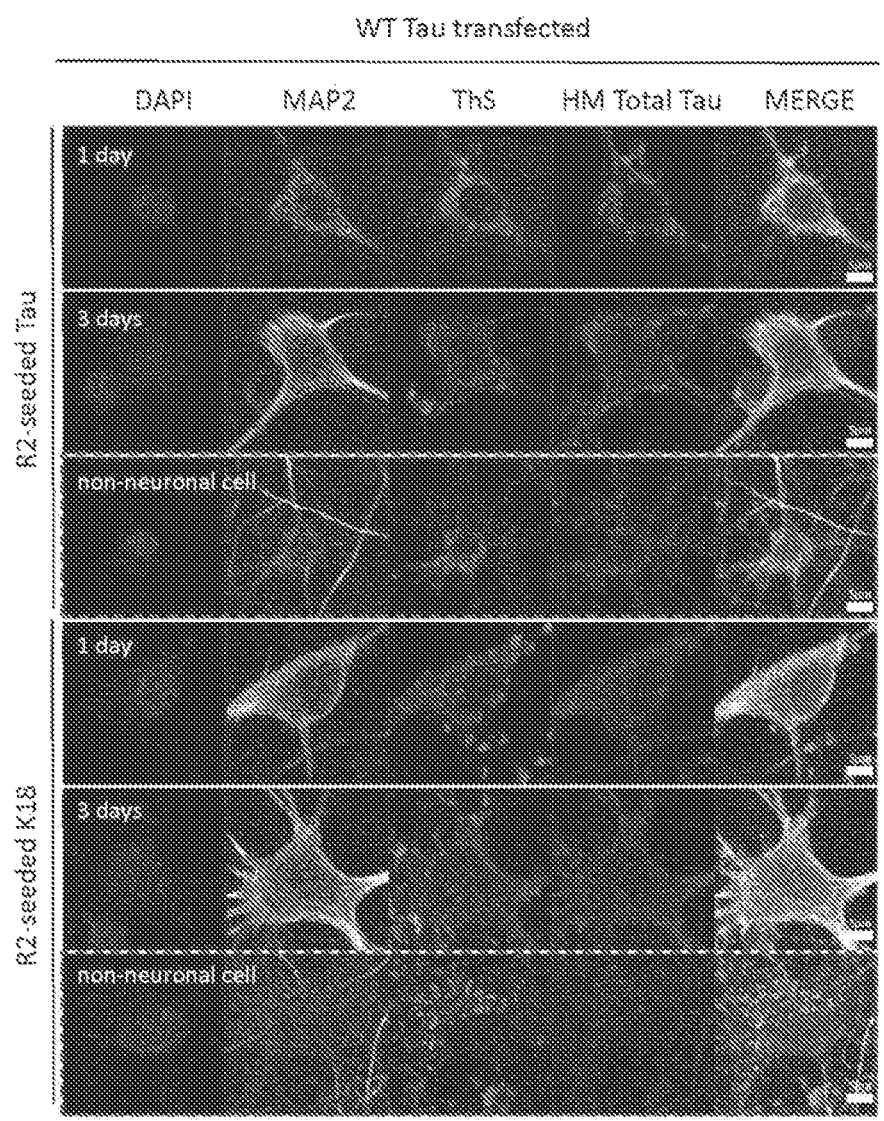
Figure 17A:
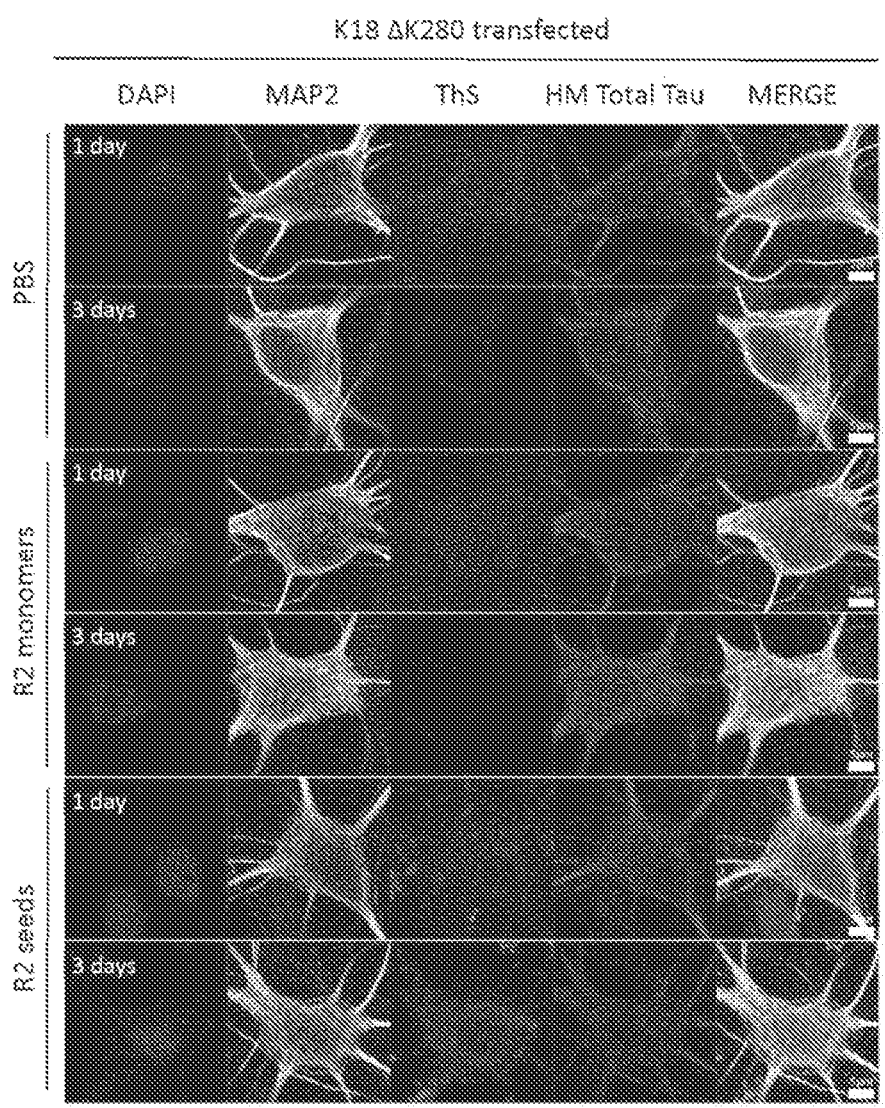
FIG. 17 shows hippocampal primary neurons transfected with K18 ΔK280 and treated with a. PBS, 1 µM R2 monomers, R2 seeds, b. R2-seeded Tau or R2-seeded K18 for 3 days and processed for ICC. From left to right: DAPI staining to show the nucleus (blue), staining with anti-MAP2 antibody identifying neurons (white), ThS staining (green), polyclonal HM anti-total Tau antibody (red) and merged. Immunocytochemical analysis shows strong ThS signal in transfected neurons (HM total Tau positive) treated with R2 seeds, R2-seeded Tau or R2-seeded K18, while neurons treated with R2 monomers and PBS are ThS negative. The ThS is intracellular in the case of R2-seeded Tau and R2-seeded K18, while it remains extracellular in the case of R2 seeds. The amount of ThS dots is very strong in non-neuronal cells (MAP2-negative, dashed red rectangles). c. Zoomed images of R2-seeded Tau (left panel) and K18 (right panel) are shown at the bottom of the figure.
Figure 17B:
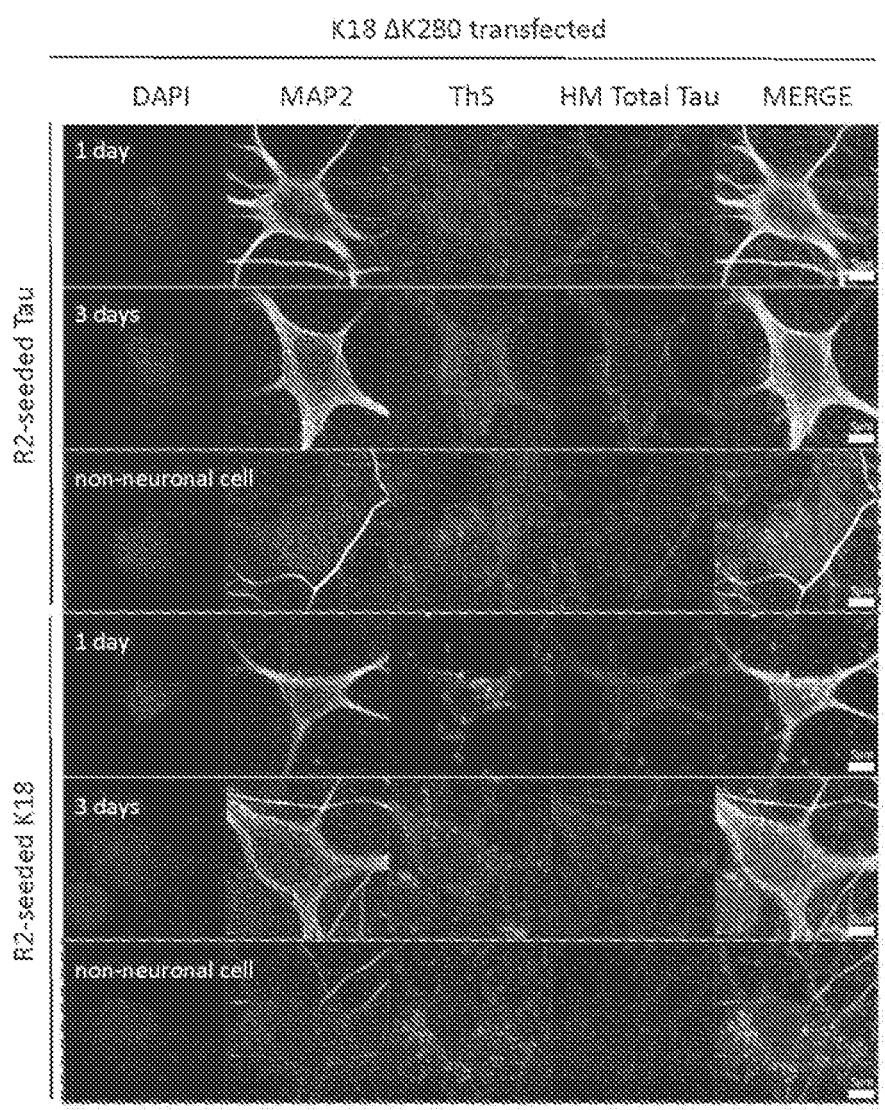
Figure 18A:
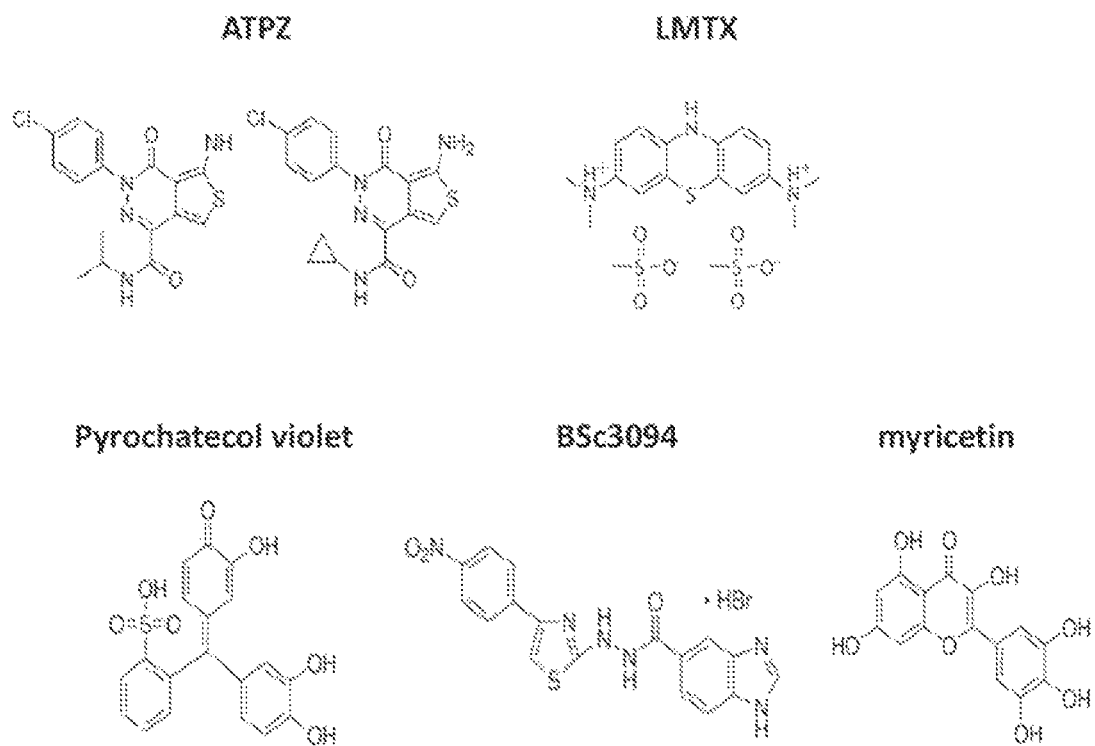
FIG. 18 shows monomeric Tau protein (4R2N) mixed at 5 µM with 5 µM R2 seeds (SEQ ID No 1) in presence or absence of a commercially available inhibitor (1 µM, 10 µM 100 µM). The aggregation kinetic is followed using ThS fluorescence. a. The list and structure of the 5 inhibitors used in this proof of concept assay. b. As an example, the full kinetic of Tau incubated in presence of R2 seed with LMTX at 1 µM (orange), 10 µM (grey) or 100 µM (yellow) or in absence of inhibitor (blue). c. End timepoint ThS value of Tau incubated in presence of R2 with the five selected inhibitors at 1 µM (orange), 10 µM (grey) or 100 µM (yellow) or in absence of inhibitor (blue). The inhibition is dose-dependent, the inhibitors show various inhibition potencies (e.g. low for BSc3094, high for LMTX). The inhibitor show similar inhibition potency for the fibrilization of Tau in presence of heparin or in presence of R2 seeds, suggesting that they interfere with the monomeric form of the protein, possibly locking it in a conformation that is not prone to aggregation. d. Corresponding EM micrographs confirm the absence of significant fibrilization in the presence of most inhibitors. The presence of oligomeric species corroborate the hypothesis that Tau is locked in OFF-pathway conformations. The scale bars are 500 [nm].
Figure 18B:
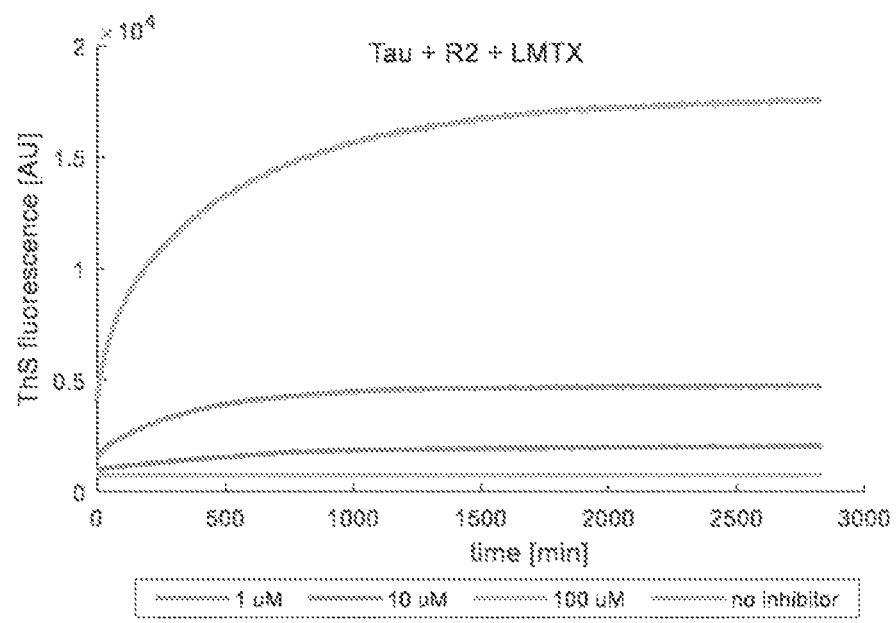
Figure 18C:
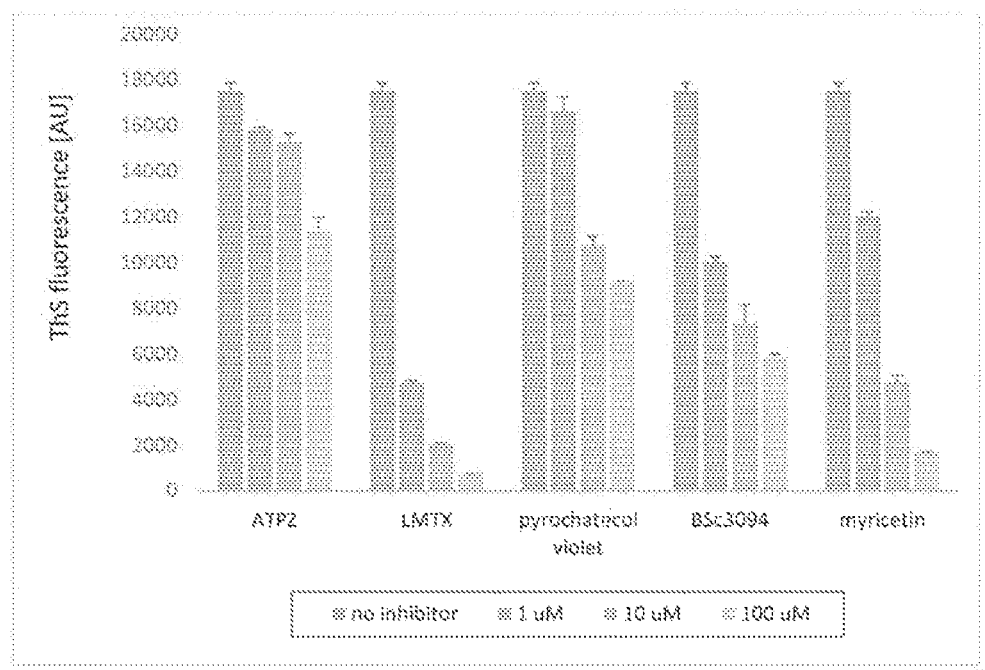
Figure 18D:
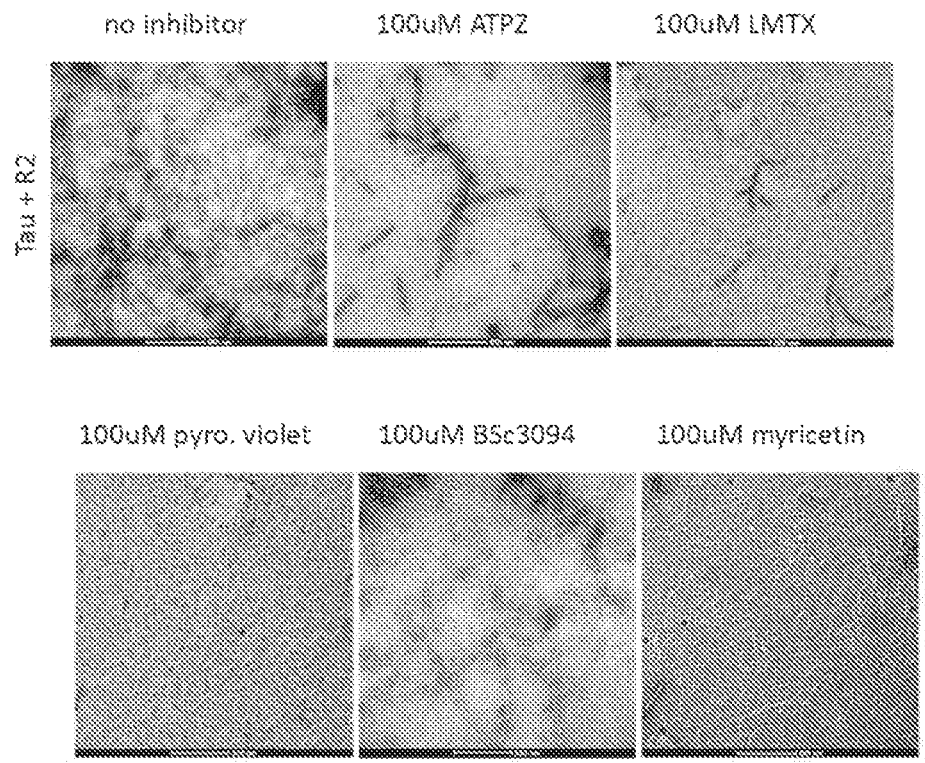

Strikingly, glial cells (i.e. MAP2 negative) significantly uptake the protein and show ThS-positive dots that partially co-localize with the Tau signal (FIGS. 16 and 17, dashed red rectangles). This suggests that glial cells may have a role in clearing the extracellular space from Tau and Tau-derived aggregates, potentially protecting neurons, but could also participate in the pathological phenotype. In fact, glial Tau pathology has been reported alongside neuronal Tau pathology, whereby the ratio of glial to neuronal pathology differs between diseases. Glial Tau pathology is mostly observed in oligodendrocytes and astrocytes and in some cases in microglia. Although glial cells are important in the cleaning of the extracellular space and are regarded as the major waste disposal machinery of the brain, they are also crucial for the normal brain physiology, and several of glia functions have been shown to be disrupted in the presence of Tau fibrils. The results presented herein further suggest an important role of glial cells in Tau pathology, although their protective versus detrimental role remain to be determined.

Taken together, this body of data shows that R2 seeds and R2-seeded Tau and K18 induce the aggregation of endogenous Tau in primary neurons, and that R2-seeded Tau and K18 might have detrimental effects on the neuronal cells. The uptake capacity of R2 seeds is low, but can be significantly enhanced by replacing the seeds with the version that already seeded Tau or K18. The subsequent seeding is most prominent when the cells overexpress Tau, K18 or an aggregation-prone mutant thereof. This is likely due to 1. The availability of excess monomeric protein; 2. The absence of seeding barriers that may exist between Tau originated from different species (the primary neurons are rat). Most interestingly, glial cells take up a large amount of fibrils, suggesting that they may play a role in excess Tau fibrils clean up.

Next, a proof of concept experiment aimed at demonstrating that the rPHFs can be potentially used in drug screening assays was designed. To do so, R2 seeds were incubated with monomeric Tau protein in presence or absence of a set commercially available know Tau aggregation inhibitors (ATPZ, LMTX, Pyrochatecol violet, BSc3094 and myricetin, FIG. 18 a) at three different conventions (1 μM, 10 μM and 100 μM). The aggregation kinetic was followed using ThS fluorescence. As an example, the full kinetic of Tau incubated in presence of R2 seed, with LMTX at the three different concentration is presented in FIG. 18 b. For LMTX as well as all the other inhibitor tested (FIGS. 18 c and d), a dose-dependent inhibitions were observed, although the inhibitors show various inhibition potencies (e.g. low for BSc3094, high for LMTX). EM micrographs confirm the absence of significant fibrillization in the presence of the inhibitors inhibitor. The presence of oligomeric species corroborate the hypothesis that Tau is locked in OFF-pathway conformations.

It is herein demonstrated that the R2 peptide is capable of seeding full-length Tau, leading to the formation of filaments that morphologically resemble native PHFs. This has tremendous potential applications in understanding the basic biophysical properties of the PHFs and their seeding mechanisms, but also as a tool to allow the design of imaging probes or the screening for modulators of PHFs formation and clearance. Indeed, while native PHFs can only be obtained at low amounts, following relatively harsh extraction protocols that are likely to affect their biophysical and biological properties and could introduce structural and morphological changes that do not reflect their native properties, the possibilities of obtaining large amounts of pure rPHFs fibrils using R2 peptide fibrils as seed could provide unlimited amounts of highly pure rPHFs fibrils for mechanistic, diagnostic and therapeutic purposes.

Several characteristics of the rPHFs were evaluated, such as their morphological dimensions and capacity to be taken up by cells and induce seeding of endogenous protein. The rPHFs described herein have a general morphology and cellular properties that are comparable to that of native PHFs.

Using a library of peptides derived from R2, the sequence determinants of R2 aggregation and seeding of Tau could be determined. It is herein reported that only the full sequence of R2 leads to the formation of PHFs-like fibrils, although several shorter fragments are capable of aggregation and seeding, suggesting that several sub-domains of R2, such as the PHF6* and the 'KDNIK' β-sheets, the 'SN' turn, and the cysteine, in their specific arrangement in R2, act in concert and are therefore all required for the formation of PHFs-like fibrils. In agreement with this hypothesis, several longer R2 fragments were able to seed Tau into rPHFs, provided the seed morphology was not significantly affected by the modified sequence (as in the case of R2R3 or R2 ΔK280).

Although the R2 fibrils are morphologically distinct from the R2-seeded Tau, it does not necessarily imply that the seeding does not involved templating. Indeed, the morphological differences between R2 fibrils and R2-seeded Tau fibrils might originate from physical constrains on the full length protein that lead to the formation of fibrils of an apparently different morphology compared to that of the seeds themselves, while the core of the Tau that directly interact with the folded peptide assumes the same morphology. Therefore, the final morphology should not be expected to be the same as that of R2 fibrils, since the other segments of Tau have important roles in modulating the aggregation and the final structure and morphology of Tau fibrils. Corroborating this hypothesis, K18 seeding by R2 results in the formation of helical twisted filaments, which however do not present the highly ordered twisted helical structure harbored by PHFs, suggesting that specific structural elements outside R2 and also outside K18 influence the final folding of the full length protein.

Taken together, the results presented herein show the importance of R2 seeding of the full length Tau in understanding the aggregation behavior of Tau, and point toward the possible use of R2-seeded Tau as a good model to study the behavior of native PHFs. The fact that the fibrils have a morphology that is similar to that of native PHFs suggests that R2-seeded fibrils could provide a powerful platform to investigate the sequence, molecular and structural determinants of NFT formation and clearance in vitro under conditions that are known to influence AD pathology and pathogenesis.

An aspect of the invention provides a method for preparing PHFs-like Tau aggregates comprising:
(a) contacting R2 fragments consisting of SEQ ID NO: 1 or comprising SEQ ID NO: 1 with polyanions,
(b) allowing formation of R2 fibrils,
(c) breaking down the R2 fibrils into seeds,
(d) contacting Tau proteins comprising SEQ ID NO: 1 with the R2 fibrils seeds under conditions which allow Tau aggregation.

In a preferred embodiment, R2 fragments comprising SEQ ID NO: 1 are any R2 construct/iso form/variant/mutant/modified peptide comprising the R2 sequence SEQ ID NO: 1. Preferably, such R2 construct/isoform/variant/mutant/modified peptide comprising the R2 sequence SEQ ID NO: 1 has amino acid sequence selected from the group comprising SEQ ID NO: 2, SEQ ID NO: 3, SEQ ID NO: 4 or combination thereof.

In another preferred embodiment, polyanions are selected from the group comprising heparin, arachidonic acid, polysulfates, DNA, RNA, fatty acid micelles or negatively charged surfaces.

In a further preferred embodiment, the step (c) is carried out by various known techniques such as tip/bath sonication, freeze and thaw cycles, strong shaking.

In a further preferred embodiment, Tau proteins comprising SEQ ID NO: 1 are any Tau construct/iso form/variant/mutant/modified protein comprising the R2 sequence SEQ ID NO: 1. Preferably, such Tau construct/isoform/variant/mutant/modified protein comprising the R2 sequence SEQ ID NO: 1 is selected from the group comprising the full length Tau protein 4R2N (SEQ ID NO: 5), Tau microtubule binding domain (K18) (SEQ ID NO: 6), Tau protein 4R1N (SEQ ID NO: 7), Tau protein 4R0N (SEQ ID NO: 8), mouse Tau isoforms m4R2N (SEQ ID NO: 9), m4R0N (SEQ ID NO: 10) or combination thereof.

The invention also includes mutants or variants of the R2 fragments and the Tau proteins of the invention, as disclosed above, any of whose residues may be changed from the corresponding residues shown in SEQ ID NOs: 1 to 10 while still maintaining its activity and physiological functions.

In some embodiments, the present invention is also directed to variants of the R2 fragments and the Tau proteins of the invention, as disclosed above. The term "variant" refers to a peptide, a polypeptide or a protein having an amino acid sequence that differs to some extent from native SEQ ID NOs: 1 to 10 and which is an amino acid sequence that vary from the native sequences by conservative amino acid substitutions, whereby one or more amino acids are substituted by another with same characteristics and conformational roles. The amino acid sequence variants possess substitutions, deletions, side-chain modifications and/or insertions at certain positions within the amino acid sequence of the native amino acid sequence as set forth in SEQ ID NOs: 1 to 10. Conservative amino acid substitutions are herein defined as exchanges within one of the following five groups:
I. Small aliphatic, nonpolar or slightly polar residues: Ala, Ser, Thr, Pro, Gly
II. Polar, positively charged residues: His, Arg, Lys
III. Polar, negatively charged residues: and their amides: Asp, Asn, Glu, Gln
IV. Large, aromatic residues: Phe, Tyr, Trp
V. Large, aliphatic, nonpolar residues: Met, Leu, Ile, Val, Cys.

Typically, according to the method of the invention, SEQ ID NOs: 1 to 4 are capable of forming fibrils when mixed with heparin at molar ratio 1:4 and incubated at 37° C. for at least 12 h, with or without shaking. To obtain seeds, sonication is performed using a tip sonicator (at least 3 pulses, amplitude to be determined depending on the sonicator). A detailed protocol for preparing the R2 (SEQ ID NO: 1) and alternative peptides (SEQ ID NO: 2 to 4) seeds is described in FIG. 2. To obtain rPHFs, the obtained seeds are mixed with Tau at molar ratio of 1:1 and incubated at 37° C. under quiescent conditions for at least 12 h, to form rPHFs. A detailed protocol for the preparation of rPHFs is provided in FIG. 3.

The proteins, fragments thereof (such as K18) and peptides of the invention may be produced recombinantly using a polynucleotide sequence that encodes Tau and/or a fragment thereof or may be produced by biochemical or synthetic techniques. For example, Tau proteins, fragments thereof and peptides of the invention can be expressed in corresponding test systems that comprise animals, preferably transgenic animals, and/or cell or tissue culture systems or bacterial expression systems as described herein (for example see Examples). Preferably, said transgenic animal and/or cell or tissue culture system expresses an amino acid molecule as shown in any one of SEQ ID NOs: 1 to 10. These techniques and methods are known to those of ordinary skill in the art (see, e.g. Sambrook et al., Molecular Cloning: A Laboratory Manual, Cold Spring Harbor Laboratory Press, Cold Spring Harbor, N.Y., 1989; Merrifield, J. Am. Chem. Soc. 85 (1963), 2149-2146; Stewart, "Solid Phase Peptide Synthesis", WH Freeman Co, San Francisco (1969); Scopes, "Protein Purification", Springer Verlag, New York, Heidelberg, Berlin (1987); Janson, "Protein Purification, Principles, High Resolution Methods and Applications", VCH Publishers, New York, Weinheim, Cambridge (1989); Wrede, "Concepts in Protein Engineering and Design", Walter de Gruyter, Berlin, New York (1994)).

It is important to note that post-translational modifications, such as tyrosine phosphorylation and acetylation mimetic, do not affect the capacity of Tau proteins of the invention to form rPHFs in presence of R2 seeds. Furthermore, site-specific enzyme-mediated introduction of post-translational modifications into PHF-like Tau aggregates of the invention are still possible and could be used to prepare rPHFs with a specific desired set of PTMs. This is not possible in the case of the native Tau aggregates as they are composed of heterogeneous PHFs that are heavily modified at multiple sites.

Schematic preparation of rPHFs is shown on FIG. 5. According to an embodiment, the R2 (SEQ ID No 1) or R2-derived peptides fibrils (SEQ ID No 2 to 4) are prepared at a concentration of 100 µM in 10 mM phosphate, 50 mM NaCl, supplemented with 0.5 mM fresh DTT, and are incubated for at least 12 h at 37° C. in the presence of 25 µM heparin. The peptides concentration may be modified, but the molar ratio to heparin must remain at about from 1:3 to 1:5, preferably close to 1:4 (heparin:peptide). The buffer may be modified but the pH should remain in the range 5-9, preferably 7-8, the ionic strength between 50 and 150 mM and the presence of at least 0.5 mM fresh DTT is required. Buffer conditions outside these ranges have not been systematically studied. Once the fibrils are formed, buffer may be exchanged for a buffer without DTT. However, the presence of heparin is still required for the subsequent steps, and must be added in the alternative buffer. The R2 or R2-derived fibrils can be kept at 37° C. or RT at least two weeks, but should not be frozen. The R2 (SEQ ID No 1) or R2-derived fibrils (SEQ ID No 2 to 4) are sonicated so that they break down into smaller species (i.e. the seeds) that can efficiently seed the formation of rPHFs by Tau, using a tip sonicator. Sonication is performed for at least 3×1 sec, with an amplitude that depends upon the sonicator. Increasing the number of pulses and sonication amplitude will decrease the length of the seeds, without releasing a detectable quantity of monomeric peptide which may favor seeding capacity. Sonication may be coupled with freeze/thaw cycles and/or vortexing, to decrease the length of the seeds. Seeding of monomeric Tau should be performed immediately following sonication. Freshly dissolved monomeric Tau is mixed with the sonicated R2 seeds at a ratio 1:1 (Tau:R2, 10 µM:10 µM), and further incubated for at least 12 h at 37° C. under quiescent conditions, but can be further kept at 3° C. or RT for at least two weeks. Standard buffer is 10 mM phosphate pH 7.4, 50 mM NaF and 0.5 mM fresh DTT. The buffer may be modified but the pH should remain in the range 7-8, the ionic strength between 50 and 150 mM and the presence of 0.5 mM DTT is not required. Buffer conditions outside these ranges have not been systematically studied. Once the fibrils are formed, buffer may be exchanged for a buffer outside these ranges, such as water or 0.5M NaCl-containing buffers.

Another aspect of the present invention provides a use of R2 fragments consisting of SEQ ID NO: 1 or comprising SEQ ID NO: 1 for preparing rPHFs Tau aggregates. In a preferred embodiment, R2 fragments comprising SEQ ID NO: 1 have amino acid sequence selected from the group comprising SEQ ID NO: 2, SEQ ID NO: 3, SEQ ID NO: 4 or combination thereof.

A further aspect of the present invention provide R2 fibrils obtained by the method of the present invention.

Another aspect of the present invention provides PHFs-like Tau aggregates obtained by the method of the present invention.

A further aspect of the present invention provides a composition comprising R2-seeded fibrils obtained by the method of the present invention.

Another aspect of the present invention provides a composition comprising PHFs-like Tau aggregates obtained by the method of the present invention.

A further aspect of the present invention provides a kit for preparing PHFs-like Tau aggregates comprising R2 fibrils obtained by the method of the invention, Tau proteins comprising SEQ ID NO: 1 and instructions for use. In a preferred embodiment, Tau proteins comprising SEQ ID NO: 1 are any Tau construct/isoform/variant/mutant/modified protein comprising the R2 sequence SEQ ID NO: 1. Preferably, such Tau construct/isoform/variant/mutant/modified protein comprising the R2 sequence SEQ ID NO: 1 is selected from the group comprising the full length Tau protein 4R2N (SEQ ID NO: 5), Tau microtubule binding domain (K18) (SEQ ID NO: 6), Tau protein 4R1N (SEQ ID NO: 7), Tau protein 4R0N (SEQ ID NO: 8), mouse Tau isoforms m4R2N (SEQ ID NO: 9), m4R0N (SEQ ID NO: 10) or combination thereof.

Furthermore, the kit for preparing PHFs-like Tau aggregates may also comprise a carrier means being compartmentalized to receive in close confinement one or more container means such as vials, tubes and the like, each of the container means comprising one of the separate elements to be used in the method of the invention. For example, one of the container means may comprise the Tau proteins as defined herein, soluble or bound to a carrier. A second container may comprise soluble Tau protein(s) as defined herein, in lyophilized form or in solution. Another container may comprise R2-seeded fibrils as defined herein. Further container may comprise reagents, such as heparin.

Another aspect of the present invention provides a method for identifying compounds that are inhibitors of Tau aggregation, propagation and/or toxicity comprising:
(a) contacting Tau proteins comprising SEQ ID NO: 1 and R2 fibrils of the invention in the presence and absence of a test compound under conditions which allow Tau protein aggregation, propagation and/or toxicity effects,
(b) determining the amount of PHFs-like Tau aggregates formed in the presence and absence of the test compound, and
(c) comparing the amount of PHFs-like Tau aggregates formed in the presence of the test compound with the amount of PHFs-like Tau aggregates formed in the absence of the test compound wherein a test compound which decreases the amount of PHFs-like Tau aggregates formed, decreases PHFs-like Tau propagation and/or decreases PHFs-like Tau toxic effect is an inhibitor.

In a preferred embodiment, Tau proteins comprising SEQ ID NO: 1 are any Tau construct/iso form/variant/mutant/modified protein comprising the R2 sequence SEQ ID NO: 1. Preferably, such Tau construct/isoform/variant/mutant/modified protein comprising the R2 sequence SEQ ID NO: 1 is selected from the group comprising the full length Tau protein 4R2N (SEQ ID NO: 5), Tau microtubule binding domain (K18) (SEQ ID NO: 6), Tau protein 4R1N (SEQ ID NO: 7), Tau protein 4R0N (SEQ ID NO: 8), mouse Tau isoforms m4R2N (SEQ ID NO: 9), m4R0N (SEQ ID NO: 10) or combination thereof.

The compounds of the invention that are inhibitors of Tau protein aggregation are compounds that can either inhibit or completely inhibit Tau protein aggregation, or delay Tau protein aggregation. Furthermore, the compounds of the invention that are inhibitors of Tau protein aggregation are also compounds that can alter, inhibit, or delay the process of PHF-nucleation, PHF-elongation or the process of first dimerization which may lead to a nucleation site for PHFs formation. The activity of an inhibitor may be measured, for example, by testing PHFs-like Tau aggregates formation in an assay comprising the compound to be screened and in a parallel assay wherein, under the same in vitro conditions, said compound is omitted and/or replaced by an irrelevant compound, like, lysozyme, BSA, tubulin, hemoglobin, etc. Furthermore, the compounds of the invention that are inhibitors of Tau protein propagation are also compounds that can alter, inhibit, or delay the process of Tau protein propagation. Furthermore, the compounds of the invention that are inhibitors of Tau protein toxicity are also compounds that can alter, inhibit, delay, suppress, mitigate the Tau protein toxicity.

A further aspect of the present invention provides use of PHFs-like Tau aggregates obtained by the method of the present invention for use in screening assays to identify compounds that bind to the PHF or native Tau aggregates.

Another aspect of the present invention provides use of PHFs-like Tau aggregates obtained by the method of the present invention for preparing in vivo imaging agents that bind native Tau aggregates.

Typically, the "in vivo imaging agents" of the invention are compounds, which can be detected following their administration to the human or animal body in vivo. The in vivo imaging agent of the invention comprises a PHFs binder labelled with an in vivo imaging moiety. The term "labelled with an in vivo imaging moiety" means either (i) that a particular atom of the PHFs binder is an isotopic version suitable for in vivo detection, or (ii) that a group comprising said in vivo imaging moiety is conjugated to said PHFs binder.

An "in vivo imaging moiety" may be detected either externally to the human body, or via use of detectors designed for use in vivo, such as intravascular radiation or optical detectors such as endoscopes, or radiation detectors designed for intra-operative use.

Following the administration into the human body, the in vivo imaging agent is allowed to bind to PHFs or other pathological Tau aggregates with PHF-like properties in the brain of said human subject. For example, when the human subject is an intact subject, the in vivo imaging agent will dynamically move through the human body, coming into contact with various tissues therein. Once the in vivo imaging agent comes into contact PHF, a specific interaction takes place such that clearance of the in vivo imaging agent from tissue with PHFs takes longer than from tissue without, or with less PHFs. A certain point in time will be reached when detection of in vivo imaging agent specifically bound to PHFs is enabled as a result of the ratio between in vivo imaging agent bound to tissue with PHFs versus that bound in tissue without, or with less pPHFs. An ideal such ratio is at least 2:1.

The detection of signals emitted by the in vivo imaging moiety can be done either externally to the human body or via use of detectors designed for use in vivo and depends on the nature of the signals emitted. Therefore, where the signals come from a paramagnetic metal ion, magnetic resonance imaging (MRJ) is used, where the signals are gamma rays, single photon emission tomography (SPECT) is used, where the signals are positrons, positron emission tomography (PET) is used, and where the signals are optically active, optical imaging is used. All are suitable for use in the method of the present invention, with PET and SPECT are preferred, as they are least likely to suffer from background and therefore are the most diagnostically useful.

The imaging agents of the invention can be used for monitoring a tauopathy progression and/or to monitor the efficacy of tauopathy treatment. Tauopathy is a neurodegenerative diseases associated with the pathological aggregation of Tau protein in neurofibrillary or gliofibrillary tangles or other pathological aggregation forms in a subject brain, preferably in the human brain. Tangles are formed by hyperphosphorylation and/or disassociation of Tau from microtubules, causing it to aggregate in an insoluble forms, including hyperphosphorylated Tau paired helical filaments) . Tauopathy is preferably a condition in which neurofibrillary tangles (NFT) are predominantly observed. Tauopathy is preferably selected from the group comprising frontotemporal dementia (FTD), frontotemporal dementia with parkinsonism linked to chromosome 17 (FTDP-17, Alzheimer's disease (AD), progressive supranuclear palsy (PSP), corticobasal degeneration (CBD), Pick's disease (PiD), argyrophilic grain disease (AGD), chronic traumatic encephalopathy (CET), and frontotemporal lobar degeneration.

A further aspect of the present invention provides an inhibitor identified or obtained by the method of the present invention.

Potential inhibitors to be screened with the method of the present invention include small molecules which bind to, interfere with and/or occupy relevant sites on Tau proteins as defined herein or on aggregated Tau fragments bearing the R2 domain or on R2 and thereby block R2 association with Tau monomers. In addition, potential inhibitors to be screened with the method of the present invention include small molecules which bind to, interfere with and/or occupy relevant sites on the R2 in the aggregated form and block Tau monomer addition and fibril growth. In particular, said inhibitors may interfere with the potential β-sheet formation stretch of Tau proteins as defined herein or with the seeding process. Such inhibitors comprise also molecules, which bind to other parts of the full-length Tau sequence but inhibit the correct folding of said Tau protein (and/or fragments thereof) and thereby inhibit the formation of correct β-structures. Said molecules might be selected prior to employing the method of the present invention, for example, by well known ELISA tests, and/or other screening methods like spot membrane binding assays. Further screening methods for "pre-screening" are well known in the art and comprise, for example, the screening of phage display libraries. Examples of small molecules include, but are not limited to organic cyclic molecules (as documented in the Examples), small peptides or peptide-like molecules.

Another aspect of the present invention provides a composition comprising the inhibitor as identified or obtained by the method of the present invention.

The term "composition" as used in accordance with the present invention comprises (1) at least one inhibitor as identified or obtained by the method of the invention, and/or (2) at least one inhibitor which specifically binds to a Tau protein as defined herein, and/or (3) at least one antibody of the present invention, and/or (4) optionally, further molecules, either alone or in combination, like for example molecules which are capable of interfering with the formation of neurofibrillary tangles and/or the formation of amyloid plaques. The composition may be in solid, liquid or gaseous form and may be, for example, in a form of (a) powder(s), (a) tablet(s), (a) solution(s) or (an) aerosol(s). In a preferred embodiment, said composition comprises at least two, preferably three, more preferably four, most preferably five inhibitors as defined herein above. In a preferred embodiment, said composition is a diagnostic or a pharmaceutical composition.

The pharmaceutical composition may further comprise a pharmaceutically acceptable carrier, excipient and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, for example, by intravenous, intraperitoneal, subcutaneous, intramuscular, topical, intradermal, intranasal or intrabronchial administration. Most preferably, said administration is intra-cerebral and/or by an administrative route which by-passes the blood/brain barrier.

The dosage regimen will be determined by the attending physician and clinical factors. As is well known in the medical arts, dosages for any one patient depends upon many factors, including the patient's size, body surface area, general health, age, sex, the particular compound to be administered, time and route of administration, and other drugs being administered concurrently. Dosages can vary depending on the relative potency of individual compositions, and can generally be estimated based on data obtained from in vitro and in vivo animal models. Typically, the dosage may be from about 0.01 micrograms to about 100 g per kg of body weight, and may be given once or more daily, weekly, or even less often. Following successful administration, it may be desirable to have the subject undergo additional booster administrations to maintain a suitable level of the anti-Tauoligomer, Taufragment, or tau-peptide activity. For example, an additional dosage can be administered 6, 12, 24, 36, 48, 60 or more months after an initial dosage. In some cases, additional dosages can be administered every 6, 12, 18, 24, 30, 36, 42, 48, 54, 60 or more months after an initial dosage. Additional dosages also can be administered as needed.

The compositions of the present invention may be administered locally or systemically. Administration will generally be parenterally, e.g., intravenously. The compositions of the invention may also be administered directly to the target site, for example, by biolistic delivery to an internal or external target site (like the brain) or by catheter to a site in a (brain) artery. Furthermore, the pharmaceutical composition of the invention may comprise further agents, depending on the intended use of the pharmaceutical composition. Such agents may be drugs acting on the central nervous system, like neuroprotective factors, cholinesterase inhibitors, agonists of Ml muscarinic acetylcholine receptor, drugs leading to increased synthesis of acetylcholine, as well as non-steroid antiinflammatory drugs (NSAIDs), hormones, antioxidants, inhibitors of the production and/or aggregation of Aβ, or inhibitors of the production, aggregation and/or phosphorylation of tau. Further drugs/agents, which may be comprised in the pharmaceutical composition of this invention, comprise any Alzheimer-relevant medication.

The pharmaceutical compositions, as well as the methods of the invention described herein or the uses of the invention described herein can be used for the treatment of all kinds of diseases hitherto unknown or being related to or dependent on pathological Tau aggregation. They may be particularly useful for the treatment of Alzheimer's disease and other diseases where intracellular deposits of Tau, like frontotemporal dementia, FTDP-17-mutations and other tauopathies, appear to play a role. They may be desirably employed in humans, although animal treatment is also encompassed by the methods, uses and compositions described herein.

Pharmaceutical compositions for use in accordance with the present application may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

A further aspect of the present invention provides a use of R2 fragment consisting of SEQ ID NO: 1 or comprising SEQ ID NO: 1 for screening and/or for the identification of an inhibitor, capable of modifying PHFs formation.

In a preferred embodiment, R2 fragments comprising SEQ ID NO: 1 have amino acid sequence selected from the group comprising SEQ ID NO: 2, SEQ ID NO: 3, SEQ ID NO: 4 or combination thereof.

The term "PHFs formation" as used in the context of the present invention means the assembly of Tau protein of the invention into paired helical filaments, wherein said paired helical filaments do not only comprise bona fide PHFs but also thin filaments of Tau protein or fragments thereof which may serve as nuclei and/or nucleation sites which can efficiently promote the assembly of bona fide PHFs from Tau fragments, Tau constructs and/or intact Tau. Furthermore, the term "PHFs formation" comprises also PHFs aggregations and aggregation of peptides comprising Tau-fragments. The aggregation of said peptides comprising a specific Tau derived peptide as defined herein as well as the dimerization of said peptide is also comprised in said term. Similarly, the term "aggregation products" comprises any aggregation, interaction, assembly and/or dimerization of said peptides. Said "aggregation products" may be measured during their formation and/or as final reaction product. Methods for the measurement of PHFs formation and/or the formation of aggregation products are well known in the art.

The term "modifying the PHFs formation" as used herein is not limited to (complete) "inhibiting" but also comprises "delaying" the PHFs formation. The term furthermore comprises the alteration which may occur during PHFs-nucleation, PHFs-elongation or even during first dimerization processes which may lead to a nucleation site for PHFs formation. A "modified PHFs formation" may be measured, for example, by testing said PHFs-formation in an assay comprising the compound to be screened and in a parallel assay wherein, under the same in vitro conditions, said compound is omitted and/or replaced by an irrelevant compound, like, lysozyme, BSA, tubulin, hemoglobin, etc.

Another aspect of the present invention provides a kit for testing inhibitors of Tau protein aggregation comprising R2 fibrils obtained by the method of the invention, Tau proteins comprising SEQ ID NO: 1 and instructions for use.

In a preferred embodiment, Tau proteins comprising SEQ ID NO: 1 are any Tau construct/iso form/variant/mutant/modified protein comprising the R2 sequence SEQ ID NO: 1. Preferably, such Tau construct/isoform/variant/mutant/modified protein comprising the R2 sequence SEQ ID NO:

1 is selected from the group comprising the full length Tau protein 4R2N (SEQ ID NO: 5), Tau microtubule binding domain (K18) (SEQ ID NO: 6), Tau protein 4R1N (SEQ ID NO: 7), Tau protein 4R0N (SEQ ID NO: 8), mouse Tau isoforms m4R2N (SEQ ID NO: 9), m4R0N (SEQ ID NO: 10) or combination thereof.

Furthermore, the kit for testing inhibitors of Tau protein aggregation may comprise a carrier means being compartmentalized to receive in close confinement one or more container means such as vials, tubes and the like, each of the container means comprising one of the separate elements to be used in the method of the invention. For example, one of the container means may comprise the Tau proteins as defined herein, soluble or bound to a carrier. A second container may comprise soluble Tau protein(s) as defined herein, in lyophilized form or in solution. Another container may comprise R2-seeded fibrils as defined herein. Further container may comprise reagents, such as heparin.

Another aspect of the present invention provides a method for reducing the spread of Tau aggregation in the brain of a subject, the method comprising administering a pharmacologically effective amount of the inhibitor of the invention to the subject.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

The foregoing description will be more fully understood with reference to the following Examples. Such Examples, are, however, exemplary of methods of practising the present invention and are not intended to limit the scope of the invention.

EXAMPLES

K18 Constructs

K18 (SEQ ID No: 6) in pT7-7 was expressed in *E. coli* strain BL21 and purified following a protocol adapted from BARGHORN S. et al, AMYLOID PROTEINS SPRINGER (2005). Briefly, cells were broken by sonication in IEX buffer B (10 mM HEPES, pH 6.5, 1 mM $MgCl_2$, 20 mM NaCl, 1 mM DTT, 1 mM PMSF). After centrifugation at 40,000 g for 30 min, the supernatant was boiled until the solution became cloudy (~5 min) and centrifuged again for 30 min. The supernatant was filtered and loaded on a cation-exchange column (MonoS, GE Healthcare), and the protein was eluted using a salt gradient (increasing the NaCl concentration of IEX buffer B from 20 mM to 1 M NaCl over 20 column volumes). Fractions containing the K18 fragment were immediately loaded on a reverse phase HPLC C4 column (PROTO 300 C4 10 μm, Higgins Analytical; buffer A: 0.1% TFA in water, buffer B: 0.1% TFA in acetonitrile), and the protein was eluted using a gradient from 30 to 40% buffer B over 40 min (15 ml/min).

Human Tau Isoforms

All Tau isoforms in pET-28a(+) (4R-Tau isoforms 4R2N, 4R1N and 4R0N, respectively SEQ ID No 5, 7 and 9, as well as 3R-Tau isoforms 3R2N, 3R1N and 3R0N) were grown in *E. coli* until the OD reached 0.6-0.8, after which the cultures were cooled down and induced overnight at 18° C., with 0.4 mM IPTG. Cells were pelleted and broken by sonication in lysis buffer (10 mM HEPES pH 6.5, 20 mM NaCl supplemented with 1 mM EDTA 0.5 mM fresh DTT, 1 mM PMSF and 1 tablet of protease inhibitor cocktail). The lysate was cleared by centrifugation at 40'000 g for 30 min. The supernatant was filtered and loaded on a 5 ml cation-exchange column (HiTrap, GE Healthcare) and the protein was eluted using a salt gradient (increasing the salt concentration of IEX buffer A from 20 mM NaCl (IEX buffer A: 10 mM HEPES pH 6.5, 20 mM NaCl supplemented with 1 mM EDTA 0.5 mM fresh DTT) to IEX buffer B at 1 M NaCl (IEX buffer B: 10 mM HEPES pH 6.5, 1 M NaCl supplemented with 1 mM EDTA 0.5 mM fresh DTT) over 12 column volumes). Fractions were analyzed by SDS-PAGE and those containing the protein were pooled and loaded on a reverse phase HPLC C4 column (PROTO 300 C4 10 μm, Higgins Analytical; buffer A: 0.1% TFA in water, buffer B: 0.1% TFA in acetonitrile), and the protein was eluted using a gradient from 30 to 40% buffer B over 40 min (15 ml/min). Final protein purity was then assessed by LCMS ESI, UPLC, and SDS-PAGE (Coomassie).

Mouse Tau Isoforms

Mouse Tau isoforms m4R2N, m4R0N and m3R0N in pET-28a (+) containing a C-terminal 6×His tag followed by a SUMO tag were grown in *E. coli* until the OD reached 0.6-0.8, after which the cultures were cooled down and induced overnight at 18° C., with 0.4 mM. Cells were pelleted and broken by sonication in lysis buffer (50 mM Tris pH8.0, 15 mM imidazole, 500 mM NaCl supplemented with 0.5 mM fresh DTT, 1 mM PMSF and 1 tablet of protease inhibitor cocktail). The lysate was cleared by centrifugation at 40,000 g for 30 min. The supernatant was filtered and loaded on a 5 ml HisTrap column (HisTrap, GE Healthcare) and the protein was eluted using an imidazole gradient (increasing the imidazole concentration of buffer A from 15 mM imidazole (buffer A: 50 mM Tris pH8.0, 15 mM imidazole, 500 mM NaCl supplemented with 0.5 mM fresh DTT) to buffer B at 500 mM imidazole (buffer B: 50 mM Tris pH 8.0, 500 mM imidazole, 500 mM NaCl supplemented with 0.5 mM fresh DTT) over 12 column volumes). Fractions were analyzed by SDS-PAGE and those containing the fusion protein were cleaved by ULP1 for 1 h at RT to remove the histidine tag and the SUMO, and loaded on a reverse phase HPLC C4 column (PROTO 300 C4 10 μm, Higgins Analytical; buffer A: 0.1% TFA in water, buffer B: 0.1% TFA in acetonitrile), and the protein was eluted using a gradient from 30 to 40% buffer B over 40 min (15 ml/min). Final protein purity was then assessed by LCMS ESI, UPLC, and SDS-PAGE (Coomassie).

SH2-CD c-Abl Purification

Recombinant SH2-CD c-Abl, T231R and YopH were co-overexpressed and SH2-CD c-Abl purified from *E. coli*. Briefly, cells were grown in 2 L of TB media, until the OD reached 1.0, after which the cultures were cooled down and induced overnight at 18° C., with 0.2 mM IPTG. The cells were then lysed by sonication in HisTag binding buffer HA (50 mM Tris pH 8, 500 mM NaCl, 5% Glycerol, 25 mM imidazole) and centrifuged twice at high speed (50 000 g, 20 min, 4° C.), before being injected in 5 mL HisTag columns (histrap 5 mL column, GE Healthcare, buffer HA: same as above, buffer HB: same as HA with 0.5 M imidazole). Selected fractions were desalted using two HiPrep 26/10 desalting columns (GE Healthcare) in series (Desalting buffer: 20 mM Tris pH 8, 50 mM NaCl, 5% Glycerol, 1 mM DTT), combined and further purified by anion-exchange chromatography using a MonoQ 5/50 GL column (GE Healthcare, buffer A: 20 mM Tris, 5% Glycerol, 1 mM DTT, pH 8.0, buffer B: same as buffer A with 1 M NaCl). The final concentration of the c-Abl kinase was determined using the UV absorbance at 280 nm (M=46797 g·mol-1 and $\varepsilon_{280}$=80010 $M^{-1} \cdot cm^{-1}$).

Large Scale Preparation of Phosphorylated Tau and Y→F Mutants by c-Abl

The large scale phosphorylation of 10 mg Tau and Tau Y→F mutants were performed for 4 h in 50 mM Tris, 5 mM $MgCl_2$, 1 mM DTT, 20 mM $Na_3VO_4$ (phosphatase inhibitor) in the presence of 3 mM MgATP, pH, 7.5 at 30° C. c-Abl kinase was used at a ratio of 1:20 (kinase:Tau). The reaction mixture was followed by ESI-MS to verify the completion of the phosphorylation. Additional kinase and MgATP were added when needed. Phosphorylated K18, Tau and Y→F mutants were purified by reverse-phase HPLC preparative C4 column (PROTO 300 C4 10 µm Higgins Analytical; buffer A: 0.1% TFA in water, buffer B: 0.1% TFA in acetonitrile) using a linear gradient of 30 to 40% of B in 40 min. Pure fractions were pooled and lyophilized.

Preparation of Heparin-Induced Tau and K18 Fibrils

Fibrils of WT, mutants and phosphorylated Tau (SEQ ID No: 5, 7 and 9) and K18 (SEQ ID No: 6) were formed by incubating monomeric protein in 10 mM phosphate, pH 7.4, 50 mM NaF and 0.5 mM DTT with heparin sodium salt (Applichem GmbH) at a molar heparin:protein ratio of 1:4 under constant orbital agitation (1000 rpm, Peqlab, Thriller) for at least 1 day at 37° C.

Self-Assembly of R2 or R2-Derived Peptides

Unless stated otherwise, 100 µM R2 or R2-derived peptide were dissolved in 10 mM phosphate, 50 mM NaF, 0.5 mM DTT and pH-adjusted to 7.4. The solution was then vortexed and the supernatant was incubated in presence of heparin sodium salt at molar ratio 1:4 (heparin:peptide) (Applichem GmbH) at 37° C., either with or without constant orbital agitation (1000 rpm, Peqlab, Thriller).

Seeding of Tau (SEQ ID No 5, 7 and 8), K18 (SEQ ID No 6) or α-Syn with R2 (SEQ ID No 1) or R2-Derived (SEQ ID No 2 to 4) Peptides 100 µM of R2, R2-derived peptides fibrils prepared as described above were mechanically reduced in size by sonication (Sonics VibraCell) with a fine tip for at least 3×1 s at an amplitude of 40%. The obtained seeds were added at a final concentration of 10 µM to 10 µM of monomeric Tau or K18 in 10 mM phosphate, 50 mM NaF, 0.5 mM DTT and incubated 37° C.

Rat Primary Hippocampal Neuron Culture.

Hippocampi from PO WT rat (OFA SD, Charles River) were dissociated and triturated in papain-containing medium. After centrifugation at 400 g for 2 min, neurons were plated in MEM supplemented with 10% fetal calf serum (FCS) on Cultrex™ poly-L-lysine (Trevigen)-coated coverslips at 1.5×105 cells/ml (6 well-plates, 3 ml per well). After 4 h, medium was replaced with Neurobasal/B27 medium. Viral infections were performed two weeks, and transfection one week after plating.

Immunocytochemistry in Rat Primary Neurons

One week old hippocampal rat primary neurons seeded on coverslips coated with Cultrex poly-L-lysine were transfected with Tau or K18 ΔK280 (2 ng/well) using lipofectamine 2000 reagent (Invitrogen). 24 h after transfection, cells were treated with 1 µM monomeric R2, R2 seeds, R2-seeded Tau, R2-seeded K18 and further incubated for 1 or 3 days. Cells were then fixed in 100% methanol at −20° C. for 10 min and rinsed three times in PBS. After blocking with 3% BSA in PBST for 30 min at RT, cells were incubated with ThS (Sigma) at 0.1 mg/ml in PBS for 10 min and rinsed 5 times with 80% Ethanol and once with PBS. Coverslips were then incubated with primary antibodies for 2 h at RT (see Table M.1). The cells were rinsed five times with PBST and subsequently incubated with the secondary antibodies at a dilution of 1/800 in PBST and DAPI at 2 µg/ml (Life technologies). The cells were washed five times in PBST, once in PBS and rinsed in MilliQ water before mounting in PVA medium with DABCO (Sigma). The cells were then examined with confocal laser-scanning microscope (LSM 700, Zeiss) and analyzed using Zen software.

Tau Seeding and Aggregation

The data on FIG. 19 show that using an independent assay of Tau seeding and aggregation, it is possible to validate and establish that the R2 peptide and the recombinant PHFs both can seed the aggregation of Tau.

Tau Biosensor Assay Workflow (FIG. 19 A)

Based on Furman and Diamond, 2017. FRET and Flow Cytometry Assays to Measure Proteopathic Seeding Activity in Biological Samples. Caroline Smet-Nocca (ed.), Tau Protein: Methods and Protocols, Methods in Molecular Biology, vol. 1523, DOI 10.1007/978-1-4939-6598-4_23, © Springer Science+Business Media New York 2017).

R2 Fibrils and rPHF Fibrils Seed Aggregation in Biosensor Cell Assay (FIG. 19 B)

Methods: FRET flow cytometry Biosensor cell assay (Furman and Diamond, 2017) was used to assess the seeding capacity of fibrillar R2 compared to R2 monomer, and fibrillar rPHF compared to 4R2N monomer Results: R2 fibrils and rPHF fibrils show increase in the IFD (2 experimental repeats, 3 technical replicates per condition, bars=st.dev.). No effective seeding (Integrated FRET Density=0) is observed in the control conditions of biosensor cells seeded with R2 monomer, 4R2N monomer, alpha-synuclein preformed fibrils, Lipofectamine-only or in control non-fluorescent HEK293T cell line.

Confocal Microscopy of Aggregates in Tau Biosensor Cells Induced by R2 and rPHF Transduction (FIG. 19 C)

Methods: cells were transduced with transduction buffer, R2 monomer, rPHFs or R2 fibrils following protocol by Furman and Diamond (2017).

Results: R2 fibril and rPHF fibril-transduced cells exhibit bright aggregated puncta (arrows).

Pre-Incubation of R2 Fibrils with Antibodies Significantly Reduces Tau Aggregation in Biosensor Cells (FIG. 19 D)

Methods: R2 fibrils were incubated with PBS, glycerol or with antibodies before transduction into tau biosensor cells. FRET+ tau aggregation was assessed using flow cytometry. 3 replicates/condition.

Results: show significant reduction (one-tail Student's t-test) in the amount of aggregate-containing cells in cultures seeded by the R2 incubated prior with antibodies rPHF1, R2m1 and R2f1 compared to the cultures seeded by R2 incubated prior with PBS or glycerol control. Results suggest pre-incubation of R2 with antibodies rPHF1, R2m1 and R2f1 prior to transduction into culture reduces the seeding/uptake efficiency in BS cells.

Tau Aggregation in Different Types of Neurons

Figure 20A:
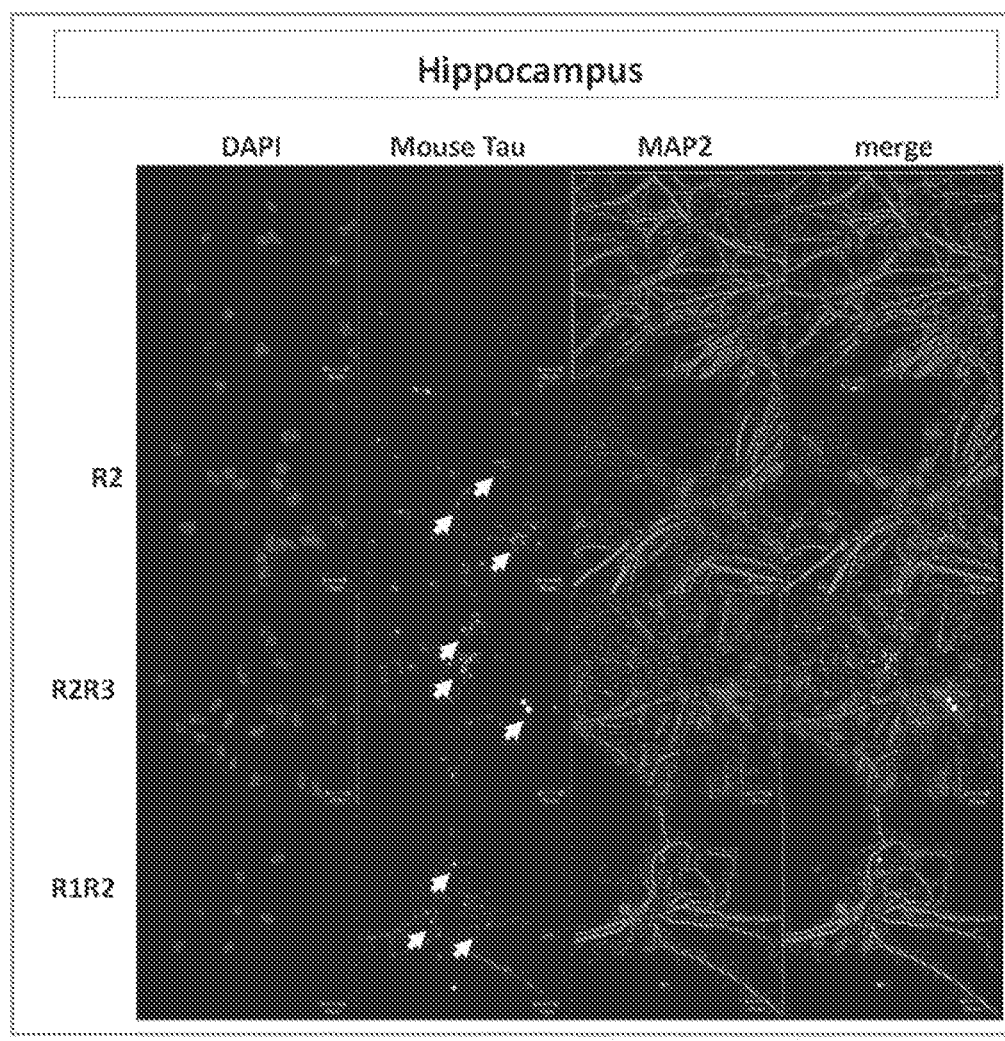
FIG. 20 shows R2 seeds aggregation in hippocampal (A) and cortical (B) mouse primary neurones.
Figure 20B:
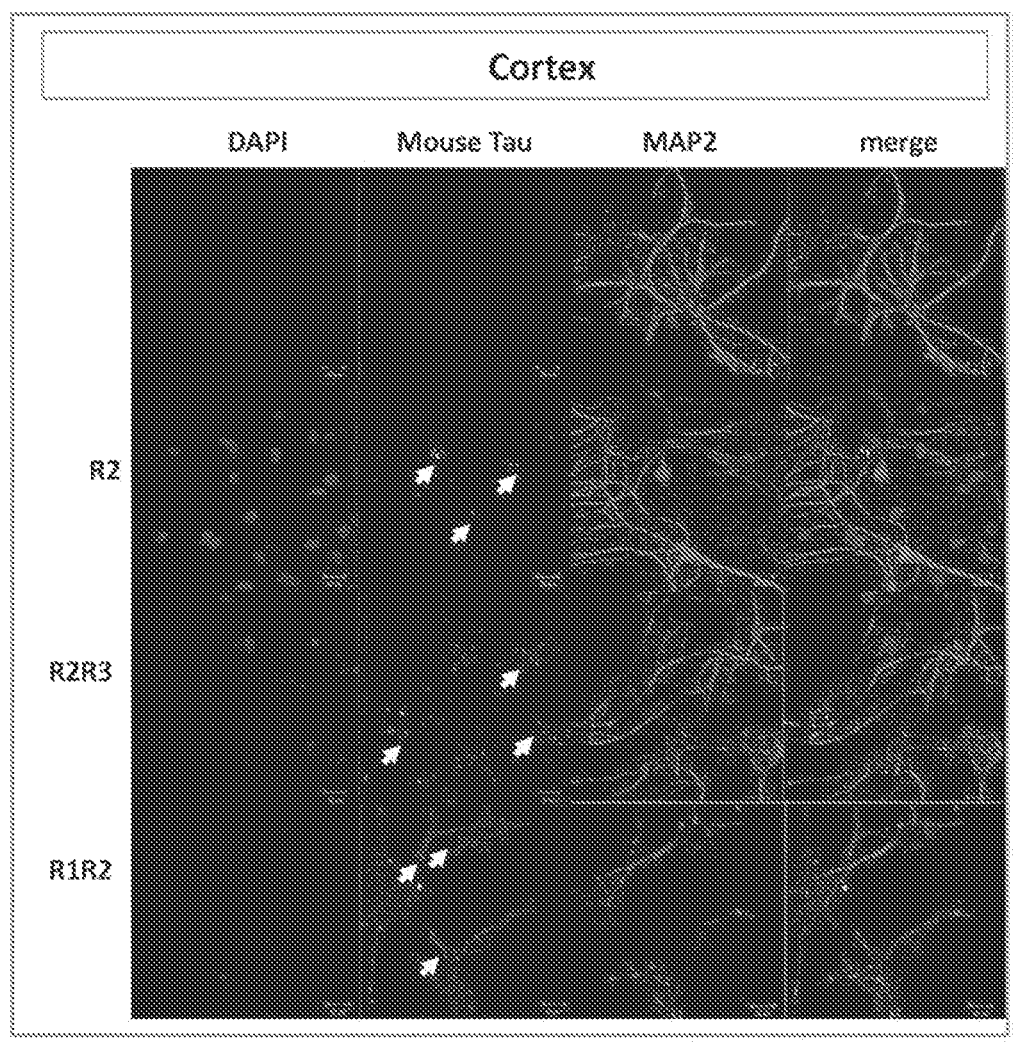

It is here further establish (see FIG. 20) the ability of the R2 peptides or other R2 containing peptides to seed tau aggregation in different types of neurons. The other point shown here is that Tau derived peptides that contain the R2 are likely to maintain this seeding capacity with higher seeding activity for peptides in which the R2 peptide is exposed (e.g. R2R3).

R2 Seeds Aggregation in Hippocampal (A.) and Cortical (B.) Mouse Primary Neurones:

Methods: mouse primary neurones were transduced at day 6 in vitro (6 DIV) with fibrillary R2, R1R2 or R2R3 and incubated for 20 days. Aggregation or mouse tau was assessed using confocal microscopy.

Results: Aggregation of mouse tau into bright puncta (arrows) is visible at DIV26 in hippocampal and cortical neurones, indicating efficient seeding of R2 fibrils internalised into cells.

Antibodies Against rPHFs

Antibodies were generated against the recombinant PHFs (rPHFs) and this data is used to establish that these antibodies are specific and recognize the rPHFs.

Figure 21:
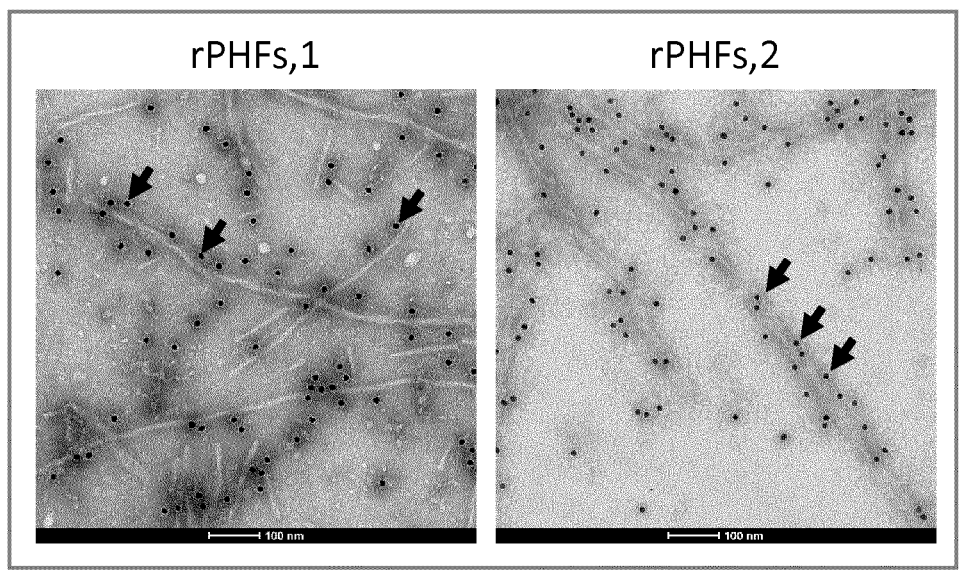
FIG. 21 shows immunogold labelling of rPHFs with anti-rPHF antibodies.

Immunogold Labelling of rPHFs with Anti-rPHF Antibodies (FIG. 21):

Methods: rPHF fibrils were mixed with R2 fibrils and labelled with rPHFs,1 and rPHFs,2 primary antibodies (dilution 1:10'000), followed by incubation with gold-labelled secondary antibodies (dilution 1:10) and imaged using transmission electron microscopy.

Results: preferential labelling of rPHFs is observed for antibodies rPHFs,1 and rPHFs,2 (arrows)

Immunoprecipitation Experiments Show Antibody rPHFs,1 and rPHFs,2 Affinity for Tau Monomers and rPHFs (FIG. 22):

Methods: pulldown experiments, visualised by Western blotting (A) and dot blots (B) were carried out using tau monomer and rPHFs inputs against bead-immobilised antibodies rPHF,1 and rPHF,2 raised against rPHF tau. Homemade antibody recognising total tau was used as a positive control. (Legend: rem=remainder, IP=immunoprecipitate). Membranes and were probed by (A) HT7 antibody, recognising epitope of tau between amino acids 159 and 163, (PPGQK) (SEQ ID NO:12), and (B) 77G7 antibody, recognising epitope of tau between amino acids 270-375 in microtubule-binding region.

Results: immunoprecipitation experiments show affinity of antibodies rPHF,1 and rPHF,2 show high affinity for rPHFs visualised using Western blotting (A, blue boxes) and dot blots (B, blue arrows).

Antibodies

Antibodies against the following proteins/peptides have been generated:

Recombinant PHFs (rPHF), rPHF,1 and rPHF,2
The R2 peptide monomer, R2,1 and R2,2
The R2 peptide fibril seeds, R2f1 and R2f2

Figure 23:
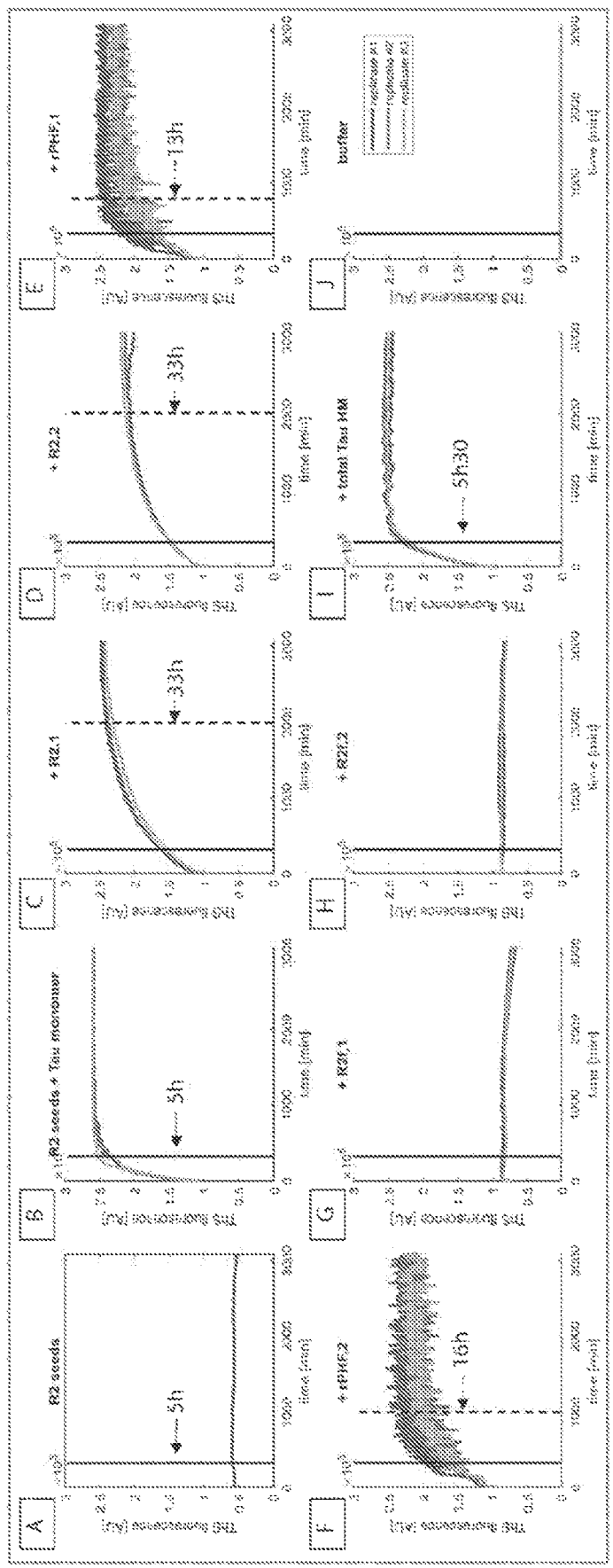
FIG. 23 shows antibodies that modify seeding capacity of R2 fibrils in vitro.

The data (see FIG. 23) show that co-incubation with the R2 fibril seeds with antibodies that were raised against the fibril seed showed complete inhibition of Tau seeding capacity in vitro. Whereas coincubation with antibodies against the monomers did not show any effect. Similarly, co-incubation with antibodies against the final product, the rPHFs, did not affect the seeding capacity of the R2-fibrils. This is expected since these antibodies do not recognize the seed, but recognize instead the final product, which requires not only aggregation of Tau but maturation into PHFs.

These results show that antibodies raised against the aggregated forms of R2-containing peptides represents a very promising strategy to interfer with Tau seeding and pathology spreading.

Antibodies Modify Seeding Capacity of R2 Fibrils In Vitro (FIG. 23):

Methods: R2 fibril seeds were pre-incubated with the different antibodies for 1 h at room temperature. The monomeric tau protein was added and the aggregation was monitored by ThT fluorescence.

Results: No ThT fluorescence is observed in buffer (J) and at basal R2 fibril seed-only conditions (A) With addition of tau monomer to R2 fibril seeds the aggregation proceeds without the lag phase, indicating the efficient polymerisation by primary nucleation due to seeding (Cohen, S. I., Vendruscolo, M., Dobson, C. M. and Knowles, T. P., 2011. Nucleated polymerisation in the presence of pre-formed seed filaments. International journal of molecular sciences, 12(9), pp. 5844-5852), with reaction reaching saturation plateau phase at around 5 h 30 min (arrow) into the reaction (B). Upon pre-incubation with the antibodies R2,1, R2,2, rPHFs,1, rPHFs,2 (C, D, E, F) the exponential phase of seeding is extended, with rPHFs,1 and with rPHFs,2 reactions reaching plateau phase after ~13-16 h of incubation (E, F, dashed lines), and R2,1 and R2,2 reactions reaching the saturation phase at the excess of incubation of 33 h (C, D, dashed lines). Pre-incubation of R2 fibril seeds with antibodies R2f,1 and R2f,2 completely abolishes seeding and aggregation reaction (G, H). Pre-incubation of R2 fibril seeds with control antibody Tau HM does not reduce seeding capacity of R2 fibril seeds, with saturation curve reaching plateau (I) at the similar time point to the positive control reaction (B).

The invention claimed is:

1. A method for preparing paired-helical filaments (PHFs)-like Tau aggregates comprising:
   (a) contacting R2 fragments consisting of SEQ ID NO: 1 with polyanions,
   (b) allowing formation of R2 fibrils,
   (c) breaking down the R2 fibrils into seeds,
   (d) contacting Tau proteins comprising SEQ ID NO: 1 with the R2 fibril seeds under conditions which allow Tau aggregation, wherein the Tau proteins comprising SEQ ID NO: 1 are selected from the group consisting of full length Tau proteins 4R2N (SEQ ID NO: 5), Tau microtubule binding domain (K18) (SEQ ID NO: 6), Tau protein 4R1N (SEQ ID NO: 7), Tau protein 4R0N (SEQ ID NO: 8), mouse Tau isoform m4R2N (SEQ ID NO: 9), mouse Tau isoform m4R0N (SEQ ID NO: 10) and a combination thereof.

2. The method of claim 1, wherein the polyanions are selected from the group consisting of heparin, arachidonic acid, polysulfates, DNA, RNA, fatty acid micelles and negatively charged surfaces.

3. A method for identifying compounds that are inhibitors of Tau aggregation, propagation and/or toxicity comprising:
   (a) contacting Tau proteins comprising SEQ ID NO: 1 and R2 fibrils obtained by the method of claim 1 in the presence and absence of a test compound under conditions which allow Tau protein aggregation, propagation and/or toxicity effects,
   (b) determining the amount of PHFs-like Tau aggregates formed in the presence and absence of the test compound, and
   (c) comparing the amount of PHFs-like Tau aggregates formed in the presence of the test compound with the amount of PHFs-like Tau aggregates formed in the absence of the test compound, wherein the test compound which decreases the amount of PHFs-like Tau aggregates formed, decreases PHFs-like Tau propagation and/or decreases PHFs-like Tau toxic effect is an inhibitor.

4. A method for preparing in-vivo imaging agents that bind to native Tau aggregates, the method comprising labelling PHFs-like Tau aggregates obtained by the method of claim 1 with an in-vivo imaging moiety.

5. A method of detecting PHFs or native Tau aggregates in a subject, the method comprising administering an imaging agent comprising the PHFs-like Tau aggregates obtained by the method of claim 1 and an in-vivo imaging moiety to the subject.

6. A method for identifying compounds that bind to PHFs or native Tau aggregates comprising:
   (a) contacting Tau proteins comprising SEQ ID NO: 1 and the R2 fibrils obtained by the method of claim 1 in the presence and absence of a test compound under conditions which allow Tau protein aggregation, propagation and/or toxicity effects,
   (b) determining the amount of PHFs-like Tau aggregates formed in the presence and absence of the test compound, and
   (c) comparing the amount of PHFs-like Tau aggregates formed in the presence of the test compound with the amount of PHFs-like Tau aggregates formed in the absence of the test compound, wherein the test compound which decreases the amount of PHFs-like Tau aggregates formed, decreases PHFs-like Tau propagation and/or decreases PHFs-like Tau toxic effect binds to PHFs or native Tau aggregates.

* * * * *